United States Patent
Heckrodt et al.

(10) Patent No.: US 9,029,501 B2
(45) Date of Patent: May 12, 2015

(54) METHOD FOR MAKING MACROCYCLES

(75) Inventors: Thilo J. Heckrodt, San Francisco, CA (US); Rajinder Singh, Belmont, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 2 days.

(21) Appl. No.: 13/882,970

(22) PCT Filed: Nov. 1, 2011

(86) PCT No.: PCT/US2011/058814
§ 371 (c)(1),
(2), (4) Date: May 1, 2013

(87) PCT Pub. No.: WO2012/061408
PCT Pub. Date: May 10, 2012

(65) Prior Publication Data
US 2013/0217874 A1 Aug. 22, 2013

Related U.S. Application Data

(60) Provisional application No. 61/409,424, filed on Nov. 2, 2010.

(51) Int. Cl.
*A61K 38/12* (2006.01)
*C07K 5/00* (2006.01)
*C07K 5/02* (2006.01)
*C07K 5/062* (2006.01)
*C07K 5/065* (2006.01)

(52) U.S. Cl.
CPC .............. *C07K 5/02* (2013.01); *C07K 5/06026* (2013.01); *C07K 5/06078* (2013.01)

(58) Field of Classification Search
None
See application file for complete search history.

(56) References Cited

U.S. PATENT DOCUMENTS

| | | | |
|---|---|---|---|
| 2001/0047095 A1 | 11/2001 | Sibert | |
| 2004/0209895 A1 | 10/2004 | Luecking et al. | |
| 2006/0217321 A1* | 9/2006 | Ozeki | 514/19 |
| 2009/0111152 A1* | 4/2009 | Sherman et al. | 435/120 |
| 2010/0081701 A1 | 4/2010 | Evans | |

FOREIGN PATENT DOCUMENTS

| | | |
|---|---|---|
| WO | WO 2009/137432 | 11/2009 |
| WO | WO 2010/006682 | 1/2010 |

OTHER PUBLICATIONS

ChemicalBook, CAS No. 3081-61-6,L—Theanine Product Information, 2014.*
International Search Report from International Application No. PCT/US2011/058814, dated May 1, 2012.
Written Opinion from International Application No. PCT/US2011/058814, dated May 1, 2012.

* cited by examiner

*Primary Examiner* — James H Alstrum Acevedo
*Assistant Examiner* — Jeanette Lieb
(74) *Attorney, Agent, or Firm* — Travis Young; Klarquist Sparkman, LLP

(57) ABSTRACT

Disclosed embodiments concern a method for making substantial quantities of desired macrocycles. Disclosed ring closing reactions make the macrocycle with desired olefin geometry in excellent yield and E/Z ratio. Particular embodiments of the current method concern intermediates that are obtained from commercially available starting materials in a small number of steps, thereby illustrating the commercial importance and applicability of the disclosed method. The macrocycle produced by the ring closing reaction can be further derivatized to provide analogs of the macrocyclic compounds.

30 Claims, No Drawings

METHOD FOR MAKING MACROCYCLES

CROSS REFERENCE TO RELATED APPLICATIONS

This is the U.S. National Stage of International Application No. PCT/US2011/058814, filed Nov. 1, 2011, which was published in English under PCT Article 21(2), which in turn claims the benefit of U.S. Provisional Application No. 61/409,424, filed Nov. 2, 2010. Both of these prior applications are incorporated herein by reference in their entirety.

FIELD

The present disclosure concerns embodiments of a method for making and using macrocyclic compounds.

BACKGROUND

Biological activity is typically conferred by a set of structural features in a molecule that is recognized at a biological target, e.g., a receptor site. These features include steric and electronic features. Such a set of structural, steric and/or electronic features is termed a "pharmacophore." Natural products and peptides are among compounds that have consistently been found to possess potent and selective biological activity.

Many enzymes and receptors interact with proteins, particularly with a pharmacophoric portion of a protein. Because only a small portion of the protein may be responsible for the pharmacophoric effect, exposing an enzyme or receptor to a peptide containing the pharmacophoric features may have the same effect. Thus, development of synthetic and/or modified peptides or peptide analogs can be used to potentially produce more potent agonists or inhibitors of these enzymes and receptors.

Because many enzymes and receptors interact with protein and/or peptide ligands, synthetic peptides and peptide analogs are promising candidates for biological activity screening assays. Of particular interest are synthetic peptides and/or peptide analogs that may have activity against targets (e.g., receptors and/or enzymes) involved in immunologic reactions. Molecules with strong activity as either agonists or inhibitors may be used to develop new drugs and/or treatments.

In some instances, a particular amino acid or side chain, or a combination of amino acids and/or side chains, possesses pharmacophoric activity. Incorporation of these particular amino acids and/or side chains into a synthetic molecule may produce a compound with a desired biological activity. To facilitate access of these amino acids and/or side chain moieties to the active site on an enzyme or receptor, some researchers have attached the moieties to a scaffold or rigid structure such as, for example, an aromatic ring or a sugar.

In another approach, a peptide can be cyclized to facilitate its interaction with a receptor or an enzyme, thereby improving its pharmacological and/or physiological activity. A cyclic peptide can have several advantages compared to its linear analog including, but not limited to, constrained conformational mobility, defined topology, protection from proteolytic enzymes, and/or altered polarity. Additionally, compared to its linear analog, the cyclic peptide may have increased activity, selectivity, stability, bioavailability, and/or membrane permeability.

Drugs based on macrocyclic compounds (e.g., compounds with large rings containing seven or more carbon atoms) play an important role in modern medicine. Current macrocyclic drugs are almost exclusively derived from natural sources and are either identical (e.g., rapamycin, an immunosuppressant drug used to prevent rejection in organ transplantation) or closely related to naturally occurring macrocycles (e.g., temsirolimus, a drug for the treatment of renal cell carcinoma). However, synthetic macrocyclic compounds will be a valuable source of additional compounds to screen for biological activity and subsequent use in drug development.

SUMMARY

Certain disclosed embodiments concern a method for making a macrocycle, comprising subjecting an acyclic precursor to conditions sufficient to form the macrocycle having a formula

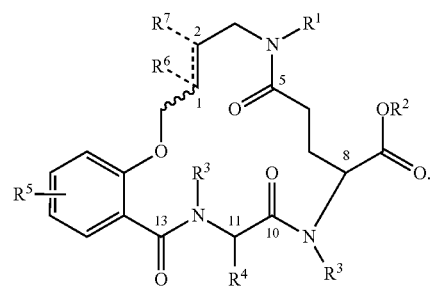

With reference to this general formula, $R^1$ can be selected from hydrogen, aliphatic (alkyl, alkenyl, alkynyl), substituted aliphatic, aromatic, substituted aromatic, arylalkyl, substituted arylalkyl, benzoyl, ester, ketone, tert-butoxycarbonyl, 9H-fluoren-9-ylmethoxycarbonyl, allyloxycarbonyl, benzyloxy carbonyl, trichloroethoxycarbonyl, triphenylmethyl, and sulfonyl. $R^2$ can be selected from hydrogen, aliphatic, substituted aliphatic, typically alkyl, more typically lower alkyl. Each $R^3$ is independently selected from hydrogen, aliphatic, substituted aliphatic, aromatic, substituted aromatic, arylalkyl, substituted arylalkyl, benzoyl, ester, ketone, tert-butoxycarbonyl, 9H-fluoren-9-ylmethoxycarbonyl, allyloxycarbonyl, benzyloxy carbonyl, trichloroethoxycarbonyl, triphenylmethyl, and sulfonyl. $R^4$ can be selected from hydrogen, lower alkyl, substituted lower alkyl, —CH(CH$_3$)CH$_2$CH$_3$, —CH(CH$_3$)$_2$, —(CH$_2$)$_2$SCH$_3$, benzyl, 3-indole, —CH(CH$_3$)$_2$, —CH$_2$OH, —CH(OH)(CH$_3$), —CH$_2$C(O)NH$_2$, —(CH$_2$)$_2$C(O)NH$_2$, —CH$_2$SH, —CH$_2$SeH, —(CH$_2$)$_3$NHC(NH$_2^+$)NH$_2$, —CH$_2$(imidazole), —(CH$_2$)$_4$NH$_2$, —CH$_2$C(O)OH, —(CH$_2$)$_2$C(O)OH, natural amino acids, and non-natural amino acids. $R^3$ and $R^4$ also either individually or together may form a 5-membered ring. $R^5$ can be selected from aliphatic, substituted aliphatic, alkoxy, substituted alkoxy, amine, substituted amine, amide, substituted amide, aryl, substituted aryl, arylalkyl, substituted arylalkyl, cyclic, substituted cyclic, ester, ether, formyl, halogen, heterocyclic, substituted heterocyclic, heteroaryl, substituted heteroaryl, hydrogen, hydroxyl, ketone, substituted ketone, nitro, nitroso, protecting groups, silyl, silyl ether, silyl ester, thiol, thioether, thioester. "$====$" indicates an optional double bond, having either Z or E geometry. $R^6$ and $R^7$ can be hydrogen when the optional double bond is present; when the optional double bond is not present, $R^6$ and $R^7$ can be selected from aliphatic, substituted aliphatic, amino, halogen, hydrogen, hydroxyl, or $R^6$ and $R^7$ together form an epoxide or aziridine. The macrocycle can be a single diastereomer or a mixture of diastereomers.

Particular embodiments concern an acyclic precursor having a formula

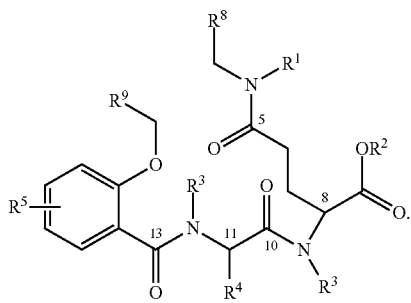

With reference to this general formula, $R^1$-$R^5$ are as previously recited. $R^8$ and $R^9$ can be selected from —$CR^{10}$=$CR^{11}R^{12}$, where $R^{10}$, $R^{11}$, and $R^{12}$ are selected from hydrogen, aliphatic, substituted aliphatic, aromatic, substituted aromatic, arylalkyl, substituted arylalkyl, —C(O)H, —$CH_2SO_2Ph$, —$CH_2PPh_3$, —$CH_2P(O)(OCH_2CF_3)_2$, —$CH_2P(O)(OEt)_2$, and —$CH_2SO_2$-tetrazole.

In other embodiments, the acyclic precursor can have a formula

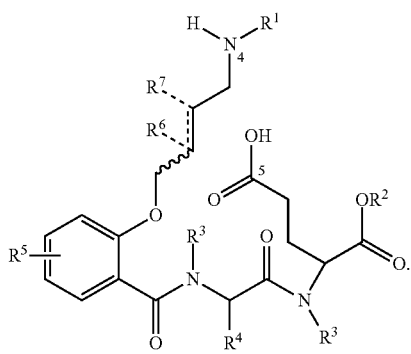

With reference to this general formula, $R^1$-$R^7$ are as previously recited.

In yet another embodiment, the acyclic precursor can have a formula

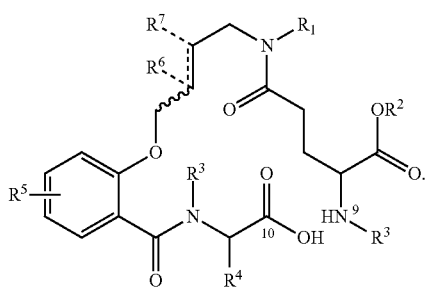

With reference to this general formula, $R^1$-$R^7$ are as previously recited.

In yet other embodiments, the acyclic precursor can have a formula

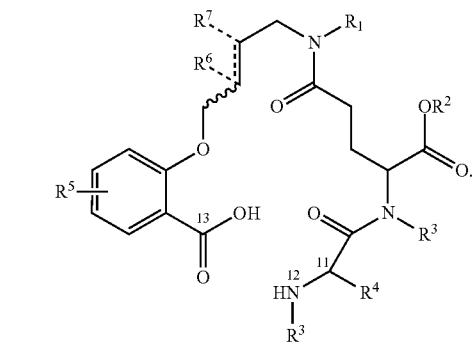

With reference to this general formula, $R^1$-$R^7$ are as previously recited.

Particular embodiments concern a method for making a macrocycle having a formula

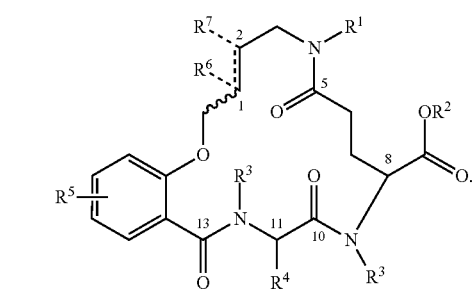

With reference to this general formula, $R^6$ and $R^7$ independently can be selected from aliphatic, substituted aliphatic, amino, halogen, hydrogen, hydroxyl, or $R^6$ and $R^7$ together can form an epoxide or aziridine.

Certain disclosed embodiments also concern using a ring closing metathesis reaction to form a macrocycle from an acyclic precursor having a formula

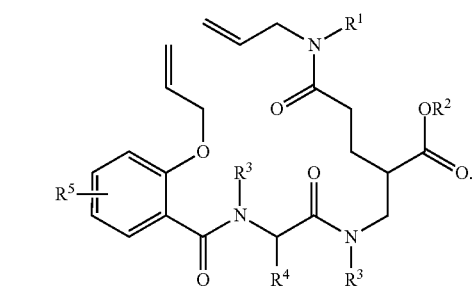

With reference to this general formula, $R^1$-$R^5$ are as previously recited.

Certain embodiments concern acyclic precursors having the following structures.
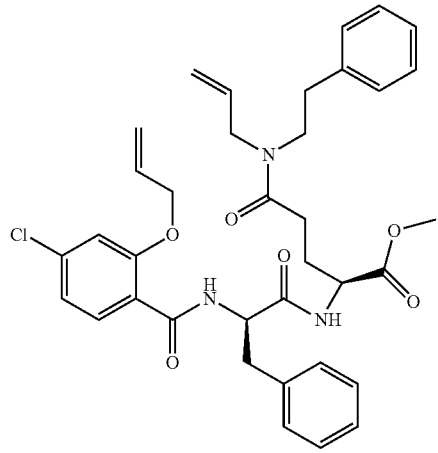
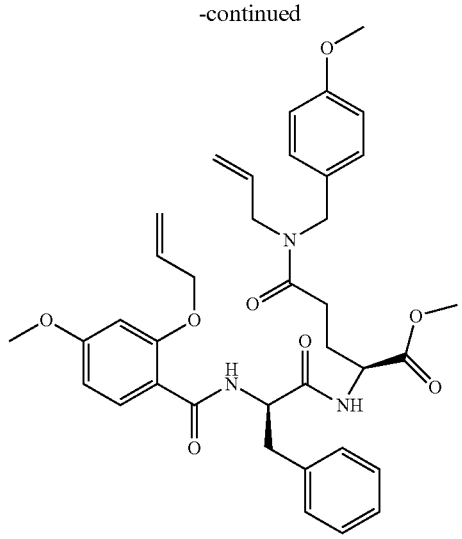
Particular embodiments concern macrocycles having the following structures.
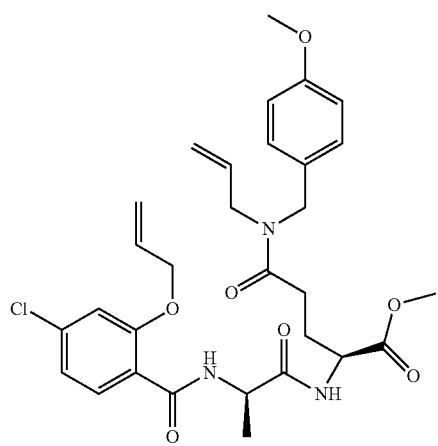
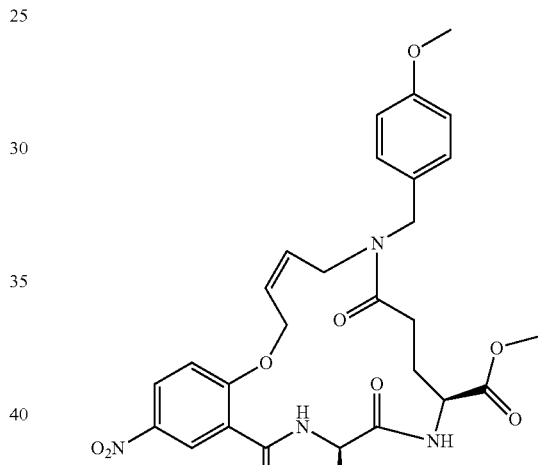
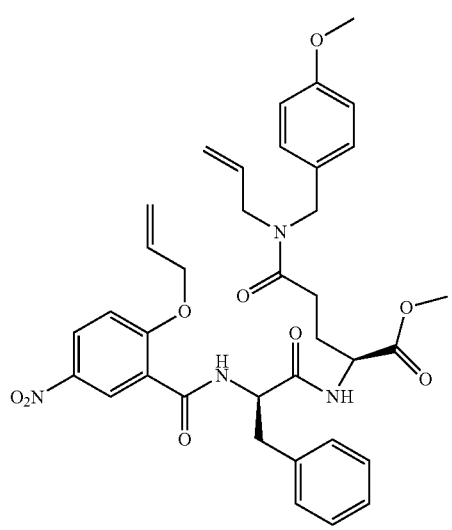
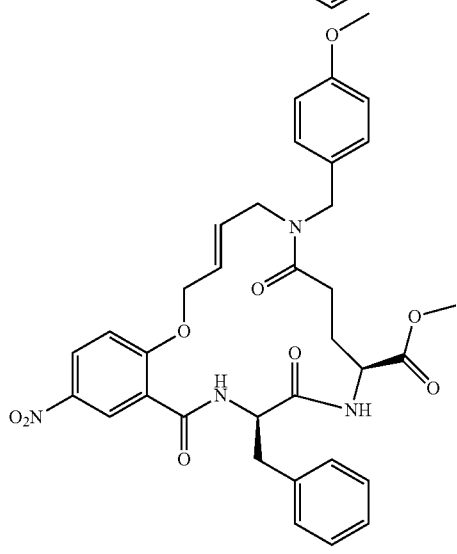

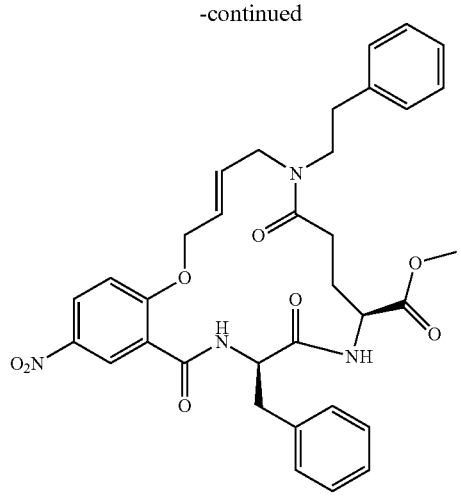
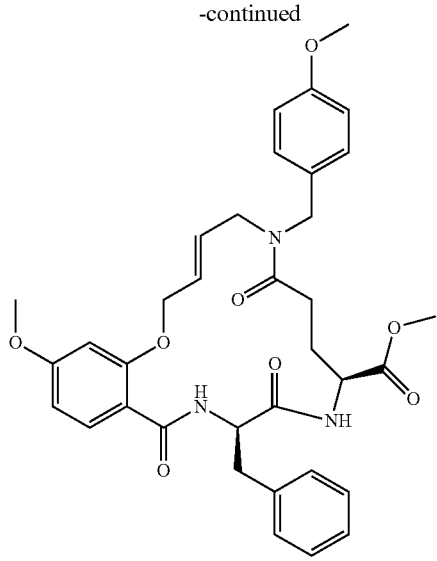
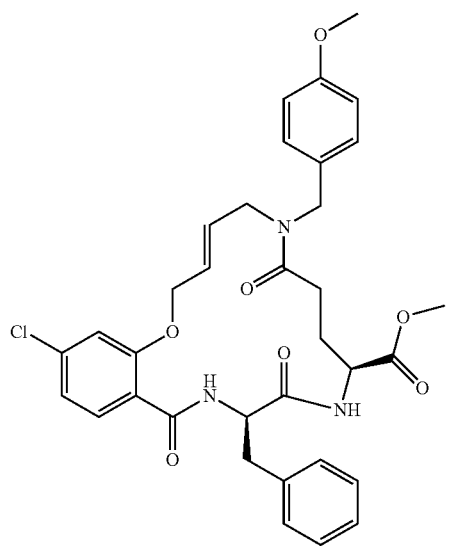
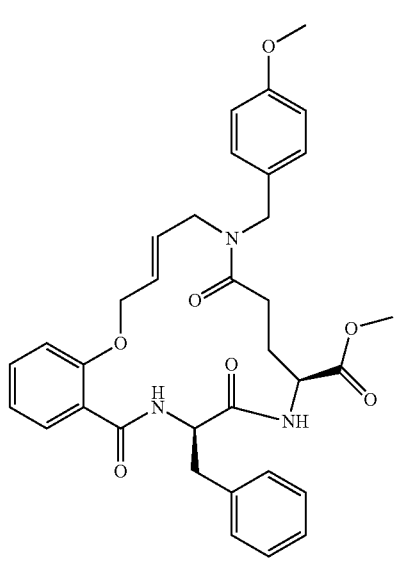
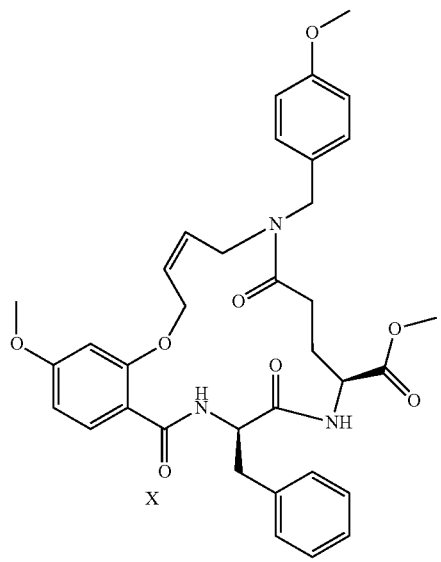
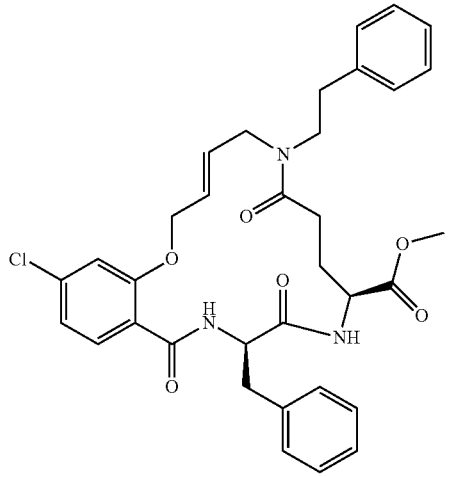

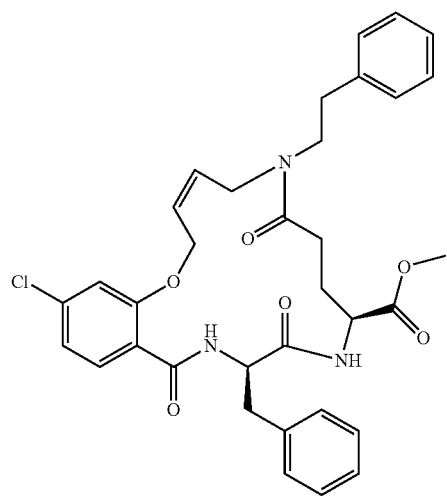
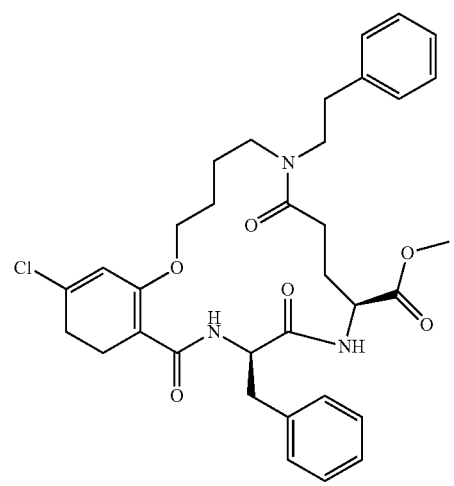
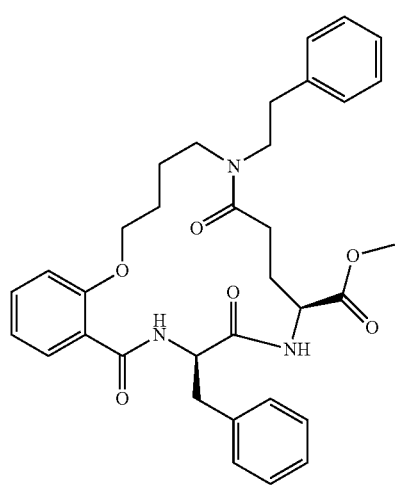
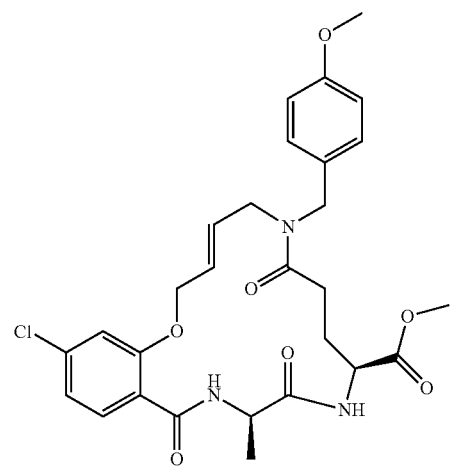
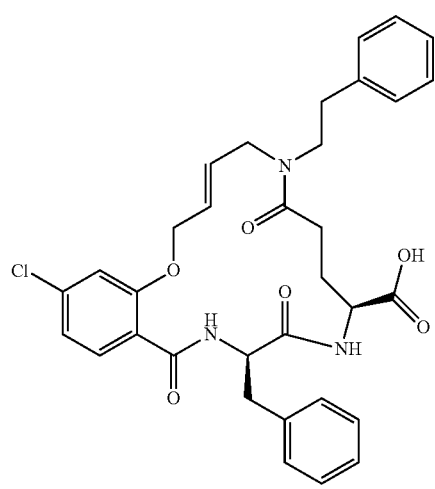
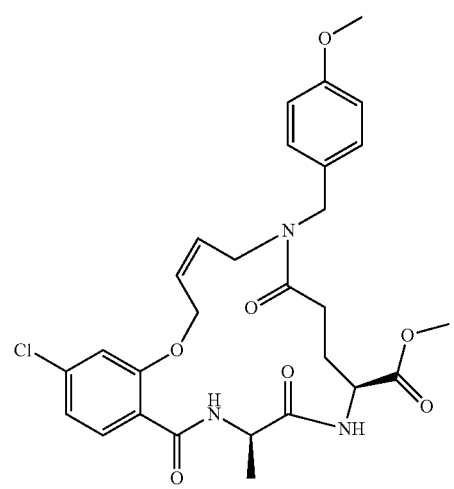

-continued

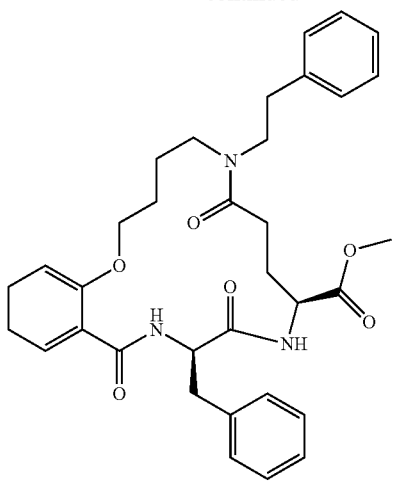

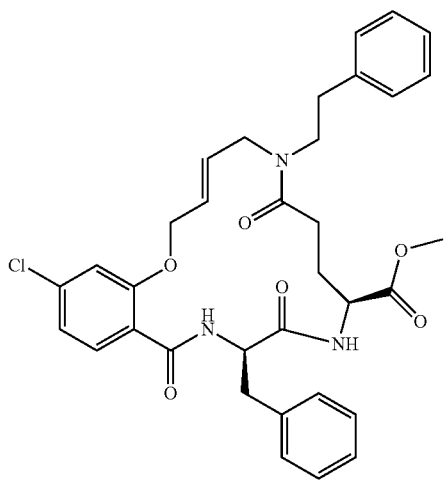

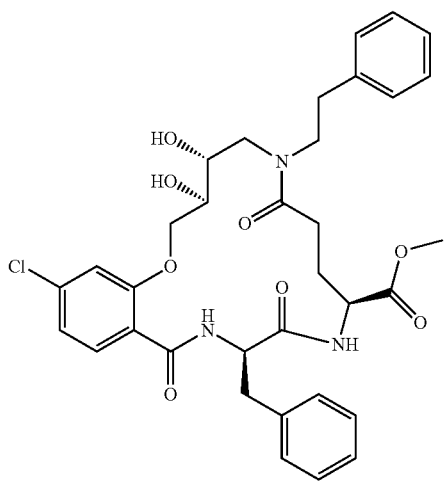

Certain embodiments concern forming the acyclic ring precursor by coupling a salicylic acid derivative with a dipeptide using peptide coupling conditions. The salicylic acid derivative can be obtained by a substitution reaction with a salicylic acid starting material. The dipeptide can comprise naturally occurring amino acids, non-naturally occurring amino acids, or both. More typically, the dipeptide is a glutamic acid derivative formed from a halogenated compound having the formula

wherein $R^8$ is $-CR^{10}=CR^{11}R^{12}$ with $R^{10}$, $R^{11}$, and $R^{12}$ independently being selected from aliphatic, substituted aliphatic, $-C(O)H$, $-CH_2SO_2Ph$, $-CH_2PPh_3$, $-CH_2P(O)(OCH_2CF_3)_2$, $-CH_2P(O)(OEt)_2$, $-CH_2SO_2$-tetrazole and any other reagent capable of undergoing ring closing metathesis or olefination (under basic conditions). X is selected from I, Br, Cl, F. The halogenated compound can then be reacted with a first amine compound having a formula $NH_2R^1$ where $R^1$ can be selected from hydrogen, aliphatic, substituted aliphatic, aromatic, substituted aromatic, arylalkyl, substituted arylalkyl, ester, ketone, benzoyl, triphenylmethyl, and sulfonyl, to form a second amine. The second amine formed from the reaction can be subjected to an amide bond formation reaction with a protected glutamic acid compound having a formula

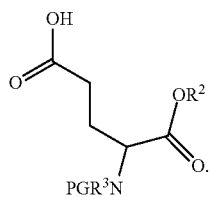

With reference to this general formula, $R^2$ and $R^3$ are as previously described. PG can be selected from arylalkyl, substituted arylalkyl, benzoyl, ester, ketone, triphenylmethyl, and sulfonyl. The amide bond formation reaction can use an activating group, capable of activating a carboxylic acid moiety present in the protected glutamic acid derivative, typically selected from N-ethyl-N'-(3-dimethylaminopropyl)carbodiimide (EDC), 1-ethyl-3-(3-dimethylaminopropyl)carbodiimide hydrochloride (EDCI), dicyclohexylcarbodiimide (DCC), carbonyl diimidazole (CDI), 1-hydroxybenzotriazole (HOBt), 1-hydroxy-7-aza-benzotriazole (HOAt), and o-(7-azabenzotriazol-1-yl)-N,N,N',N'-tetramethyluronium hexafluorophosphate (HATU). This reaction can be used to obtain a substantially enantiopure glutamic acid derivative.

Particular embodiments concern a salicylic acid derivative having a formula

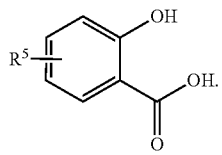

With reference to this general formula, $R^5$ is as previously recited.

Particular embodiments utilize salicylic acid derivatives having the following structures

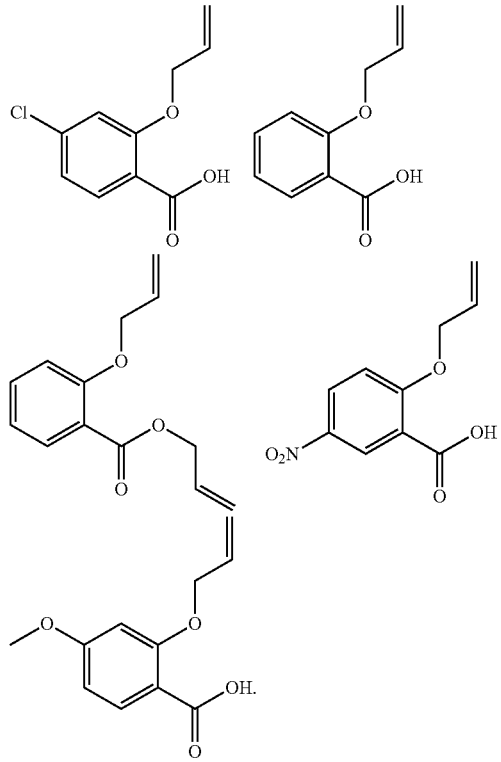

Certain embodiments concern forming an intermediate having the following general formula

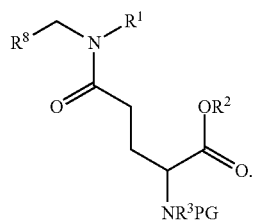

With reference to this general formula, $R^1$, $R^2$, $R^3$, $R^8$, and PG are as previously recited.

Particular intermediates are selected from the following structures

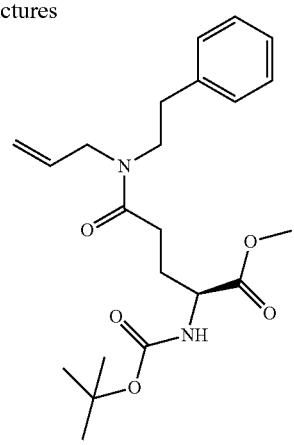

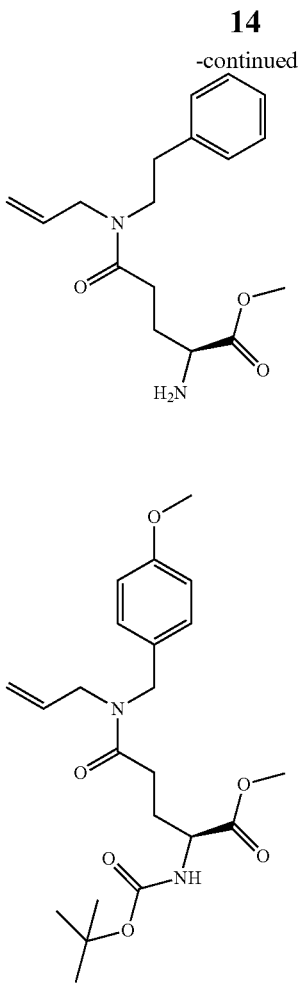

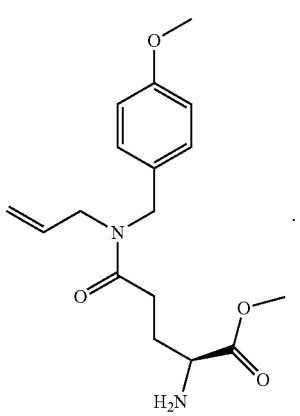

Other particular embodiments concern intermediates having a formula

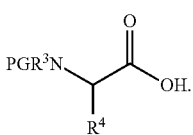

With reference to this general formula, $R^3$, $R^4$, and PG are as previously recited.
Certain embodiments have the following structures
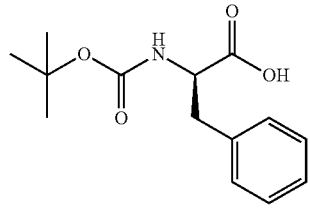
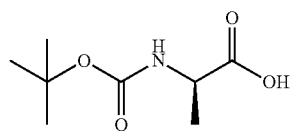
Yet another intermediate can have a formula
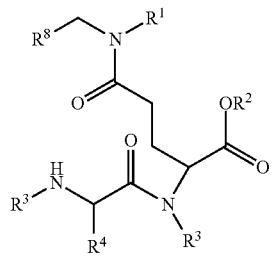
With reference to this general formula, $R^1$-$R^4$ and $R^8$ are as previously recited.
Particular embodiments of these intermediate have the following structures
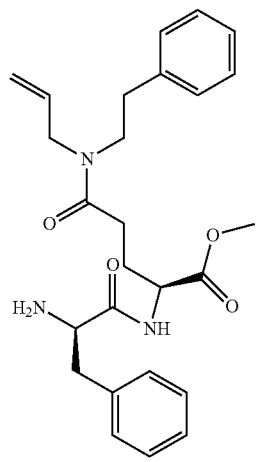
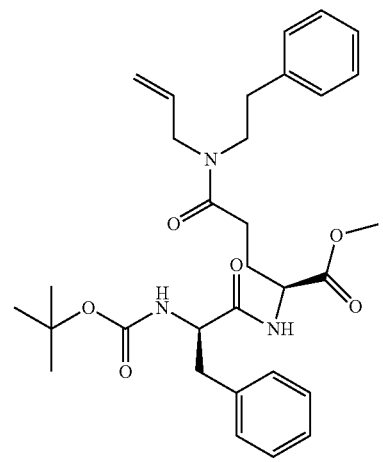
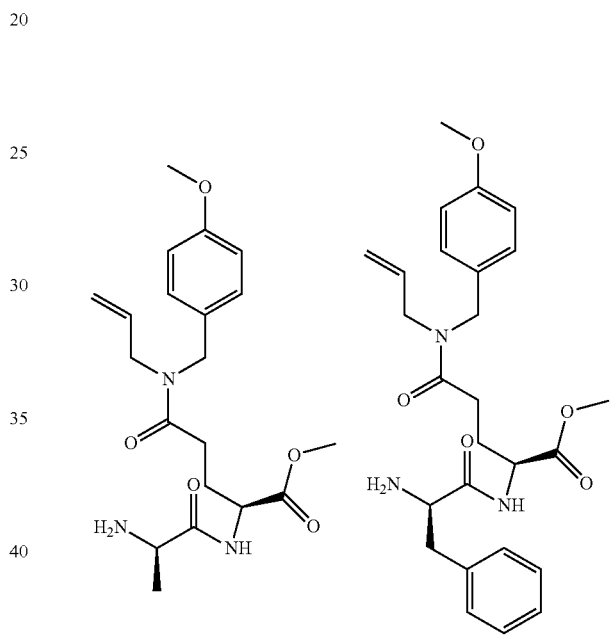
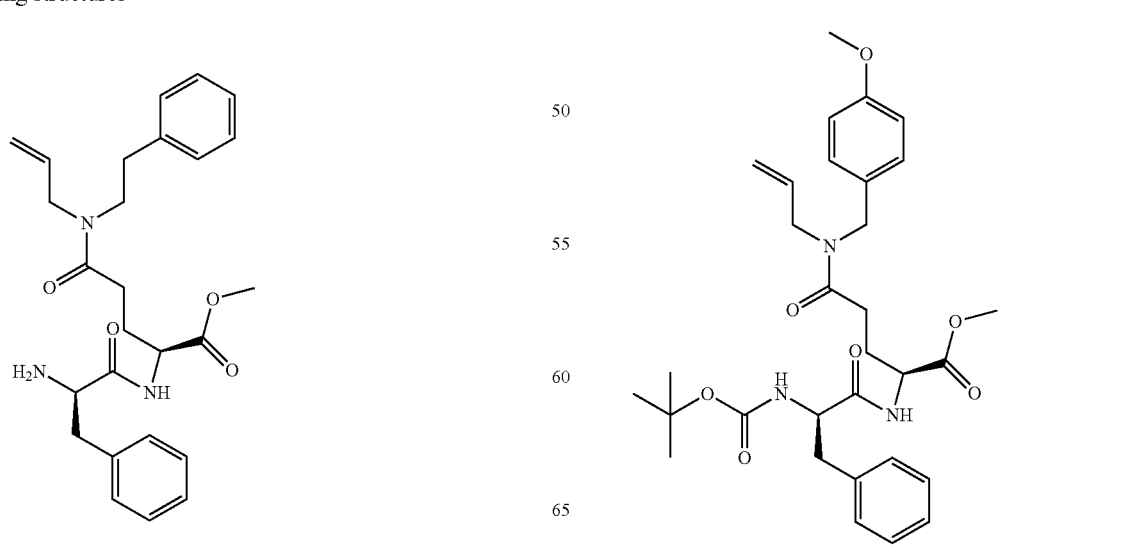

-continued

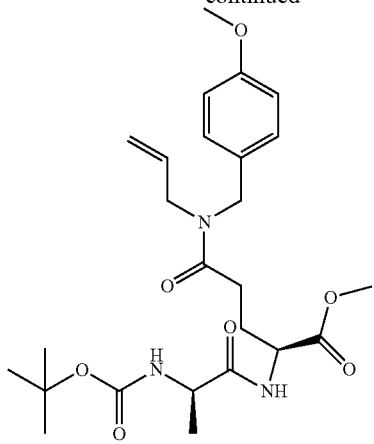

Particular embodiments concern forming a salicylic acid derivative that can be bis-substituted under basic conditions by reacting a first acid compound having a formula

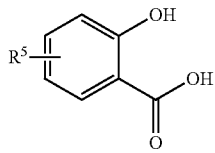

with a second halogenated compound having a formula

This bis-substituted compound is then hydrolyzed to form a salicylic acid derivative having a formula

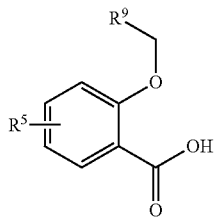

Particular embodiments of intermediates disclosed in the current method can be prepared by performing a peptide coupling between a glutamic acid derivative having a formula

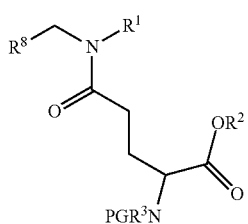

and a protected amino acid derivative having a formula

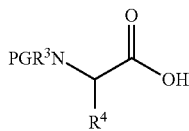

In particular embodiments of the disclosed method, an intermediate having a formula

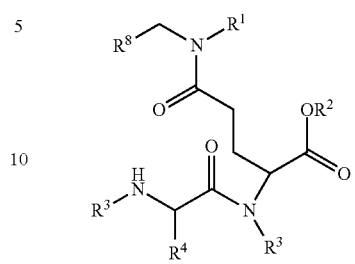

can be reacted with a salicylic acid derivative having a formula

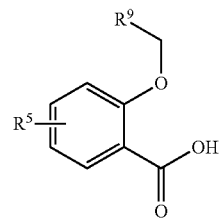

to provide a compound having a formula

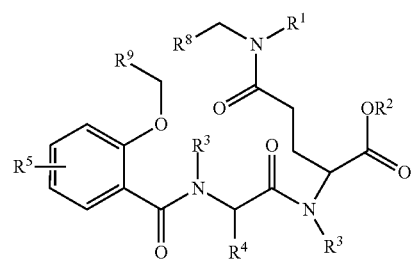

With reference to the above formulas, $R^1$-$R^5$, $R^8$, and $R^9$ are as previously recited.

Particular embodiments of the above intermediate can have the following structures

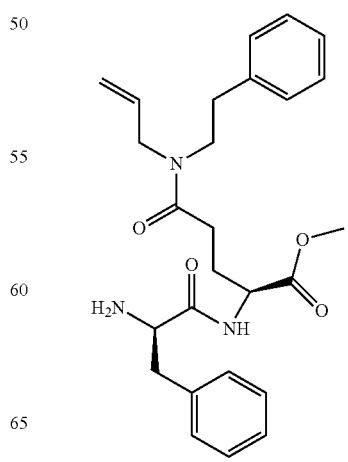

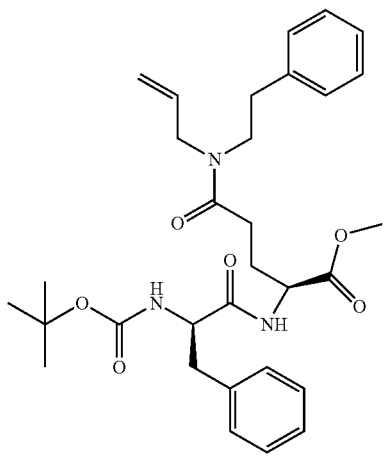
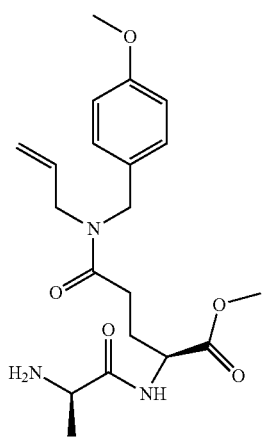
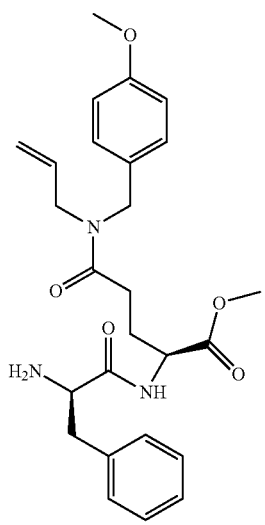
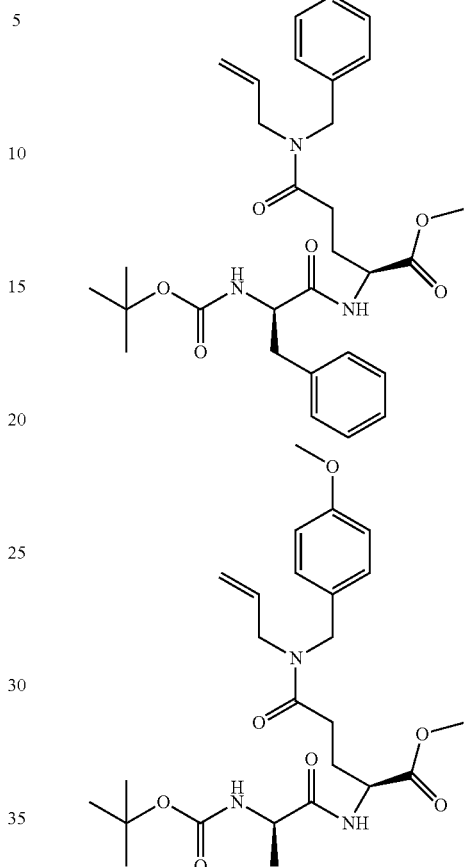

Other embodiments of acyclic precursors have the following formula

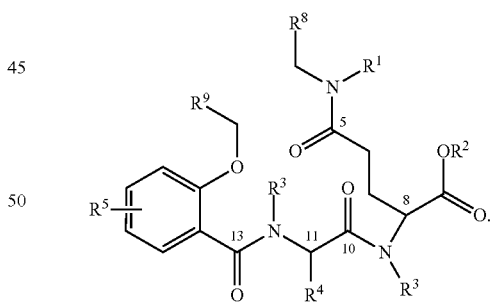

In particular embodiments, the disclosed ring closing reaction can be carried out with a transition metal carbene catalyst capable of catalyzing ring closing metathesis reactions, the catalysts being selected from Grubbs' 1st generation catalyst, Grubbs' 2nd generation catalyst, Grubbs-Hoveyda catalyst, and Schrock catalyst. In other embodiments, the ring closing reaction can involve a ring closing olefination reaction selected from Wittig olefination, Horner-Wadsworth-Emmons olefination, Gennari-Still olefination, Julia-Lythgoe and Julia-Kocienski olefinations, wherein $R^8$ of the acyclic ring precursor is —C(O)H, and $R^9$ can be selected from —CH$_2$SO$_2$Ph, —CH$_2$PPh$_3$, —CH$_2$P(O)(OCH$_2$CF$_3$)$_2$, —$CH_2P(O)(OEt)_2$, —$CH_2SO_2$-tetrazole, or where $R^9$ is —C(O)H, and $R_8$ is selected from —$CH_2SO_2Ph$, —$CH_2PPh_3$, —$CH_2P(O)(OCH_2CF_3)_2$, —$CH_2P(O)(OEt)_2$, —$CH_2SO_2$-tetrazole. Particular embodiments concern ring closing reactions that provide primarily E olefin geometry or primarily Z olefin geometry.

In particular embodiments, the macrocycle can be further derivatized to form macrocyclic analogs. Certain embodiments disclose a method for making a macrocycle wherein the ester moiety of the macrocycle (where $R^2$ is other than hydrogen and typically is aliphatic or substituted aliphatic) is hydrolyzed to the corresponding carboxylic acid where $R^2$ is hydrogen. In other embodiments, the macrocycle can undergo a palladium coupling reaction using a palladium catalyst as follows

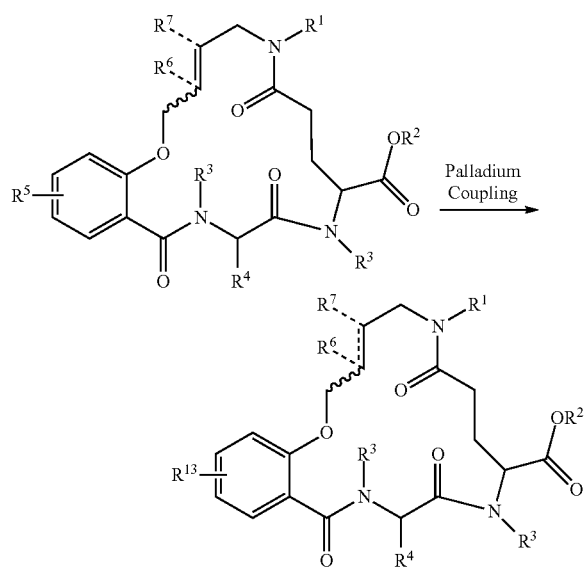

With reference to the above reaction scheme, $R^5$ is selected from I, Br, Cl, F, and OTf, more typically Br and Cl, $R^{13}$ is selected from aryl, substituted aryl, heteroaryl, substituted heteroaryl, aliphatic and substituted aliphatic. Particular embodiments concern using Suzuki couplings, Negishi couplings, Hiyama couplings, and Stille reactions to carry-out the palladium coupling. The palladium catalyst can be selected from any such catalyst capable of oxidatively adding to an aryl bond, particularly an aryl-halide bond, such as $Pd(OAc)_2$, $PdCl_2(dppf)_2$, $Pd(PPh_3)_4$, and $Pd_2(dba)_3$.

Other embodiments concern converting an olefin to a saturated moiety using a hydrogenation reaction, as illustrated below.

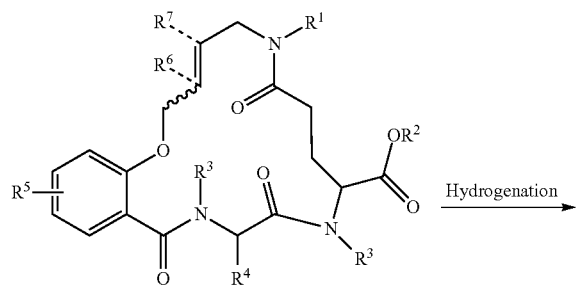

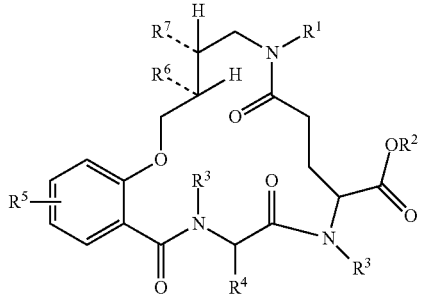

In particular embodiments, hydrogenation can be carried out using Pd/C under an atmosphere of $H_2$, diimide, or Lindlar's catalyst.

The current method can also provide macrocycles wherein the olefin resulting from the ring closing reaction is oxidized. In particular embodiments, the olefin can be oxidized to form a diol or an epoxide such that $R^6$ and $R^{10}$ are —OH, or together form an epoxide. The oxidation can be performed using, for example, $KMnO_4$, $OsO_4$, Sharpless asymmetric dihydroxylation conditions, Sharpless asymmetric epoxidation conditions, Jacobsen's catalyst, Shi epoxidation conditions, dimethyldioxirane (DMDO), and meta-chloroperbenzoic acid (mCPBA).

The foregoing and other objects, features, and advantages of the invention will become more apparent from the following detailed description, which proceeds with reference to the accompanying figures.

DETAILED DESCRIPTION

Disclosed herein are embodiments of synthetic macrocyclic compounds ("macrocycles") and embodiments of a method for making the same. Some embodiments of the synthetic macrocycles may demonstrate biological activity, e.g., activity against immunology targets.

I. Terms and Abbreviations

The following explanations of terms and abbreviations are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. Other features of the disclosure are apparent from the following detailed description and the claims.

Unless otherwise indicated, all numbers expressing quantities of components, molecular weights, percentages, temperatures, times, and so forth, as used in the specification or claims are to be understood as being modified by the term "about." Accordingly, unless otherwise indicated, implicitly or explicitly, the numerical parameters set forth are approximations that may depend on the desired properties sought and/or limits of detection under standard test conditions/methods. When directly and explicitly distinguishing embodiments from discussed prior art, the embodiment numbers are not approximates unless the word "about" is recited.

Definitions of common terms in chemistry may be found in Richard J. Lewis, Sr. (ed.), *Hawley's Condensed Chemical Dictionary*, published by John Wiley & Sons, Inc., 1997 (ISBN 0-471-29205-2).

In order to facilitate review of the various embodiments of the disclosure, the following explanations of specific terms are provided:

Agonist: A compound that binds to a receptor or an enzyme and produces an action. For example, an agonist that binds to a cellular receptor initiates a physiological or pharmacological response characteristic of that receptor. An agonist that binds to an enzyme activates the enzyme. A receptor antagonist blocks an action of an agonist or elicits the opposite physiological or pharmacological response as an agonist for the receptor.

Aliphatic: A substantially hydrocarbon-based compound, or a radical thereof (e.g., $C_6H_{13}$, for a hexane radical), including alkanes, alkenes, alkynes, including cyclic versions thereof, and further including straight- and branched-chain arrangements, and all stereo and position isomers as well. This term also encompasses substituted aliphatic compounds, saturated aliphatic compounds, and unsaturated aliphatic compounds.

Alkenyl: Hydrocarbon groups having carbon chains containing one or more double bonds.

Alkyl: A hydrocarbon group having a saturated carbon chain. The chain may be cyclic, branched or unbranched. The term lower alkyl means the chain includes 1-10 carbon atoms. The terms alkenyl and alkynyl refer to hydrocarbon groups having carbon chains containing one or more double or triple bonds, respectively.

Alkynyl: Hydrocarbon groups having carbon chains containing one or more triple bonds.

Allyl: A hydrocarbon group with the structural formula $H_2C=CH-CH_2-$.

Allylation is a reaction that adds an allyl group to a compound and/or forms an allyl group in a compound.

Allyloxycarbonyl (Aloc, Alloc, Aoc): A functional group with the general formula:

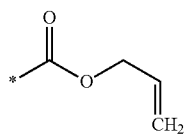

Amide: An organic functional group characterized by a carbonyl group (C=O) linked to a nitrogen atom and having the following general formula, where R, R' and R" are the same or different, and typically are selected from hydrogen, aliphatic, and aryl.

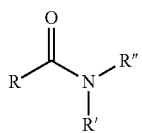

Amino Acid: An organic acid containing both a basic amino group ($-NH_2$) and an acidic carboxyl group ($-COOH$). The 20 amino acids that are protein constituents are α-amino acids, i.e., the $-NH_2$ group is attached to the carbon atom next to the $-COOH$ group.

Analog: A molecule that differs in chemical structure from a parent compound, for example a homolog (differing by an increment in the chemical structure, such as a difference in the length of an alkyl chain), a molecular fragment, a structure that differs by one or more functional groups, a change in ionization. Structural analogs are often found using quantitative structure-activity relationships (QSAR), with techniques such as those disclosed in Remington (*The Science and Practice of Pharmacology*, 21st Edition (2005), chapter 28).

Aromatic: "Aromatic" Compounds typically are unsaturated, cyclic hydrocarbons having alternate single and double bonds. Benzene, a 6-carbon ring containing three double bonds, is a typical aromatic compound.

Aryl: A substantially hydrocarbon-based aromatic compound, or a radical thereof (e.g. $C_6H_5$) as a substituent bonded to another group or groups, particularly other organic groups, and having a ring structure as exemplified by, but not limited to benzene, naphthalene, phenanthrene, anthracene, etc. This term also encompasses substituted aryl compounds.

Arylalkyl: An acyclic alkyl group in which one of the hydrogen atoms bonded to a carbon atom, typically a terminal or $sp^3$ carbon atom, is replaced with an aryl group. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylakenyl and/or arylalkynyl may be used.

Aziridine: A functional group which is a three-membered heterocycle with one amine group and two methylene groups:

Benzyloxycarbonyl: A functional group with the formula:

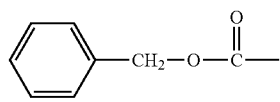

Boc (t-Boc): A tert-butyloxycarbonyl group that functions as a protecting group in synthesis, particularly peptide synthesis. Boc groups can be removed by strong acids, e.g., HCl.

Cyclic: Designates a substantially hydrocarbon, closed-ring compound, or a radical thereof. Cyclic compounds or substituents also can include one or more sites of unsaturation, but does not include aromatic compounds. One example of a cyclic compound is cyclopentane.

DCM: Dichloromethane.

Diastereomers: Optically active isomers containing two or more asymmetric carbons with differing configurations at one or more of the stereocenters and are not minor images of each other, as exemplified below:

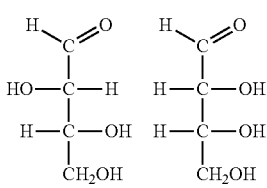

Diastereomers that differ at only one stereocenter are also known as epimers.

DMF: Dimethylformamide.

EDC: N-ethyl-N'-(3-dimethylaminopropyl)carbodiimide.

Enantiomers: Optically active isomers containing one or more asymmetric carbons that are non-superimposable mirror images of one another, as exemplified below:

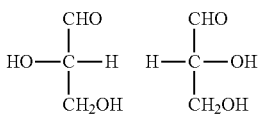

Ester: A chemical compound derived from an organic acid (general formula: $RCO_2H$) where the hydrogen of the —OH (hydroxyl) group is replaced by an aliphatic, alkyl or aryl group. A general formula for an ester derived from an organic acid is shown below:

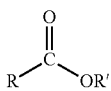

where R and R' denote virtually any group, including aliphatic, substituted aliphatic, aryl, arylalkyl, heteroaryl, etc.

E/Z isomers: Isomers that differ in the stereochemistry of a double bond. An E isomer (from entgegen, the German word for "opposite") has a trans-configuration at the double bond, in which the two groups of highest priority are on opposite sides of the double bond. A Z isomer (from zusammen, the German word for "together") has a cis-configuration at the double bond, in which the two groups of highest priority are on the same side of the double bond. The E and Z isomers of 2-butene are shown below:

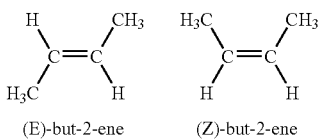

Functional group: A specific group of atoms within a molecule that is responsible for the characteristic chemical reactions of the molecule. Exemplary functional groups include, without limitation, alkane, alkene, alkyne, arene, halo (fluoro, chloro, bromo, iodo), epoxide, hydroxyl, carbonyl (ketone), aldehyde, carbonate ester, carboxylate, ether, ester, peroxy, hydroperoxy, carboxamide, amine (primary, secondary, tertiary), ammonium, imide, azide, cyanate, isocyanate, thiocyanate, nitrate, nitrite, nitrile, nitroalkane, nitroso, pyridyl, phosphate, sulfonyl, sulfide, thiol (sulfhydryl), disulfide.

HATU: O-(7-azabenzo-triazol-1-yl)-N,N,N',N'-tetramethyluronium hexafluorophosphate.

Heteroaliphatic: An aliphatic group, which contains one or more atoms other than carbon and hydrogen, such as, but not limited to, oxygen, sulfur, nitrogen, phosphorus, chlorine, fluorine, bromine, iodine, and selenium.

Heteroaryl: An aryl group, which contains one or more atoms other than carbon and hydrogen, such as, but not limited to, oxygen, sulfur, nitrogen, phosphorus, chlorine, fluorine, bromine, iodine, and selenium.

Heterocyclic: Refers to a closed-ring compound or radical thereof as a substituent bonded to another group, particularly other organic groups, where at least one atom in the ring structure is other than carbon, and typically is oxygen, sulfur and/or nitrogen.

HOBt: 1-hydroxybenzotriazole, a racemization suppressor.

Homologous or homologated series: A series of organic compounds in which each successive member has one additional —$CH_2$ group in its molecule than the preceding method. For example, methanol ($CH_3OH$), ethanol ($CH_3CH_2OH$), and propanol ($CH_3(CH_2)_2OH$) form a homologous series.

Inhibitor: A compound that blocks or suppresses the rate of a reaction. An enzyme inhibitor binds to an enzyme and decreases or completely blocks the enzyme's activity. A receptor inhibitor binds to a receptor and typically blocks the physiological or pharmacological response associated with the receptor.

Isomer: One of two or more molecules having the same number and kind of atoms, but differing in the arrangement or configuration of the atoms.

Ketone: A carbonyl-bearing substituent having a formula

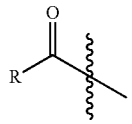

where R is virtually any group, including aliphatic, substituted aliphatic, aryl, arylalkyl, heteroaryl, etc.

Macrocycle: A cyclic macromolecule or a macromolecular cyclic portion of a molecule. More particularly, the term "macrocycle" typically refers to an organic molecule with a relatively large ring structure, such as rings containing seven or more carbon atoms.

MeOH: Methanol.

Metathesis: The reaction of two compounds to form two new compounds. Also known as double displacement or double replacement.

Nitro: A functional group with the formula —$NO_2$.

Nitroso: A functional group with the general formula —N=O.

Olefin: An unsaturated aliphatic hydrocarbon having one or more double bonds. Olefins with one double bond are alkenes; olefins with two double bonds are alkadienes.

Pharmacophore: A set of structural features in a molecule that is recognized at a receptor site and confers biological activity upon the molecule. IUPAC defines a pharmacophore as "an ensemble of steric and electronic features that is necessary to ensure the optimal supramolecular interactions with a specific biological target and to trigger (or block) its biological response." (Wermuth, C. G. et al., "Glossary of terms used in medicinal chemistry," *Pure Appl. Chem.*, 1998.)

Protecting group: A group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, Protective Groups in Organic Chemistry, 3rd Ed., 1999, John Wiley & Sons, NY and Harrison et al., Compendium of Synthetic Organic Methods, Vols. 1-8, 1971-1996, John Wiley & Sons, NY. Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, allyloxycarbonyl, 9-fluorenyl-methyloxycarbonyl ("FMOC"), nitro-veratryloxycarbonyl ("NVOC") and the like. Representative hydroxyl protecting groups include, but are not limited to, those where the hydroxyl group is either acylated or alkylated such as benzyl and trityl ethers, as well as alkyl ethers, tetrahydropyranyl ethers, trialkylsilyl ethers (e.g., TMS or TIPPS groups) and allyl ethers.

Racemization: The partial conversion by heat or chemical reaction of one isomer into a mixture of isomers. Racemization refers particularly to the conversion of enantiomers, or optically active isomers.

Ring-closing metathesis (RCM): A metathesis reaction resulting in the synthesis of a cyclic alkene. RCM typically proceeds via a Grubbs' catalyst—a transition metal carbene complex. In particular, the so-called second generation Grubbs' catalysts are particularly useful for RCM. Other suitable catalysts include the first generation Grubb's catalyst, the Grubbs-Hoveyda catalyst, and the Schrock catalyst.

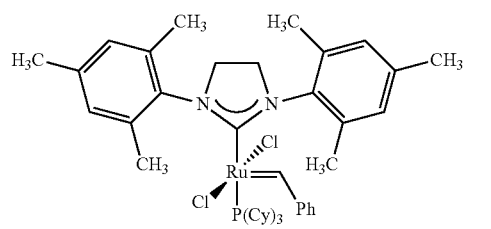

2$^{nd}$ generation Grubbs' Catalyst

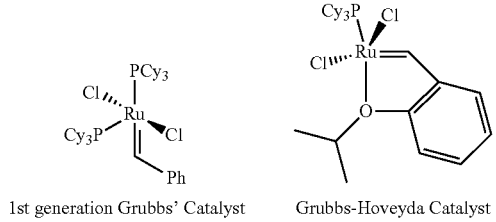

1st generation Grubbs' Catalyst    Grubbs-Hoveyda Catalyst

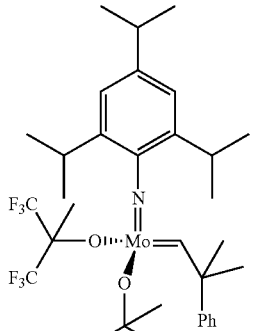

Schrock Catalyst

SAR: Structure-activity relationship.

Silyl: A functional group with the formula —SiH$_3$. This term, however, may also refer to a functional group comprising a silicon atom bonded to different functional groups, and typically having a formula

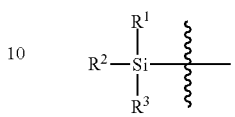

where R$_1$-R$_3$ independently are selected from various groups, including by way of example aliphatic, substituted aliphatic, cyclic aliphatic, substituted cyclic aliphatic, aryl, substituted aryl, heteroaryl, and substituted heteroaryl.

Silyl ester: A functional group with the formula:

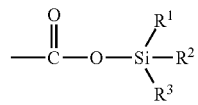

where R$_1$-R$_3$ independently are selected from various groups, including by way of example aliphatic, substituted aliphatic, cyclic aliphatic, substituted cyclic aliphatic, aryl, substituted aryl, heteroaryl, and substituted heteroaryl.

Silyl ether: A functional group with the formula:

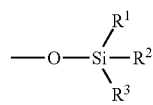

where R$_1$-R$_3$ independently are selected from various groups, including by way of example aliphatic, substituted aliphatic, cyclic aliphatic, substituted cyclic aliphatic, aryl, substituted aryl, heteroaryl, and substituted heteroaryl.

Stereoisomers: Isomers that have the same molecular formula and sequence of bonded atoms, but which differ only in the three-dimensional orientation of the atoms in space.

Substituted: A fundamental compound, such as an aryl or aliphatic compound, or a radical thereof, having coupled thereto, typically in place of a hydrogen atom, a second substituent. For example, substituted aryl compounds or substituents may have an aliphatic group coupled to the closed ring of the aryl base, such as with toluene. Again solely by way of example and without limitation, a hydrocarbon may have a substituent bonded thereto, such as one or more halogens, an aryl group, a cyclic group, a heteroaryl group or a heterocyclic group. Certain substituents recited herein are expressly indicated as being substituted, such as with "substituted aliphatic." However, a substituent that is not expressly recited as being substituted can nevertheless have one or more hydrogen atoms replaced with some other moiety, as will be understood by a person of ordinary skill in the art.

Sulfonyl: A functional group with the general formula:

where R and R' independently are selected from various groups, including by way of example aliphatic, substituted aliphatic, cyclic aliphatic, substituted cyclic aliphatic, aryl, substituted aryl, heteroaryl, and substituted heteroaryl.

Suzuki coupling: Suzuki coupling is the reaction of an aryl-, alkyl, or vinyl-boronic acid with an aryl- or vinyl-halide catalyzed by a palladium complex:

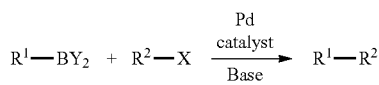

The reaction also works with boron esters and with pseudohalides (e.g., triflates—a functional group with the formula $CF_3SO_3-$). Suitable palladium catalysts include tetrakis(triphenylphosphine)palladium(0) ($Pd(PPh_3)_4$) and bis(triphenylphosphine)-palladium(II) chloride ($PdCl_2(PPh_3)_2$).

TEA: Triethylamine.

Thiol: A functional group with the formula —SH.

Thioester: A functional group with the general formula:

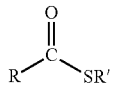

where R and R' independently are selected from various groups, including by way of example aliphatic, substituted aliphatic, cyclic aliphatic, substituted cyclic aliphatic, aryl, substituted aryl, heteroaryl, and substituted heteroaryl.

Thioether or sulfide: A functional group with the general formula: R—S—R' where R and R' independently are selected from various groups, including by way of example aliphatic, substituted aliphatic, cyclic aliphatic, substituted cyclic aliphatic, aryl, substituted aryl, heteroaryl, and substituted heteroaryl. A thioether is similar to an ether, except that it contains a sulfur atom in place of the oxygen.

II. Macrocyclic Compounds

A. Introduction

Disclosed herein are embodiments of synthetic macrocyclic compounds and embodiments of a method for making the macrocycles. A person of ordinary skill in the art will understand, as discussed in more detail herein, that the macrocycle can be formed from an acyclic precursor in a variety of ways. For certain disclosed embodiments, 17-membered macrocycles were synthesized using ring-closing metathesis. One example of a 17-membered macrocycle synthesized by an embodiment of the disclosed method is shown below:

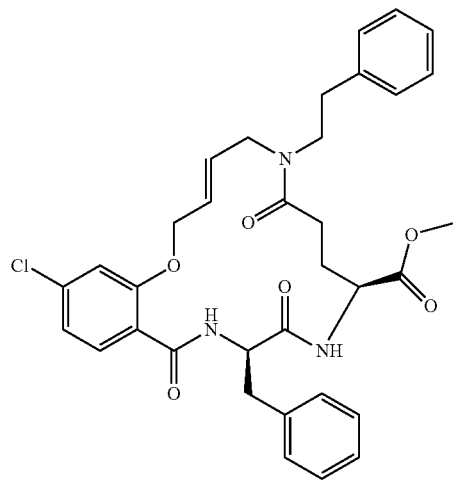 [SMILES: COC(=O)[C@@H]1CCC(=O)N(CCc2ccccc2)C/C=C/COc2cc(Cl)ccc2C(=O)N[C@H](Cc2ccccc2)C(=O)N1]

This representative compound is a 17-membered, tri-amide featuring a salicylic acid-based aromatic moiety on the left-hand side, an amino acid at the bottom, a glutamic methyl ester on the right-hand side, and an olefin at the position where the acyclic precursor was closed to form the macrocycle.

B. General Formulas

Certain disclosed macrocycles have general Formula 1

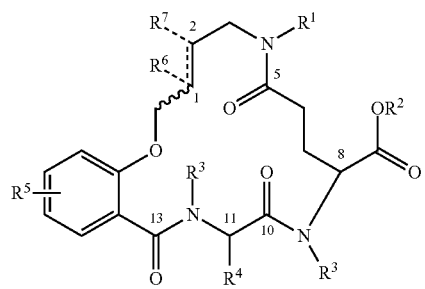

Formula 1

With reference to general Formula 1, $R^1$ is selected from hydrogen, aliphatic (alkyl, alkenyl, alkynyl), substituted aliphatic, aromatic, substituted aromatic, arylalkyl, such as benzyl, homologated benzyl, substituted arylalkyl, such as substituted benzyl, substituted homologated benzyl, benzoyl, ester, ketone, tert-butoxycarbonyl, 9H-fluoren-9-ylmethoxycarbonyl, allyloxycarbonyl, benzyloxy carbonyl, trichloroethoxycarbonyl, triphenylmethyl, and sulfonyl. $R^2$ is selected from hydrogen, aliphatic, typically alkyl, more typically lower alkyl, such as methyl, ethyl, propyl, and butyl. In certain instances $R^2$ represents a counterion, such as an inorganic or organic cation. Each $R^3$ is independently selected from hydrogen, aliphatic, such as alkyl, more typically lower alkyl, such as methyl, ethyl, propyl, and butyl, substituted aliphatic, aromatic, substituted aromatic, arylalkyl, such as benzyl, homologated benzyl, substituted arylalkyl, such as substituted benzyl, substituted homologated benzyl benzoyl, ester, ketone, tert-butoxycarbonyl, 9H-fluoren-9-ylmethoxycarbonyl, allyloxycarbonyl, benzyloxy carbonyl, trichloroethoxycarbonyl, triphenylmethyl, and sulfonyl. $R^4$ is selected from hydrogen, lower alkyl, such as methyl, —$CH(CH_3)CH_2CH_3$, —$CH_2CH(CH_3)_2$, —$(CH_2)_2SCH_3$, benzyl, substituted benzyl, 3-indole, —$CH(CH_3)_2$, —$CH_2OH$, —$CH(OH)(CH_3)$, —CH$_2$C(O)NH$_2$, —(CH$_2$)$_2$C(O)NH$_2$, —CH$_2$SH, —CH$_2$SeH, —(CH$_2$)$_3$NHC(NH$_2$$^+$)NH$_2$, —CH$_2$(imidazole), —(CH$_2$)$_4$NH$_2$, —CH$_2$C(O)OH, —(CH$_2$)$_2$C(O)OH, where R$^3$ and R$^4$ together form a 5-membered ring, and any natural or non-natural amino acid side chain. R$^5$ is selected from aliphatic, substituted aliphatic, alkoxy, particularly lower alkoxy, such as methoxy, substituted alkoxy, amine, substituted amine, amide, substituted amide, aryl, substituted aryl, aryl alkyl, substituted arylalkyl, cyclic, substituted cyclic, ester, ether, formyl, halogen, heterocyclic, substituted heterocyclic, heteroaryl, substituted heteroaryl, hydrogen, hydroxyl, ketone, substituted ketone, nitro, nitroso, protecting groups, silyl, silyl ether, silyl ester, thiol, thioether, thioester. The macrocycle can contain an optional double bond, represented by "===" The double bond geometry can be either Z or E, as indicated by the wavy bond "∿∿∿" connected to the double bond. R$^6$ and R$^7$ can be hydrogen when the double bond is present, or the macrocycle can be saturated, wherein R$^6$ and R$^7$ can be selected from aliphatic, amino, halogen, hydrogen, hydroxyl, or R$^6$ and R$^7$ together form an epoxide or aziridine. A person of ordinary skill in the art will recognize that the macrocycle can be a racemic mixture, optically active, a single diastereomer or a mixture of diastereomers.

Particular embodiments of the disclosed compounds have the following chemical structures.

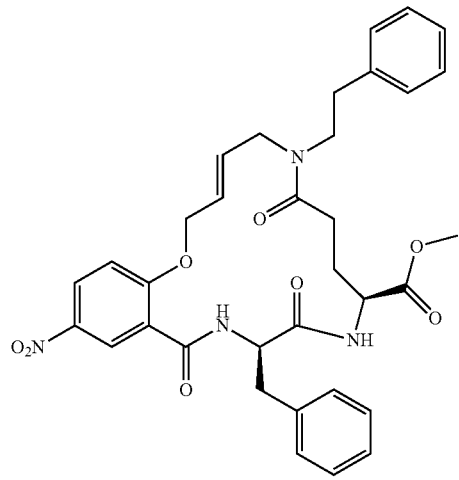

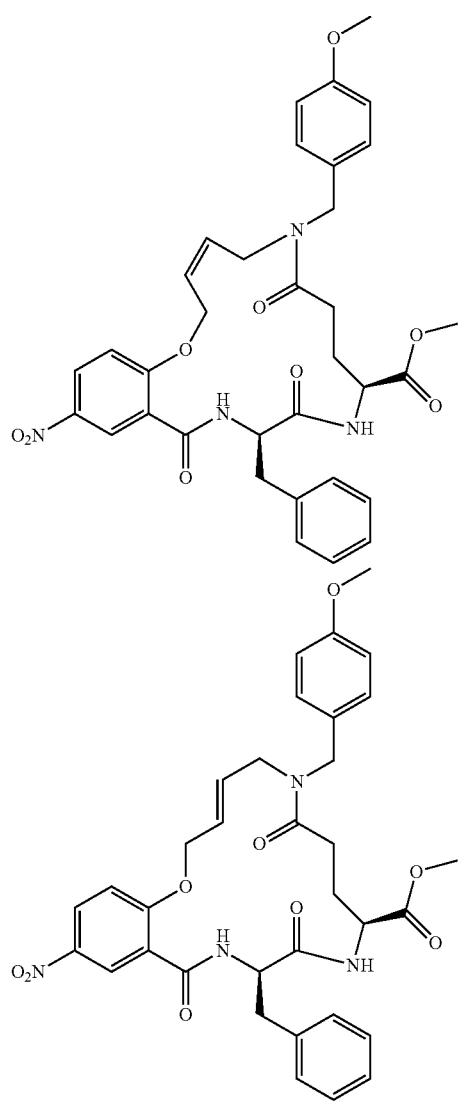

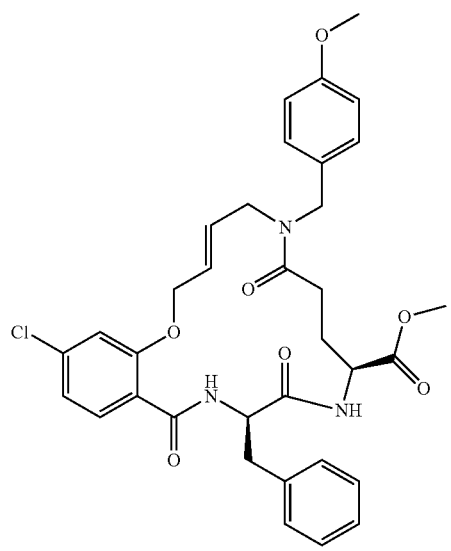

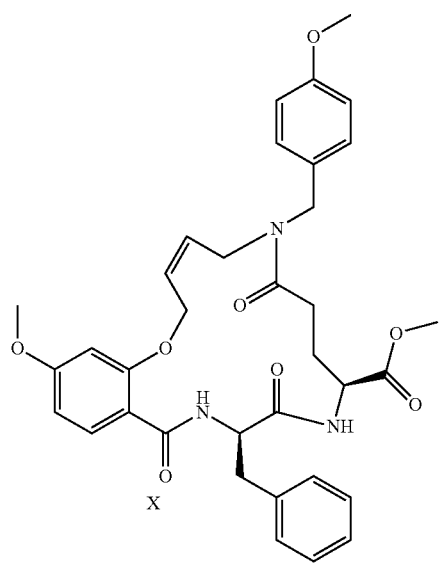

33
-continued
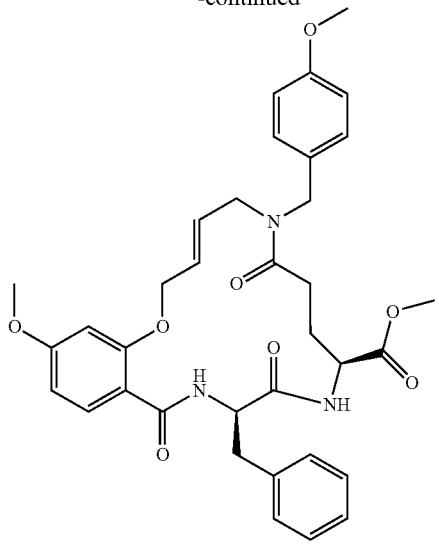
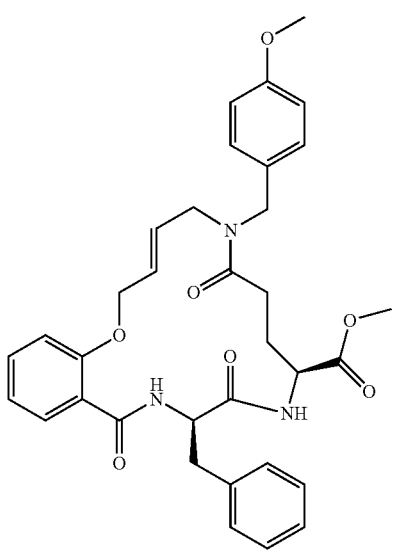
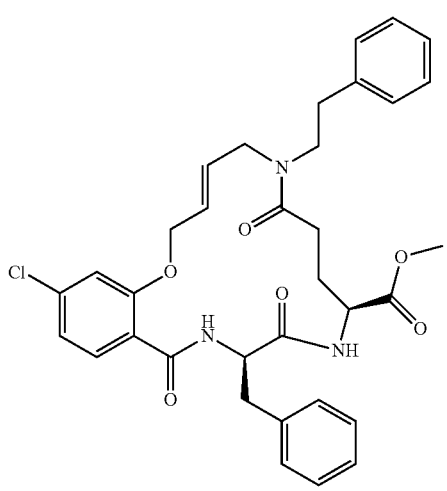
34
-continued
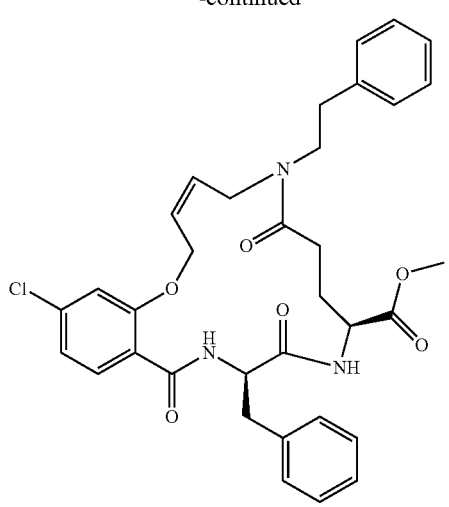
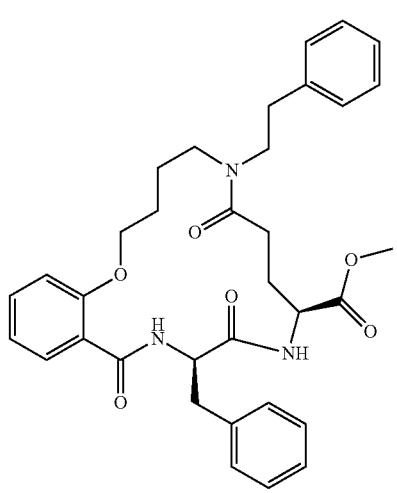
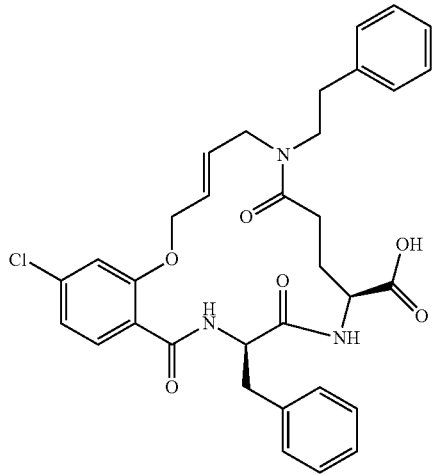

35
-continued
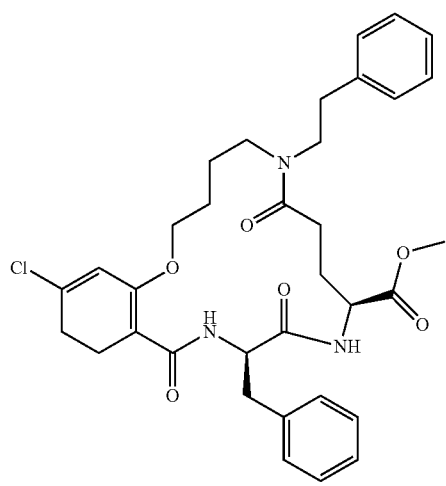
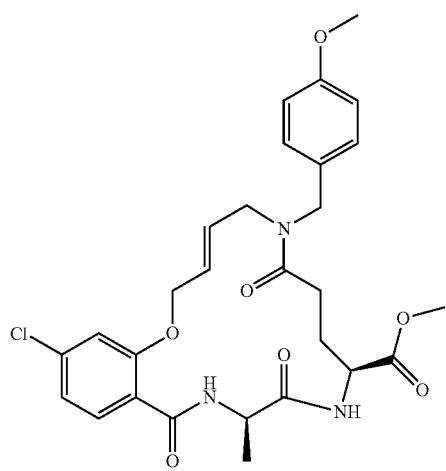
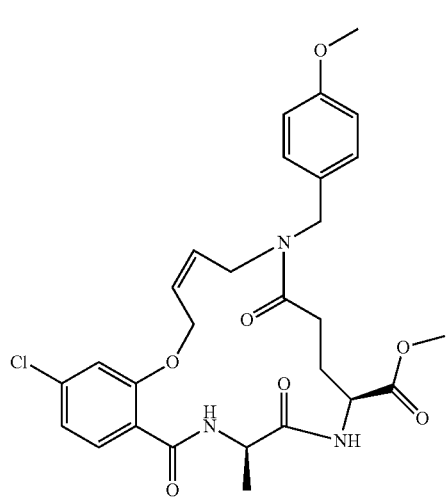
36
-continued
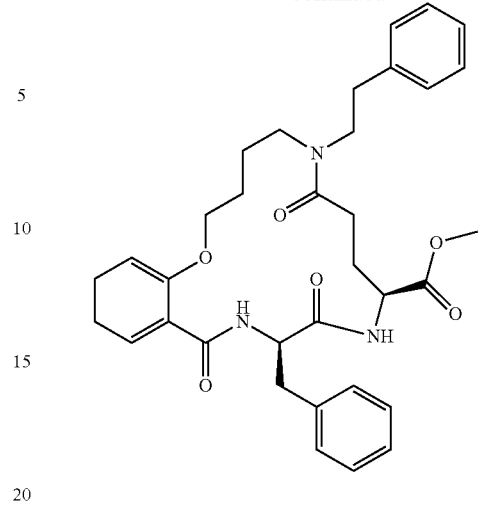
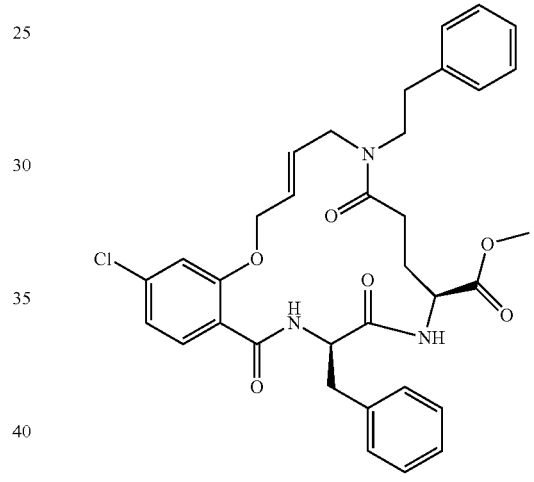
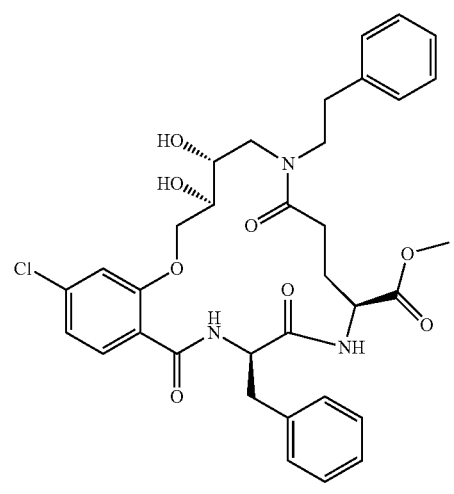

Certain embodiments concern acyclic precursors having a second general formula as follows.

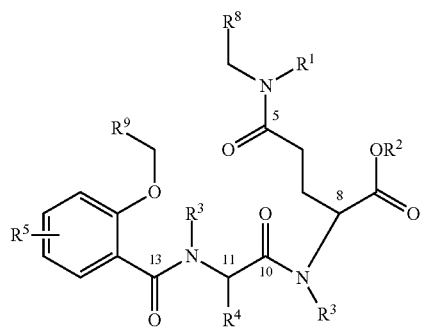

Formula 2

With reference to general Formula 2, $R^1$ is selected from hydrogen, aliphatic (alkyl, alkenyl, alkynyl), substituted aliphatic aromatic, substituted aromatic, arylalkyl, such as benzyl, and homologated benzyl, substituted arylalkyl, such as substituted benzyl, and substituted homologated benzyl, benzoyl, ester, ketone, tert-butoxycarbonyl, 9H-fluoren-9-yl-methoxycarbonyl, allyloxycarbonyl, benzyloxy carbonyl, trichloroethoxycarbonyl, triphenylmethyl, and sulfonyl. $R^2$ is selected from hydrogen, aliphatic, typically alkyl, more typically lower alkyl, such as methyl, ethyl, propyl, and butyl. Each $R^3$ is independently selected from hydrogen, aliphatic, such as alkyl, more typically lower alkyl, such as methyl, ethyl, propyl, and butyl, substituted aliphatic, aromatic, substituted aromatic, arylalkyl, such as benzyl, homologated benzyl, substituted arylalkyl, such as substituted benzyl, substituted homologated benzyl benzoyl, ester, ketone, tert-butoxycarbonyl, 9H-fluoren-9-ylmethoxycarbonyl, allyloxycarbonyl, benzyloxy carbonyl, trichloroethoxycarbonyl, triphenylmethyl, and sulfonyl. $R^4$ is selected from hydrogen, lower alkyl, such as methyl, —CH($CH_3$)$CH_2CH_3$, —$CH_2$CH($CH_3$)$_2$, —($CH_2$)$_2SCH_3$, benzyl, substituted benzyl, 3-indole, —CH($CH_3$)$_2$, —$CH_2$OH, —CH(OH)($CH_3$), —$CH_2$C(O)$NH_2$, —($CH_2$)$_2$C(O)$NH_2$, —$CH_2$SH, —$CH_2$SeH, —($CH_2$)$_3$NHC($NH_2^+$)$NH_2$, —$CH_2$(imidazole), —($CH_2$)$_4NH_2$, —$CH_2$C(O)OH, —($CH_2$)$_2$C(O)OH, where $R^3$ and $R^4$ together form a 5-membered ring, and any natural or non-natural amino acid side chain. $R^5$ is selected from aliphatic, substituted aliphatic, alkoxy, particularly lower alkoxy, such as methoxy, substituted alkoxy, amine, substituted amine, amide, substituted amide, aryl, substituted aryl, aryl alkyl, substituted aryl alkyl, cyclic, substituted cyclic, ester, ether, formyl, halogen, heterocyclic, substituted heterocyclic, heteroaryl, substituted heteroaryl, hydrogen, hydroxyl, ketone, substituted ketone, nitro, nitroso, protecting groups, silyl, silyl ether, silyl ester, thiol, thioether, thioester. $R^8$ and $R^9$ are selected from groups selected to (1) provide functionality at these positions, or precursors to such functionality, as desired in the end macrocycle, and/or (2) facilitate ring closure, as determined by the type of ring-closing reaction selected for a particular synthesis. Particular examples of suitable functional groups include, —$CR^{10}$=$CR^{11}R^{12}$ with $R^{10}$-$R^{12}$ independently selected from aliphatic, such as methyl, ethyl, propyl, and butyl, aromatic, substituted aromatic, arylalkyl, substituted arylalkyl. In other embodiments, $R^8$ and $R^9$ can be selected from —C(O)H, —$CH_2SO_2$Ph, —$CH_2PPh_3$, —$CH_2$P(O)(O$CH_2CF_3$)$_2$, —$CH_2$P(O) (OEt)$_2$, —$CH_2SO_2$-tetrazole and any other reagent capable of undergoing ring closing metathesis or olefination reactions. A person of ordinary skill in the art will recognize that the acyclic precursor can be a single diastereomer or a mixture of diastereomers.

Certain disclosed embodiments, particularly useful for ring closing metathesis, have the following chemical structures.

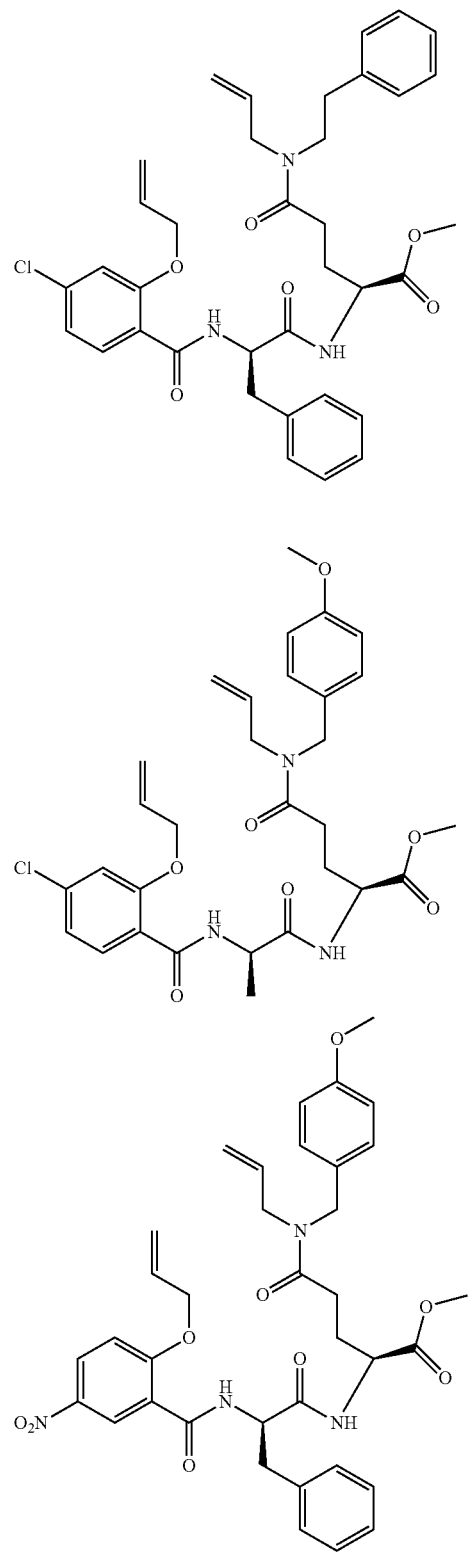

-continued

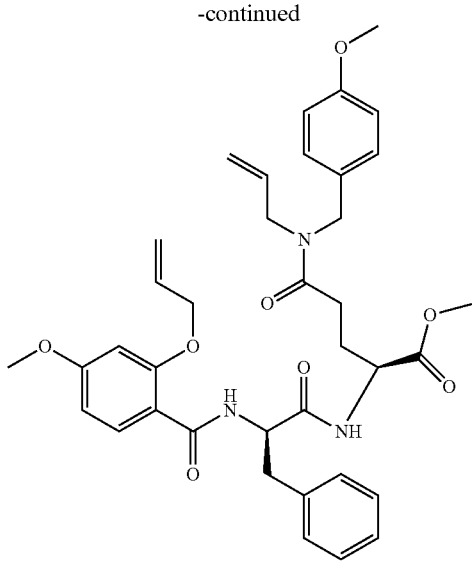

Other embodiments include the use of starting materials and reaction intermediates having the following general formulas.

Formula 3

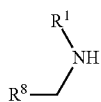

With reference to general Formula 3, $R^1$ can be selected from hydrogen, aliphatic, substituted aliphatic, alkyl, alkenyl, alkynyl, aromatic, substituted aromatic, arylalkyl, such as benzyl, homologated benzyl, substituted arylalkyl, such as substituted benzyl, benzoyl, ester, ketone, tert-butoxycarbonyl, 9H-fluoren-9-ylmethoxycarbonyl, allyloxycarbonyl, benzyloxy carbonyl, trichloroethoxycarbonyl, triphenylmethyl, and sulfonyl, and $R_8$ can be selected from —$CR^{10}$=$CR^{11}R^{12}$ with $R^{10}$-$R^{12}$ independently selected from aliphatic, such as methyl, ethyl, propyl, and butyl aromatic, substituted aromatic, arylalkyl, substituted arylalkyl. In other embodiments, $R^8$ can be selected from —C(O)H, —$CH_2SO_2Ph$, —$CH_2PPh_3$, —$CH_2P(O)(OCH_2CF_3)_2$, —$CH_2P(O)(OEt)_2$, —$CH_2SO_2$-tetrazole and any other reagent capable of undergoing ring closing metathesis or olefination reactions.

Particular embodiments have the chemical structures illustrated below.

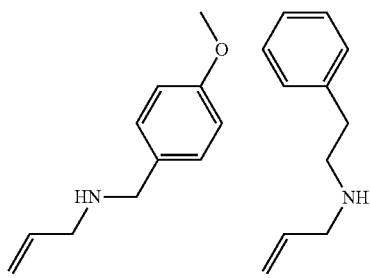

Certain embodiments utilize the following general formula.

Formula 4

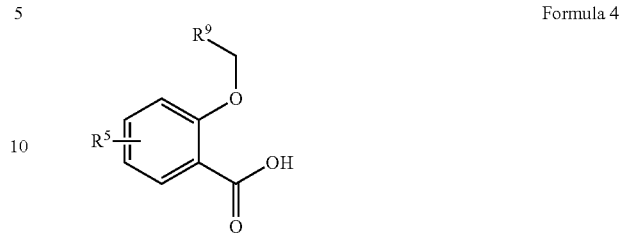

With reference to general Formula 4, $R^5$ is selected from, aliphatic, substituted aliphatic, alkoxy, particularly lower alkoxy, such as methoxy, substituted alkoxy, amine, substituted amine, amide, substituted amide, aryl, substituted aryl, arylalkyl, substituted arylalkyl, cyclic, substituted cyclic, ester, ether, formyl, halogen, heterocyclic, substituted heterocyclic, heteroaryl, substituted heteroaryl, hydrogen, hydroxyl, ketone, substituted ketone, nitro, nitroso, protecting groups, silyl, silyl ether, silyl ester, thiol, thioether, and thioester. $R^9$ is selected from —$CR^{10}$=$CR^{11}R^{12}$ with $R^{10}$-$R^{12}$ independently selected from aliphatic, such as methyl, ethyl, propyl, and butyl, aromatic, substituted aromatic, arylalkyl, substituted arylalkyl. In other embodiments, $R^9$ can be selected from —C(O)H, —$CH_2SO_2Ph$, —$CH_2PPh_3$, —$CH_2P(O)(OCH_2CF_3)_2$, —$CH_2P(O)(OEt)_2$, —$CH_2SO_2$-tetrazole and any other reagent capable of undergoing a ring closing reaction, such as metathesis or other olefin-forming reactions.

Particular embodiments have the chemical structures illustrated below.

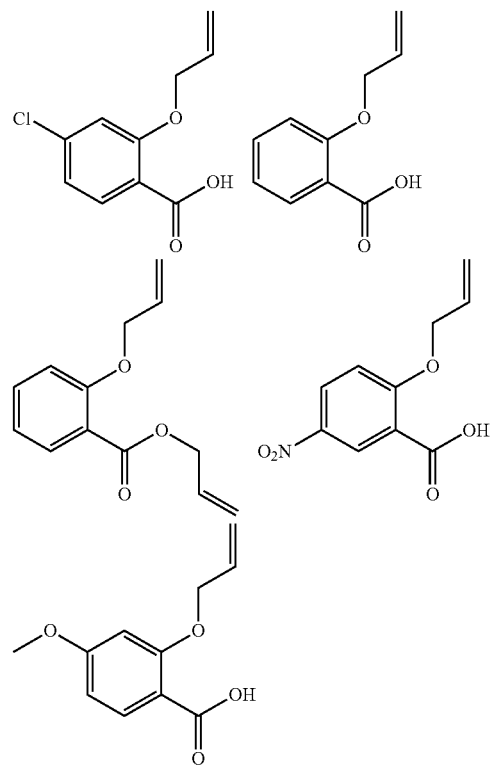

Certain embodiments utilize the following general formula.

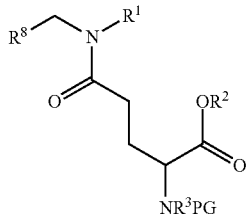

Formula 5

With reference to general Formula 5, R[1] is selected from hydrogen, aliphatic, substituted aliphatic, alkyl, alkenyl, alkynyl, aromatic, substituted aromatic, arylalkyl, such as benzyl, homologated benzyl, substituted arylalkyl, such as substituted benzyl, benzoyl, ester, ketone, tert-butoxycarbonyl, 9H-fluoren-9-ylmethoxycarbonyl, allyloxycarbonyl, benzyloxy carbonyl, trichloroethoxycarbonyl, triphenylmethyl, and sulfonyl. R[2] is selected from hydrogen, aliphatic, such as alkyl, more typically lower alkyl, such as methyl, ethyl, propyl, and butyl, and substituted aliphatic. R[3] is selected from hydrogen, aliphatic, such as alkyl, more typically lower alkyl, such as methyl, ethyl, propyl, and butyl, substituted aliphatic, aromatic, substituted aromatic, arylalkyl, such as benzyl, homologated benzyl, substituted arylalkyl, such as substituted benzyl, benzoyl, ester, ketone. R[8] is selected from —CR[10]=CR[11]R[12] with R[10]-R[12] independently selected from aliphatic, such as methyl, ethyl, propyl, and butyl, aromatic, substituted aromatic, arylalkyl, substituted arylalkyl. In other embodiments, R[8] can be selected from —C(O)H, —CH$_2$SO$_2$Ph, —CH$_2$PPh$_3$, —CH$_2$P(O)(OCH$_2$CF$_3$)$_2$, —CH$_2$P(O) (OEt)$_2$, —CH$_2$SO$_2$-tetrazole and any other reagent capable of undergoing ring closing metathesis or olefination reactions. PG is selected from arylalkyl, such as benzyl, homologated benzyl, substituted arylalkyl, such as substituted benzyl, substituted homologated benzyl, benzoyl, ester, ketone, tert-butoxycarbonyl, 9H-fluoren-9-ylmethoxycarbonyl, allyloxycarbonyl, benzyloxy carbonyl, trichloroethoxycarbonyl, triphenylmethyl, and sulfonyl. A person of ordinary skill in the art will recognize that compounds having general Formula 5 can be a single enantiomer (either R or S), or a mixture of R and S enantiomers.

Particular embodiments have the chemical structures illustrated below.

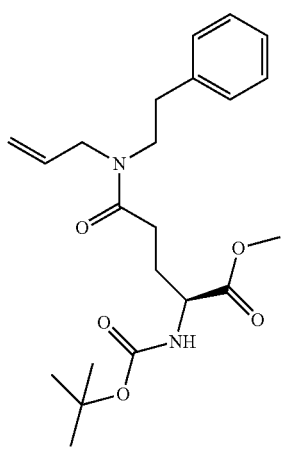

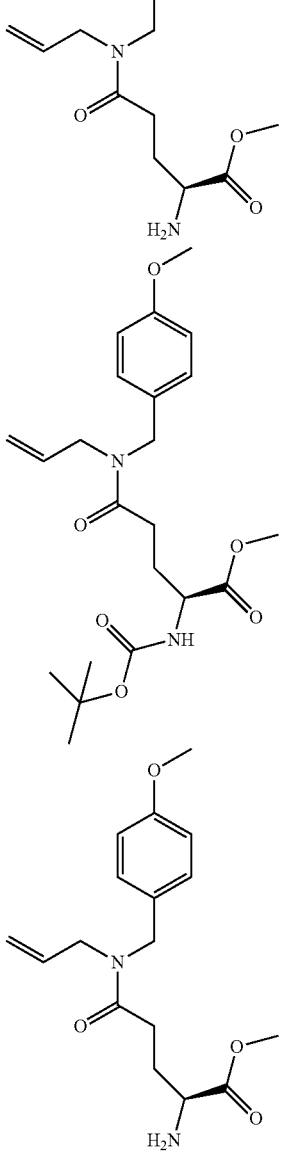

Certain embodiments utilize the following general formula.

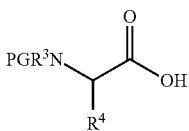

Formula 6

With reference to general Formula 6, R[3] can be selected from hydrogen, aliphatic, such as alkyl, more typically lower alkyl, such as methyl, ethyl, propyl, and butyl, substituted aliphatic, aromatic, substituted aromatic, arylalkyl, such as benzyl, homologated benzyl, substituted arylalkyl, such as substituted benzyl, substituted homologated benzyl, benzoyl, ester, ketone. PG can be selected from arylalkyl, such as benzyl, homologated benzyl, substituted arylalkyl, such as substituted benzyl, benzoyl, ester, ketone, tert-butoxycarbonyl, 9H-fluoren-9-ylmethoxycarbonyl, allyloxycarbonyl, benzyloxy carbonyl, trichloroethoxycarbonyl, triphenylmethyl, and sulfonyl. $R^4$ can be selected from hydrogen, methyl, —CH(CH$_3$)CH$_2$CH$_3$, —CH$_2$CH(CH$_3$)$_2$, —(CH$_2$)$_2$SCH$_3$, benzyl, substituted benzyl, 3-indole, —CH(CH$_3$)$_2$, —CH$_2$OH, —CH(OH)(CH$_3$), —CH$_2$C(O)NH$_2$, —(CH$_2$)$_2$C(O)NH$_2$, —CH$_2$SH, —CH$_2$SeH, —(CH$_2$)$_3$NHC(NH$_2{}^+$)NH$_2$, —CH$_2$(imidazole), —(CH$_2$)$_4$NH$_2$, —CH$_2$C(O)OH, —(CH$_2$)$_2$C(O)OH, and any unnatural amino acid side chain. In certain embodiments, $R_3$ and $R_4$ individually are or together form a 5-membered ring, and any natural or non-natural amino acid side chain. A person of ordinary skill in the art will recognize that general Formula 6 can be a single enantiomer (either R or S), or a mixture of R and S enantiomers.

Particular embodiments have the chemical structures illustrated below.

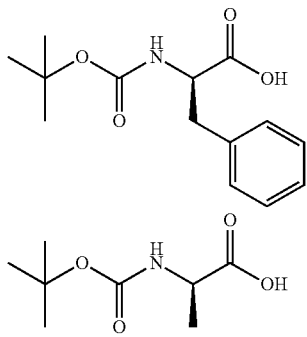

Certain embodiments utilize the following general formula.

Formula 7

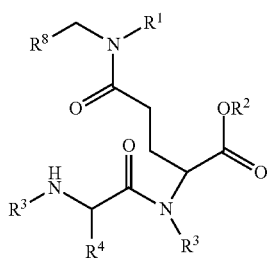

With reference to Formula 7, $R^1$ is selected from hydrogen, aliphatic, substituted aliphatic, aromatic, substituted aromatic, arylalkyl, such as benzyl, homologated benzyl, substituted arylalkyl, such as substituted benzyl, substituted homologated benzyl, benzoyl, ester, ketone, tert-butoxycarbonyl, 9H-fluoren-9-ylmethoxycarbonyl, allyloxycarbonyl, benzyloxy carbonyl, trichloroethoxycarbonyl, triphenylmethyl, and sulfonyl. $R^2$ is selected from hydrogen, aliphatic, such as alkyl, more typically lower alkyl, such as methyl, ethyl, propyl, and butyl. Each $R^3$ is independently selected from hydrogen, aliphatic, such as alkyl, more typically lower alkyl, such as methyl, ethyl, propyl, and butyl, substituted aliphatic, aromatic, substituted aromatic, arylalkyl, such as benzyl, homologated benzyl, substituted arylalkyl, such as substituted benzyl, benzoyl, ester, and ketone. $R^4$ is selected from hydrogen, methyl, —CH(CH$_3$)CH$_2$CH$_3$, —CH$_2$CH(CH$_3$)$_2$, —(CH$_2$)$_2$SCH$_3$, -benzyl, -substituted benzyl, -3-indole, —CH(CH$_3$)$_2$, —CH$_2$OH, —CH(OH)(CH$_3$), —CH$_2$C(O)NH$_2$, —(CH$_2$)$_2$C(O)NH$_2$, —CH$_2$SH, —CH$_2$SeH, —(CH$_2$)$_3$NHC(NH$_2{}^+$)NH$_2$, —CH$_2$(imidazole), —(CH$_2$)$_4$NH$_2$, —CH$_2$C(O)OH, —(CH$_2$)$_2$C(O)OH, and any unnatural amino acid side chain. In certain embodiments, $R_3$ and $R_4$ individually are or together form a 5-membered ring, and any natural or non-natural amino acid side chain. $R^8$ is selected from —CR$^{10}$=CR$^{11}$R$^{12}$ with $R^{10}$-$R^{12}$ independently selected from aliphatic, such as methyl, ethyl, propyl, and butyl aromatic, substituted aromatic, arylalkyl, substituted arylalkyl. In other embodiments, $R^8$ is selected from —C(O)H, —CH$_2$SO$_2$Ph, —CH$_2$PPh$_3$, —CH$_2$P(O)(OCH$_2$CF$_3$)$_2$, —CH$_2$P(O)(OEt)$_2$, —CH$_2$SO$_2$-tetrazole and any other reagent capable of undergoing ring closing, such as by metathesis or other olefin-forming reactions. A person of ordinary skill in the art will recognize that the acyclic precursor can be a single diastereomer or a mixture of diastereomers.

Particular embodiments have the chemical structures illustrated below.

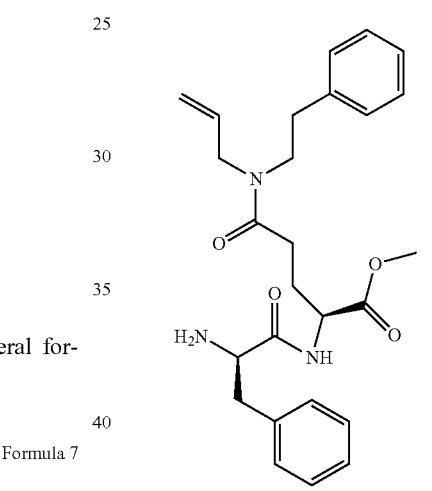

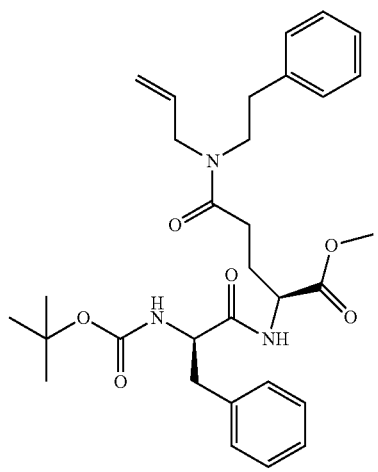

-continued

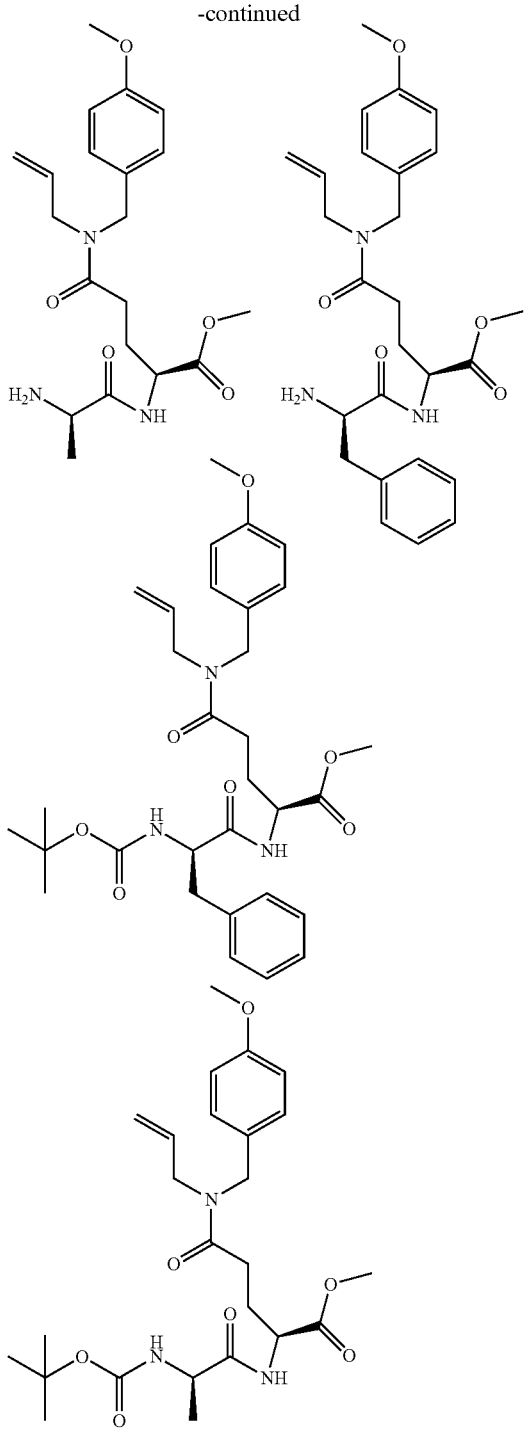

Certain embodiments use the following formula

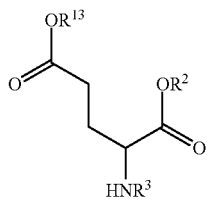

Formula 8

With reference to Formula 8, $R^2$ is selected from hydrogen, aliphatic, such as alkyl, more typically lower alkyl, such as methyl, ethyl, propyl, and butyl. Each $R^3$ is independently selected from hydrogen, aliphatic, such as alkyl, more typically lower alkyl, such as methyl, ethyl, propyl, and butyl, substituted aliphatic, aromatic, substituted aromatic, arylalkyl, such as benzyl, homologated benzyl, substituted arylalkyl, such as substituted benzyl, benzoyl, ester, and ketone. $R^{13}$ is selected from hydrogen or acid protecting groups, such as, but not limited to aliphatic, heteroaliphatic, aryl, heteroaryl, and silyl. Other potential protecting groups can be found in "Greene's Protective Groups in Organic Synthesis": Wiley-Interscience; 4th Edition (Oct. 30, 2006), which we herein incorporate by reference. A person of ordinary skill in the art will recognize that the acyclic precursor can be a single diastereomer or a mixture of diastereomers.

Certain embodiments have the following formula

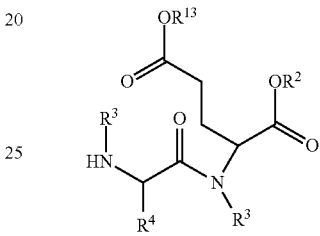

Formula 9

With reference to Formula 9, $R^2$ is selected from hydrogen, aliphatic, such as alkyl, more typically lower alkyl, such as methyl, ethyl, propyl, and butyl. Each $R^3$ is independently s selected from hydrogen, aliphatic, such as alkyl, more typically lower alkyl, such as methyl, ethyl, propyl, and butyl, substituted aliphatic, aromatic, substituted aromatic, arylalkyl, such as benzyl, homologated benzyl, substituted arylalkyl, such as substituted benzyl, benzoyl, ester, and ketone. $R^4$ is selected from hydrogen, methyl, —CH(CH$_3$)CH$_2$CH$_3$, —CH$_2$CH(CH$_3$)$_2$, —(CH$_2$)$_2$SCH$_3$, -benzyl, -substituted benzyl, -3-indole, —CH(CH$_3$)$_2$, —CH$_2$OH, —CH(OH)(CH$_3$), —CH$_2$C(O)NH$_2$, —(CH$_2$)$_2$C(O)NH$_2$, —CH$_2$SH, —CH$_2$SeH, —(CH$_2$)$_3$NHC(NH$_2$$^+$)NH$_2$, —CH$_2$(imidazole), —(CH$_2$)$_4$NH$_2$, —CH$_2$C(O)OH, —(CH$_2$)$_2$C(O)OH, and any unnatural amino acid side chain. In certain embodiments, $R_3$ and $R_4$ individually are or together form a 5-membered ring, and any natural or non-natural amino acid side chain. $R^{13}$ is selected from hydrogen or acid protecting groups, such as, but not limited to aliphatic, heteroaliphatic, aryl, heteroaryl, and silyl. A person of ordinary skill in the art will recognize that the acyclic precursor can be a single diastereomer or a mixture of diastereomers.

Other embodiments have the following formula

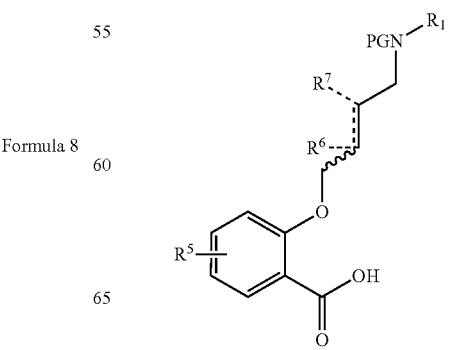

Formula 10

With reference to Formula 10, $R^1$ is selected from hydrogen, aliphatic, substituted aliphatic, aromatic, substituted aromatic, arylalkyl, such as benzyl, homologated benzyl, substituted arylalkyl, such as substituted benzyl, substituted homologated benzyl, benzoyl, ester, ketone, tert-butoxycarbonyl, 9H-fluoren-9-ylmethoxycarbonyl, allyloxycarbonyl, benzyloxy carbonyl, trichloroethoxycarbonyl, triphenylmethyl, and sulfonyl. $R^2$ is selected from hydrogen, aliphatic, such as alkyl, more typically lower alkyl, such as methyl, ethyl, propyl, and butyl. PG is selected from arylalkyl, such as benzyl, homologated benzyl, substituted arylalkyl, such as substituted benzyl, substituted homologated benzyl, benzoyl, ester, ketone, tert-butoxycarbonyl, 9H-fluoren-9-ylmethoxycarbonyl, allyloxycarbonyl, benzyloxy carbonyl, trichloroethoxycarbonyl, triphenylmethyl, and sulfonyl. $R^5$ is selected from aliphatic, substituted aliphatic, alkoxy, particularly lower alkoxy, such as methoxy, substituted alkoxy, amine, substituted amine, amide, substituted amide, aryl, substituted aryl, arylalkyl, substituted arylalkyl, cyclic, substituted cyclic, ester, ether, formyl, halogen, heterocyclic, substituted heterocyclic, heteroaryl, substituted heteroaryl, hydrogen, hydroxyl, ketone, substituted ketone, nitro, nitroso, protecting groups, silyl, silyl ether, silyl ester, thiol, thioether, and thioester. The intermediate can contain an optional double bond, represented by "===." The double bond geometry can be either Z or E, as indicated by the wavy bond "⌇⌇⌇" connected to the double bond. $R^6$ and/or $R^7$ can be hydrogen when the double bond is present, or the intermediate can be saturated, wherein $R^6$ and $R^7$ can be selected from aliphatic, amino, halogen, hydrogen, hydroxyl, or $R^6$ and $R^7$ together form an epoxide or aziridine. A person of ordinary skill in the art will recognize that the acyclic precursor can be a single diastereomer or a mixture of diastereomers.

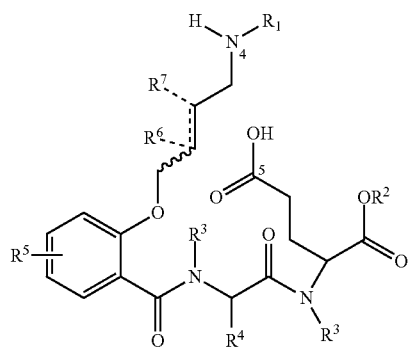

Formula 11

With reference to general Formula 11, $R^1$ is selected from hydrogen, aliphatic (alkyl, alkenyl, alkynyl), substituted aliphatic, aromatic, substituted aromatic, arylalkyl, such as benzyl, and homologated benzyl, substituted arylalkyl, such as substituted benzyl, and substituted homologated benzyl, benzoyl, ester, ketone, tert-butoxycarbonyl, 9H-fluoren-9-ylmethoxycarbonyl, allyloxycarbonyl, benzyloxy carbonyl, trichloroethoxycarbonyl, triphenylmethyl, and sulfonyl. $R^2$ is selected from hydrogen, aliphatic, typically alkyl, more typically lower alkyl, such as methyl, ethyl, propyl, and butyl. Each $R^3$ is independently selected from hydrogen, aliphatic, such as alkyl, more typically lower alkyl, such as methyl, ethyl, propyl, and butyl, substituted aliphatic, aromatic, substituted aromatic, arylalkyl, such as benzyl, homologated benzyl, substituted arylalkyl, such as substituted benzyl, substituted homologated benzyl, benzoyl, ester, ketone, tert-butoxycarbonyl, 9H-fluoren-9-ylmethoxycarbonyl, allyloxy-carbonyl, benzyloxy carbonyl, trichloroethoxycarbonyl, triphenylmethyl, and sulfonyl. $R^4$ is selected from hydrogen, lower alkyl, such as methyl, $-CH(CH_3)CH_2CH_3$, $-CH_2CH(CH_3)_2$, $-(CH_2)_2SCH_3$, benzyl, substituted benzyl, 3-indole, $-CH(CH_3)_2$, $-CH_2OH$, $-CH(OH)(CH_3)$, $-CH_2C(O)NH_2$, $-(CH_2)_2C(O)NH_2$, $-CH_2SH$, $-CH_2SeH$, $-(CH_2)_3NHC(NH_2^+)NH_2$, $-CH_2(imidazole)$, $-(CH_2)_4NH_2$, $-CH_2C(O)OH$, or $-(CH_2)_2C(O)OH$. In some embodiments, $R_3$ and $R_4$ individually are or together form a 5-membered ring, and any natural or non-natural amino acid side chain. $R^5$ is selected from aliphatic, substituted aliphatic, alkoxy, particularly lower alkoxy, such as methoxy, substituted alkoxy, amine, substituted amine, amide, substituted amide, aryl, substituted aryl, aryl alkyl, substituted aryl alkyl, cyclic, substituted cyclic, ester, ether, formyl, halogen, heterocyclic, substituted heterocyclic, heteroaryl, substituted heteroaryl, hydrogen, hydroxyl, ketone, substituted ketone, nitro, nitroso, protecting groups, silyl, silyl ether, silyl ester, thiol, thioether, thioester. The acyclic precursor can contain an optional double bond, represented by "===." The double bond geometry can be either Z or E, as indicated by the wavy bond "⌇⌇⌇" connected to the double bond. $R^6$ and/or $R^7$ can be hydrogen when the double bond is present, or the acyclic precursor can be saturated, wherein $R^6$ and $R^7$ can be selected from aliphatic, amino, halogen, hydrogen, hydroxyl, or $R^6$ and $R^7$ together form an epoxide or aziridine. A person of ordinary skill in the art will recognize that the acyclic precursor can be a single diastereomer or a mixture of diastereomers.

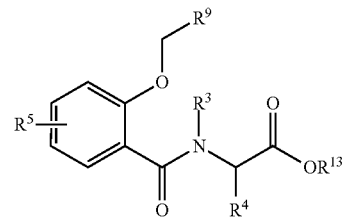

Formula 12

With reference to general Formula 12, $R^3$ is selected from hydrogen, aliphatic, such as alkyl, more typically lower alkyl, such as methyl, ethyl, propyl, and butyl, substituted aliphatic, aromatic, substituted aromatic, arylalkyl, such as benzyl, homologated benzyl, substituted arylalkyl, such as substituted benzyl, substituted homologated benzyl benzoyl, ester, ketone, tert-butoxycarbonyl, 9H-fluoren-9-ylmethoxycarbonyl, allyloxycarbonyl, benzyloxy carbonyl, trichloroethoxycarbonyl, triphenylmethyl, and sulfonyl. $R^4$ is selected from hydrogen, lower alkyl, such as methyl, $-CH(CH_3)CH_2CH_3$, $-CH_2CH(CH_3)_2$, $-(CH_2)_2SCH_3$, benzyl, substituted benzyl, 3-indole, $-CH(CH_3)_2$, $-CH_2OH$, $-CH(OH)(CH_3)$, $-CH_2C(O)NH_2$, $-(CH_2)_2C(O)NH_2$, $-CH_2SH$, $-CH_2SeH$, $-(CH_2)_3NHC(NH_2^+)NH_2$, $-CH_2(imidazole)$, $-(CH_2)_4NH_2$, $-CH_2C(O)OH$, or $-(CH_2)_2C(O)OH$. In some embodiments, $R_3$ and $R_4$ individually are or together form a 5-membered ring, and any natural or non-natural amino acid side chain. $R^5$ is selected from, aliphatic, substituted aliphatic, alkoxy, particularly lower alkoxy, such as methoxy, substituted alkoxy, amine, substituted amine, amide, substituted amide, aryl, substituted aryl, arylalkyl, substituted arylalkyl, cyclic, substituted cyclic, ester, ether, formyl, halogen, heterocyclic, substituted heterocyclic, heteroaryl, substituted heteroaryl, hydrogen, hydroxyl, ketone, substituted ketone, nitro, nitroso, protecting groups, silyl, silyl ether, silyl ester, thiol, thioether, and thioester. $R^9$ is selected from —CR$^{10}$=CR$^{11}$R$^{12}$ with $R^{10}$-$R^{12}$ independently selected from aliphatic, such as methyl, ethyl, propyl, and butyl aromatic, substituted aromatic, arylalkyl, substituted arylalkyl. In other embodiments, $R^9$ can be selected from —C(O)H, —CH$_2$SO$_2$Ph, —CH$_2$PPh$_3$, —CH$_2$P(O)(OCH$_2$CF$_3$)$_2$, —CH$_2$P(O)(OEt)$_2$, —CH$_2$SO$_2$-tetrazole and any other reagent capable of undergoing a ring closing reaction, such as metathesis or other olefin-forming reactions. $R^{13}$ is selected from hydrogen or acid protecting groups, such as, but not limited to aliphatic, heteroaliphatic, aryl, heteroaryl, and silyl.

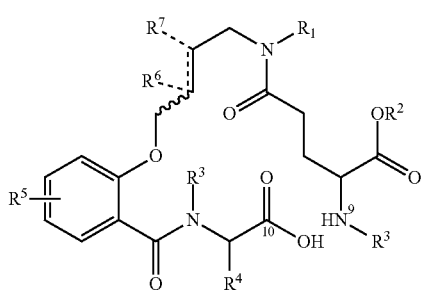

Formula 13

With reference to general Formula 13, $R^1$ is selected from hydrogen, aliphatic (alkyl, alkenyl, alkynyl), substituted aliphatic aromatic, substituted aromatic, arylalkyl, such as benzyl, and homologated benzyl, substituted arylalkyl, such as substituted benzyl, and substituted homologated benzyl, benzoyl, ester, ketone, tert-butoxycarbonyl, 9H-fluoren-9-ylmethoxycarbonyl, allyloxycarbonyl, benzyloxy carbonyl, trichloroethoxycarbonyl, triphenylmethyl, and sulfonyl. $R^2$ is selected from hydrogen, aliphatic, typically alkyl, more typically lower alkyl, such as methyl, ethyl, propyl, and butyl. Each $R^3$ is independently selected from hydrogen, aliphatic, such as alkyl, more typically lower alkyl, such as methyl, ethyl, propyl, and butyl, substituted aliphatic, aromatic, substituted aromatic, arylalkyl, such as benzyl, homologated benzyl, substituted arylalkyl, such as substituted benzyl, substituted homologated benzyl benzoyl, ester, ketone, tert-butoxycarbonyl, 9H-fluoren-9-ylmethoxycarbonyl, allyloxycarbonyl, benzyloxy carbonyl, trichloroethoxycarbonyl, triphenylmethyl, and sulfonyl. $R^4$ is selected from hydrogen, lower alkyl, such as methyl, —CH(CH$_3$)CH$_2$CH$_3$, —CH$_2$CH(CH$_3$)$_2$, —(CH$_2$)$_2$SCH$_3$, benzyl, substituted benzyl, 3-indole, —CH(CH$_3$)$_2$, —CH$_2$OH, —CH(OH)(CH$_3$), —CH$_2$C(O)NH$_2$, —(CH$_2$)$_2$C(O)NH$_2$, —CH$_2$SH, —CH$_2$SeH, —(CH$_2$)$_3$NHC(NH$_2^+$)NH$_2$, —CH$_2$(imidazole), —(CH$_2$)$_4$NH$_2$, —CH$_2$C(O)OH, or —(CH$_2$)$_2$C(O)OH. In some embodiments, $R_3$ and $R_4$ individually are or together form a 5-membered ring, and any natural or non-natural amino acid side chain. $R^5$ is selected from aliphatic, substituted aliphatic, alkoxy, particularly lower alkoxy, such as methoxy, substituted alkoxy, amine, substituted amine, amide, substituted amide, aryl, substituted aryl, aryl alkyl, substituted aryl alkyl, cyclic, substituted cyclic, ester, ether, formyl, halogen, heterocyclic, substituted heterocyclic, heteroaryl, substituted heteroaryl, hydrogen, hydroxyl, ketone, substituted ketone, nitro, nitroso, protecting groups, silyl, silyl ether, silyl ester, thiol, thioether, thioester. The acyclic precursor can contain an optional double bond, represented by "====" The double bond geometry can be either Z or E, as indicated by the wavy bond "∿∿∿" connected to the double bond. $R^6$ and $R^7$ can be hydrogen when the double bond is present, or the acyclic precursor can be saturated, wherein $R^6$ and $R^7$ can be selected from aliphatic, amino, halogen, hydrogen, hydroxyl, or $R^6$ and $R^7$ together form an epoxide or aziridine. A person of ordinary skill in the art will recognize that the acyclic precursor can be a single diastereomer or a mixture of diastereomers.

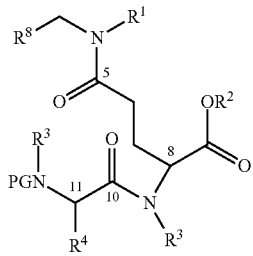

Formula 14

With reference to general Formula 14, $R^1$ is selected from hydrogen, aliphatic (alkyl, alkenyl, alkynyl), substituted aliphatic aromatic, substituted aromatic, arylalkyl, such as benzyl, and homologated benzyl, substituted arylalkyl, such as substituted benzyl, and substituted homologated benzyl, benzoyl, ester, ketone, tert-butoxycarbonyl, 9H-fluoren-9-ylmethoxycarbonyl, allyloxycarbonyl, benzyloxy carbonyl, trichloroethoxycarbonyl, triphenylmethyl, and sulfonyl. $R^2$ is selected from hydrogen, aliphatic, typically alkyl, more typically lower alkyl, such as methyl, ethyl, propyl, and butyl. Each $R^3$ is independently selected from hydrogen, aliphatic, such as alkyl, more typically lower alkyl, such as methyl, ethyl, propyl, and butyl, substituted aliphatic, aromatic, substituted aromatic, arylalkyl, such as benzyl, homologated benzyl, substituted arylalkyl, such as substituted benzyl, substituted homologated benzyl benzoyl, ester, ketone, tert-butoxycarbonyl, 9H-fluoren-9-ylmethoxycarbonyl, allyloxycarbonyl, benzyloxy carbonyl, trichloroethoxycarbonyl, triphenylmethyl, and sulfonyl. $R^4$ is selected from hydrogen, lower alkyl, such as methyl, —CH(CH$_3$)CH$_2$CH$_3$, —CH$_2$CH(CH$_3$)$_2$, —(CH$_2$)$_2$SCH$_3$, benzyl, substituted benzyl, 3-indole, —CH(CH$_3$)$_2$, —CH$_2$OH, —CH(OH)(CH$_3$), —CH$_2$C(O)NH$_2$, —(CH$_2$)$_2$C(O)NH$_2$, —CH$_2$SH, —CH$_2$SeH, —(CH$_2$)$_3$NHC(NH$_2^+$)NH$_2$, —CH$_2$(imidazole), —(CH$_2$)$_4$NH$_2$, —CH$_2$C(O)OH, or —(CH$_2$)$_2$C(O)OH. In some embodiments, $R_3$ and $R_4$ individually are or together form a 5-membered ring, and any natural or non-natural amino acid side chain. $R_8$ can be selected from —CR$^{10}$=CR$^{11}$R$^{12}$ with $R^{10}$-$R^{12}$ independently selected from aliphatic, such as methyl, ethyl, propyl, and butyl aromatic, substituted aromatic, arylalkyl, substituted arylalkyl. In other embodiments, $R^8$ can be selected from —C(O)H, —CH$_2$SO$_2$Ph, —CH$_2$PPh$_3$, —CH$_2$P(O)(OCH$_2$CF$_3$)$_2$, —CH$_2$P(O)(OEt)$_2$, —CH$_2$SO$_2$-tetrazole and any other reagent capable of undergoing ring closing metathesis or olefination reactions. PG is selected from arylalkyl, such as benzyl, homologated benzyl, substituted arylalkyl, such as substituted benzyl, substituted homologated benzyl, benzoyl, ester, ketone, tert-butoxycarbonyl, 9H-fluoren-9-ylmethoxycarbonyl, allyloxycarbonyl, benzyloxy carbonyl, trichloroethoxycarbonyl, triphenylmethyl, and sulfonyl. A person of ordinary skill in the art will recognize that the acyclic precursor can be a single diastereomer or a mixture of diastereomers.

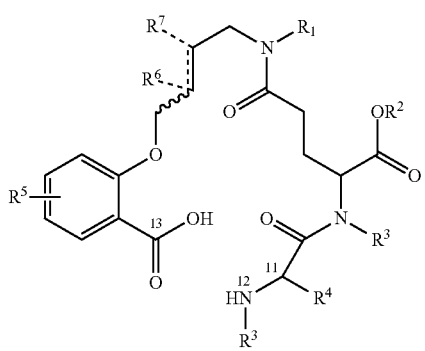

Formula 15

With reference to general Formula 15, $R^1$ is selected from hydrogen, aliphatic (alkyl, alkenyl, alkynyl), substituted aliphatic aromatic, substituted aromatic, arylalkyl, such as benzyl, and homologated benzyl, substituted arylalkyl, such as substituted benzyl, and substituted homologated benzyl, benzoyl, ester, ketone, tert-butoxycarbonyl, 9H-fluoren-9-ylmethoxycarbonyl, allyloxycarbonyl, benzyloxy carbonyl, trichloroethoxycarbonyl, triphenylmethyl, and sulfonyl. $R^2$ is selected from hydrogen, aliphatic, typically alkyl, more typically lower alkyl, such as methyl, ethyl, propyl, and butyl. Each $R^3$ is independently selected from hydrogen, aliphatic, such as alkyl, more typically lower alkyl, such as methyl, ethyl, propyl, and butyl, substituted aliphatic, aromatic, substituted aromatic, arylalkyl, such as benzyl, homologated benzyl, substituted arylalkyl, such as substituted benzyl, substituted homologated benzyl benzoyl, ester, ketone, tert-butoxycarbonyl, 9H-fluoren-9-ylmethoxycarbonyl, allyloxycarbonyl, benzyloxy carbonyl, trichloroethoxycarbonyl, triphenylmethyl, and sulfonyl. $R^4$ is selected from hydrogen, lower alkyl, such as methyl, —CH(CH$_3$)CH$_2$CH$_3$, —CH$_2$CH(CH$_3$)$_2$, —(CH$_2$)$_2$SCH$_3$, benzyl, substituted benzyl, 3-indole, —CH(CH$_3$)$_2$, —CH$_2$OH, —CH(OH)(CH$_3$), —CH$_2$C(O)NH$_2$, —(CH$_2$)$_2$C(O)NH$_2$, —CH$_2$SH, —CH$_2$SeH, —(CH$_2$)$_3$NHC(NH$_2^+$)NH$_2$, —CH$_2$(imidazole), —(CH$_2$)$_4$NH$_2$, —CH$_2$C(O)OH, or —(CH$_2$)$_2$C(O)OH. In some embodiments, $R_3$ and $R_4$ individually are or together form a 5-membered ring, and any natural or non-natural amino acid side chain. $R^5$ is selected from aliphatic, substituted aliphatic, alkoxy, particularly lower alkoxy, such as methoxy, substituted alkoxy, amine, substituted amine, amide, substituted amide, aryl, substituted aryl, aryl alkyl, substituted aryl alkyl, cyclic, substituted cyclic, ester, ether, formyl, halogen, heterocyclic, substituted heterocyclic, heteroaryl, substituted heteroaryl, hydrogen, hydroxyl, ketone, substituted ketone, nitro, nitroso, protecting groups, silyl, silyl ether, silyl ester, thiol, thioether, thioester. The acyclic precursor can contain an optional double bond, represented by "═══" The double bond geometry can be either Z or E, as indicated by the wavy bond "⁓" connected to the double bond. $R^6$ and $R^7$ can be hydrogen when the double bond is present, or the acyclic precursor can be saturated, wherein $R^6$ and $R^7$ can be selected from aliphatic, amino, halogen, hydrogen, hydroxyl, or $R^6$ and $R^7$ together form an epoxide or aziridine. A person of ordinary skill in the art will recognize that the acyclic precursor can be a single diastereomer or a mixture of diastereomers.

III. Embodiments of a Method for Making Macrocycles

Scheme 1

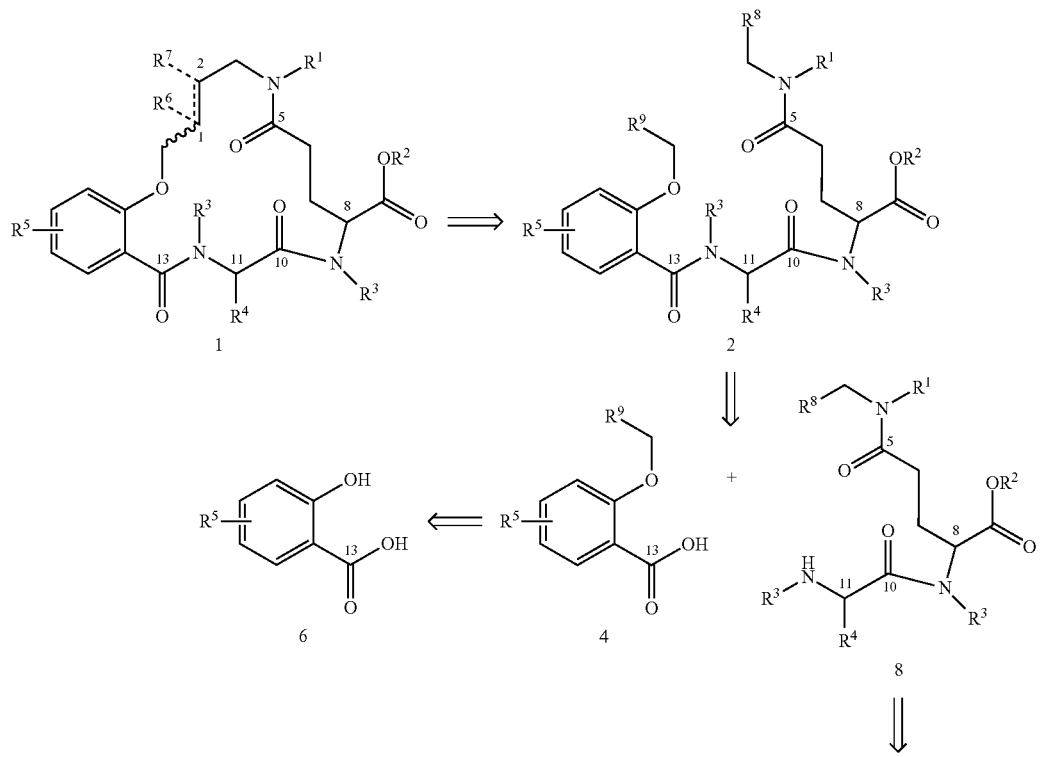

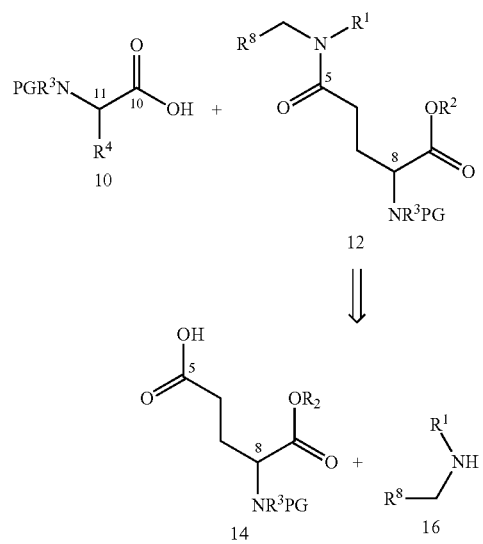

Scheme 1 illustrates one retrosynthetic approach to macrocycle 1. Disconnection of the macrocyclic scaffold 1 at the carbon atoms bearing $R^6$ and $R^7$ leads to the acyclic precursor 2. Acyclic precursor 2 can be obtained by coupling salicylic acid derivative 4 with dipeptide 8, utilizing peptide coupling conditions. The salicylic acid derivative 4 is obtained by substitution of salicylic acid starting material 6. Dipeptide 8 can be formed through reaction of two selected amino acids, either naturally or non-naturally occurring amino acids, such as the protected amino acid 10 and glutamic acid derivative 12, illustrated in Scheme 1. The glutamic acid derivative 12 is obtained via a peptide coupling between protected glutamic acid 14 and amine 16.

Amine 16 then undergoes an amide bond formation reaction with protected glutamic acid 14 to yield 12. The amide bond formation can be carried out with any activating group capable of activating the carboxylic acid moiety present in protected glutamic acid 14, including, but not limited to, N-ethyl-N'-(3-dimethylaminopropyl)carbodiimide (EDC), 1-ethyl-3-(3-dimethylaminopropyl)carbodiimide hydrochloride (EDCI), dicyclohexylcarbodiimide (DCC), carbonyl diimidazole (CDI), 1-hydroxybenzotriazole (HOBt), 1-hydroxy-7-aza-benzotriazole (HOAt), and o-(7-azabenzotriazol-1-yl)-N,N,N',N'-tetramethyluronium hexafluorophosphate (HATU). A person of ordinary skill in the art will recognize that the glutamic acid derivative 12 can be enantiopure, as either the R or S enantiomer, or a mixture of R and S enantiomers. With reference to compound 20, X can be selected from I, Br, Cl, F, and $R^1$-$R^3$, and $R^8$ are as recited previously.

Scheme 2

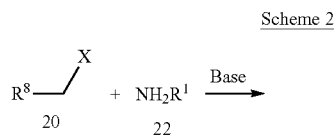

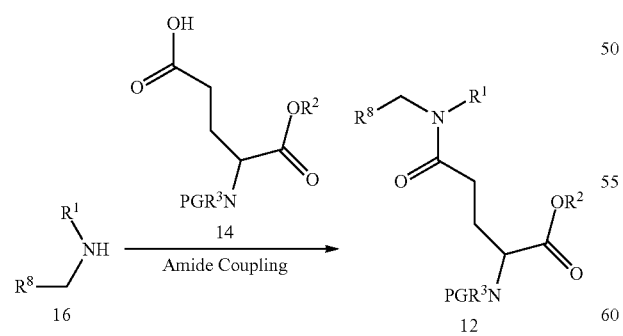

Scheme 2 describes the synthesis of glutamic acid derivative 12. A substituted amine 22 is reacted with a halogenated compound 20 to give amine 16. This reaction can be carried out with any base capable of deprotonating a primary amine, including, but not limited to CsOH, LiOH, NaOH, and KOH.

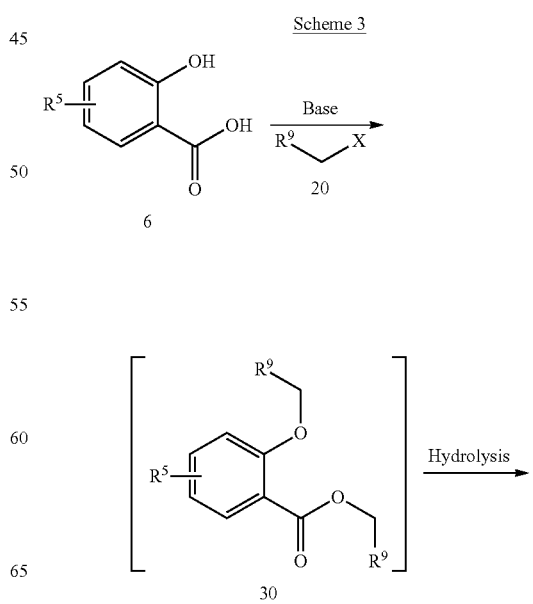

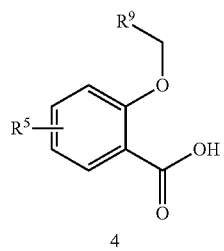

Scheme 3 illustrates one embodiment wherein a salicylic acid derivative 6 is bis-substituted under basic conditions, using halide 20. Appropriate bases include, but are not limited to $K_2CO_3$, $Cs_2CO_3$, and $Na_2CO_3$. The resulting bis-substituted intermediate 30 is subsequently hydrolyzed to the corresponding carboxylic acid 4 under aqueous, basic conditions. With reference to Scheme 3, X can be I, Br, Cl, F, and $R^5$ and $R^9$ are as recited previously.

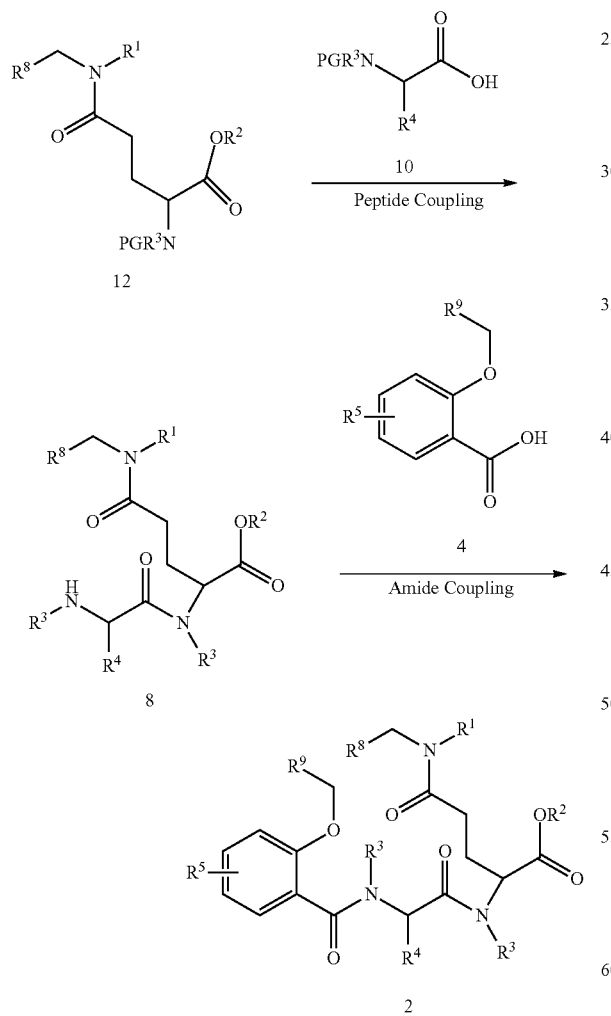

Scheme 4 illustrates another embodiment, wherein the glutamic acid derivative 12 undergoes a peptide coupling with a protected amino acid compound 10, followed by a subsequent amide bond formation between amine 8 and salicylic acid derivative 4. The peptide coupling between glutamic acid derivative 12 and protected amino acid 10 can be carried out with any activating group capable of activating the carboxylic acid moiety present in the protected amino acid 10, including, but not limited to, N-ethyl-N'-(3-dimethylaminopropyl)carbodiimide (EDC), 1-ethyl-3-(3-dimethylaminopropyl)carbodiimide hydrochloride (EDCI), dicyclohexylcarbodiimide (DCC), carbonyl diimidazole (CDI), 1-hydroxybenzotriazole (HOBt), 1-hydroxy-7-aza-benzotriazole (HOAt), and o-(7-azabenzotriazol-1-yl)-N,N,N',N'-tetramethyluronium hexafluorophosphate (HATU). A person of ordinary skill in the art will recognize that both glutamic acid derivative 12 and protected amino acid 10 can be enantiopure as either the R or S enantiomer, or can be a mixture of R and S enantiomers. In addition, the amine product 8 can be a single diastereomer or a mixture of diastereomers. The subsequent amide bond formation can also be carried out with similar conditions as the peptide coupling, listed previously. $R^1$-$R^4$, $R^8$, $R^9$ and PG are as recited previously. Typically if $R^8$ is —$C_{10}$=$CR^{11}R^{12}$, then $R^9$ is —$C_{10}$=$CR^{11}R^{12}$ and if $R^8$ is —C(O)H, then $R^9$ is selected from —$CH_2SO_2Ph$, —$CH_2PPh_3$, —$CH_2P(O)(OCH_2CF_3)_2$, —$CH_2P(O)(OEt)_2$, —$CH_2SO_2$-tetrazole. Alternatively, if $R^9$ is —C(O)H, then $R^8$ can be selected from —$CH_2SO_2Ph$, —$CH_2PPh_3$, —$CH_2P(O)(OCH_2CF_3)_2$, —$CH_2P(O)(OEt)_2$, and —$CH_2SO_2$-tetrazole, and any other reagent capable of undergoing ring closing metathesis or olefination.

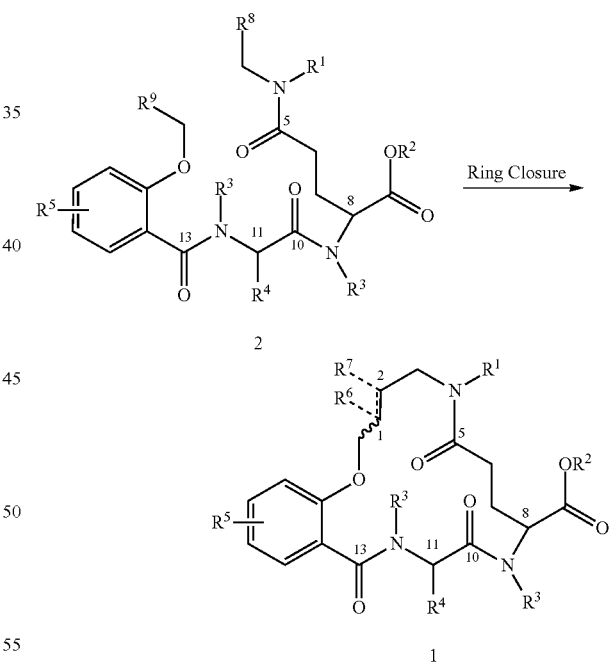

Scheme 5 illustrates a further embodiment, wherein the acyclic precursor 2 undergoes a reaction to form macrocycle 1. The ring closure can be carried out with transition metal carbene catalysts capable of catalyzing ring closing metathesis reactions including, but not limited to Grubbs' 1st generation catalyst, Grubbs' 2nd generation catalyst, the Grubbs-Hoveyda catalyst, and the Schrock catalyst. Alternative methods for ring closure include the use of olefination reactions, including, but not limited to Wittig olefination, Horner-Wadsworth-Emmons olefination, Gennari-Still olefination, and Julia-Lythgoe and Julia-Kocienski olefinations. These alternative ring forming reactions typically are used when $R^8$ is —C(O)H, then $R^9$ can be selected from —CH$_2$SO$_2$Ph, —CH$_2$PPh$_3$, —CH$_2$P(O)(OCH$_2$CF$_3$)$_2$, —CH$_2$P(O)(OEt)$_2$, —CH$_2$SO$_2$-tetrazole, or where $R^9$ is —C(O)H, then $R^8$ can be selected from —CH$_2$SO$_2$Ph, —CH$_2$PPh$_3$, —CH$_2$P(O)(OCH$_2$CF$_3$)$_2$, —CH$_2$P(O)(OEt)$_2$, and —CH$_2$SO$_2$-tetrazole. A person of ordinary skill the art will recognize that the olefin geometry resulting from the ring closing metathesis reaction can be either Z or E. Examples of these reactions are illustrated below.

Wittig Olefination

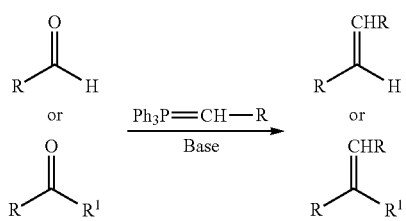

Julia-Lythgoe Olefination

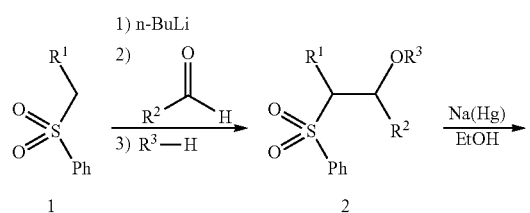

Horner-Wadsworth-Emmons Olefination

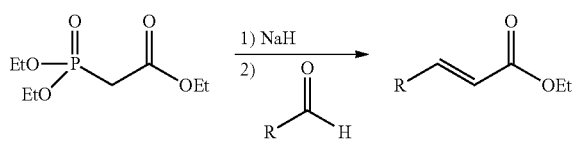

Gennari-Still Olefination

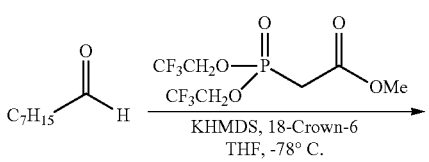

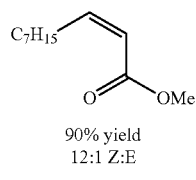

90% yield
12:1 Z:E

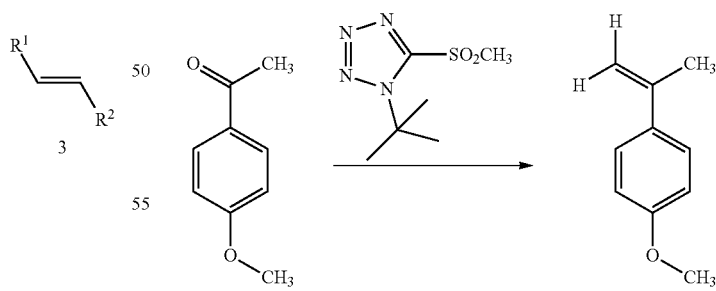

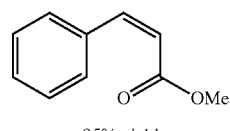

95% yield
50:1 Z:E

Julia-Kocenski Olefination

With reference to Scheme 5, the macrocycle 1 can contain an olefin at the indicated position, wherein the olefin geometry can be either Z or E. $R^6$ and $R^7$ can be aliphatic or hydrogen, or the macrocycle can be saturated, wherein $R^6$ and $R^7$ can be selected independently from aliphatic, hydrogen, hydroxyl, halogen, or be bonded together to form an epoxide. $R^1$-$R^5$ are as recited previously.

An additional approach to the formation of macrocycle 1 is illustrated below.

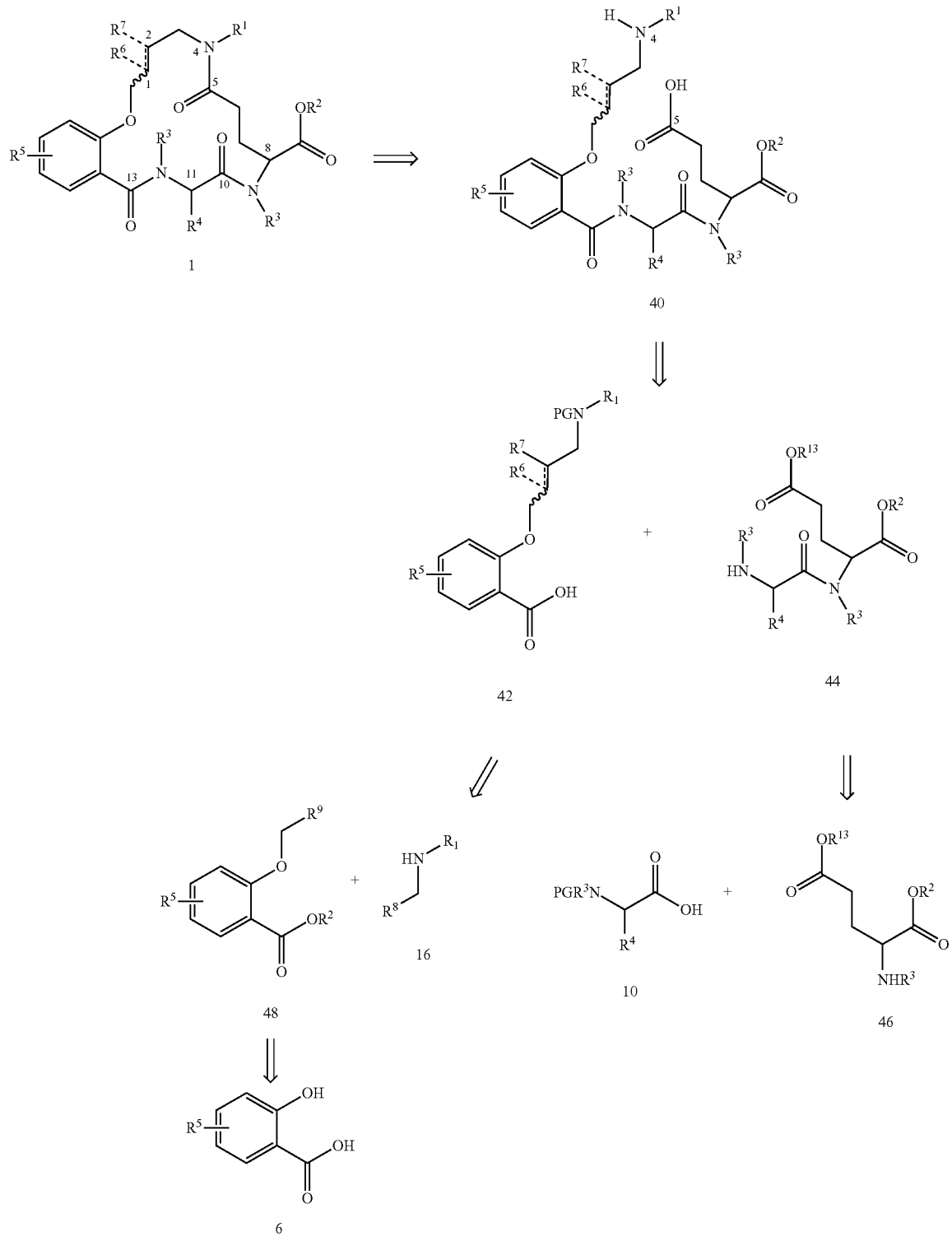

Scheme 6

Scheme 6 illustrates another retrosynthetic approach to macrocycle 1. Disconnection of the macrocyclic scaffold 1 between the amine at position 4 and the carbon atom at position 5, of the amide bond, provides the acyclic precursor 40. The acyclic precursor 40 is obtained via amide bond formation between dipeptide 44 and salicylic acid derivative 42. The salicylic acid derivative 42 may be obtained by substitution of salicylic acid starting material 6. Dipeptide 44 can be formed by reacting a selected amino acid, either a naturally or non-naturally occurring amino acid, such as the protected amino acid 10 and amine 46, illustrated in Scheme 6. Salicylic acid derivative 42 can be produced by a cross metathesis reaction between salicylic acid derivative 4 and di-substituted amine 16, or via other olefination techniques as would be understood by a person of ordinary skill in the art as exemplified by those described herein. Salicylic acid derivative 4 may be obtained via substitution of salicylic acid starting material 6.

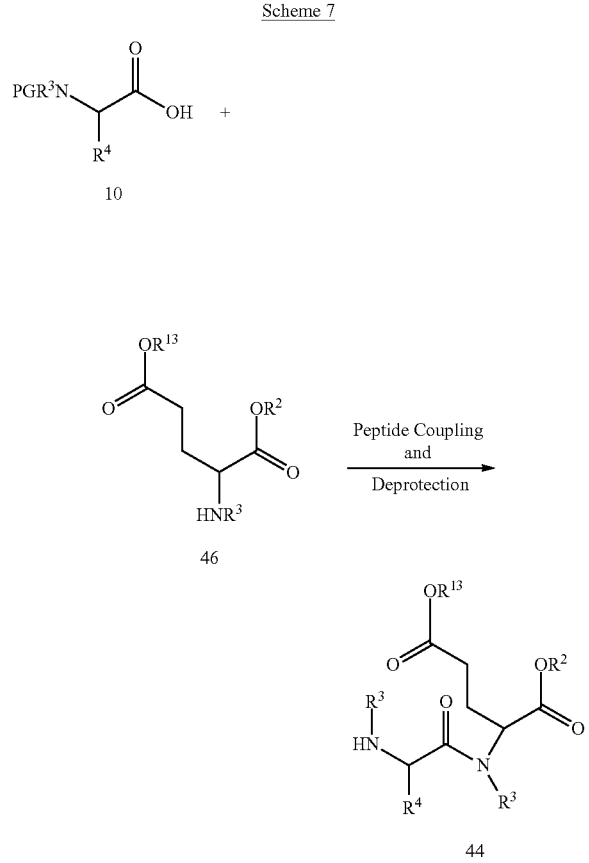

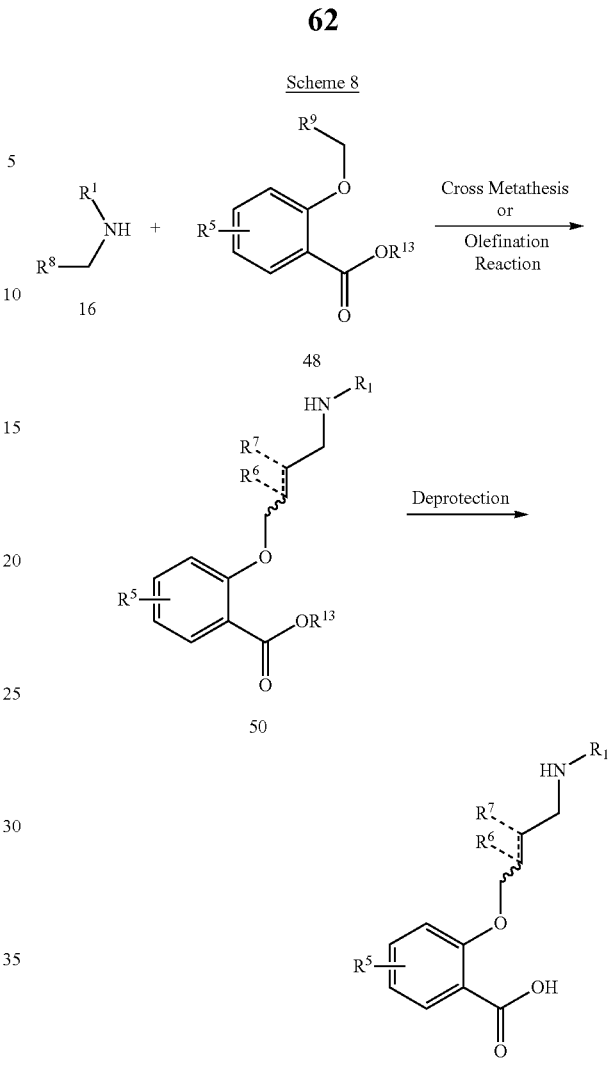

Scheme 7 illustrates the synthesis of dipeptide 44. Dipeptide 44 may be formed via a peptide coupling reaction between amine 46 and protected amino acid 10. The peptide coupling can be carried out with any activating group capable of activating the carboxylic acid moiety present in protected amino acid 10, including, but not limited to, N-ethyl-N'-(3-dimethylaminopropyl)carbodiimide (EDC), 1-ethyl-3-(3-dimethylaminopropyl)carbodiimide hydrochloride (EDCI), dicyclohexylcarbodiimide (DCC), carbonyl diimidazole (CDI), 1-hydroxybenzotriazole (HOBt), 1-hydroxy-7-azabenzotriazole (HOAt), and o-(7-azabenzotriazol-1-yl)-N,N,N',N'-tetramethyluronium hexafluorophosphate (HATU). A person of ordinary skill in the art will recognize that any of 10, 46, or 44 can be enantiopure, as either the R or S enantiomer, or a mixture of R and S enantiomers. A protected dipeptide precursor to dipeptide 44 is deprotected using standard conditions known to those of ordinary skill in the art.

Scheme 8 illustrates a further embodiment, wherein di-substituted amine 16 is coupled with salicylic acid derivative 48. The coupling can be accomplished through a cross metathesis reaction. Reagents for this transformation can include transition metal carbene catalysts capable of catalyzing olefin cross metathesis reactions including, but not limited to Grubbs' 1st generation catalyst, Grubbs' 2nd generation catalyst, the Grubbs-Hoveyda catalyst, and the Schrock catalyst. Alternative methods for coupling di-substituted amine 16 and salicylic acid derivative 48 include using olefination reactions, including, but not limited to Wittig olefination, Horner-Wadsworth-Emmons olefination, Gennari-Still olefination, and Julia-Lythgoe and Julia-Kocienski olefinations. These alternative ring forming reactions typically are used when $R^8$ is —C(O)H, then $R^9$ can be selected from —CH$_2$SO$_2$Ph, —CH$_2$PPh$_3$, —CH$_2$P(O)(OCH$_2$CF$_3$)$_2$, —CH$_2$P(O)(OEt)$_2$, —CH$_2$SO$_2$-tetrazole. $R^9$ may be —C(O)H, in which case, $R^8$ can be selected from —CH$_2$SO$_2$Ph, —CH$_2$PPh$_3$, —CH$_2$P(O)(OCH$_2$CF$_3$)$_2$, —CH$_2$P(O)(OEt)$_2$, and —CH$_2$SO$_2$-tetrazole. A person of ordinary skill the art will recognize that the olefin geometry resulting from the ring closing metathesis reaction can be either Z or E. Protected acid 50 can be converted to an intermediate 42 in order to make the substrate amenable to amide bond formation in a subsequent step.

Scheme 9

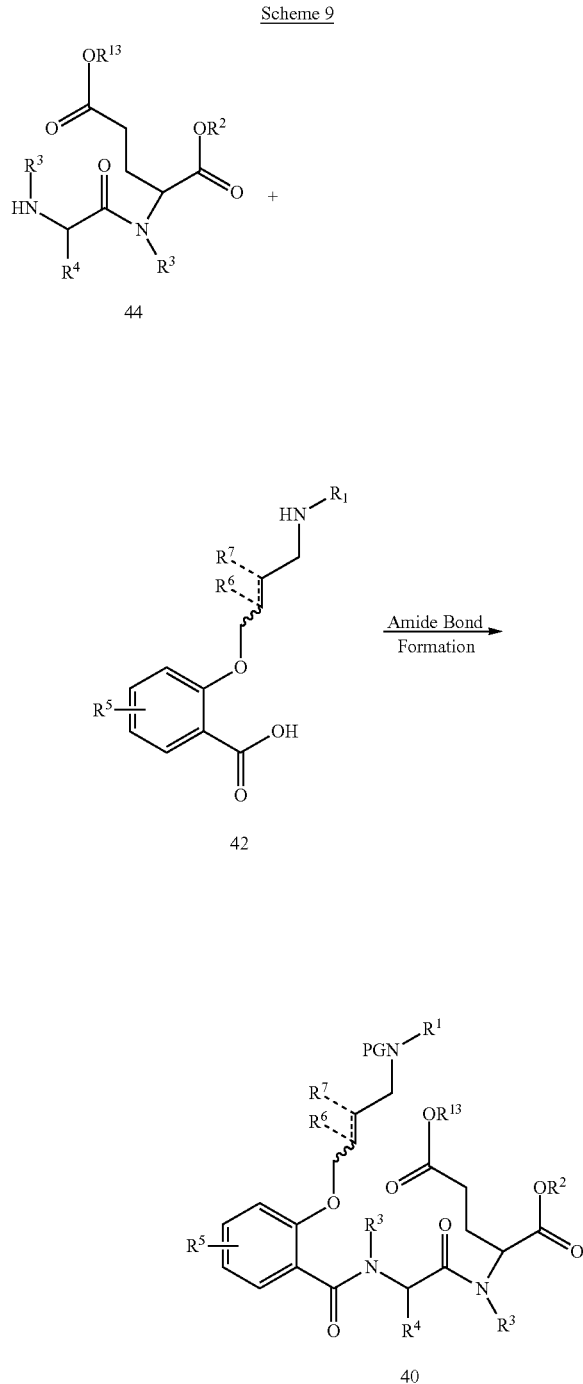

Scheme 9 illustrates the formation of the acyclic precursor 40. Dipeptide 44 can undergo an amide bond formation reaction with substituted salicylic acid derivative 42 to form the acyclic precursor 40. The amide bond formation reaction can be carried out with any activating group capable of activating the carboxylic acid moiety present in substituted salicylic acid derivative 42, including, but not limited to, N-ethyl-N'-(3-dimethylaminopropyl)carbodiimide (EDC), 1-ethyl-3-(3-dimethylaminopropyl)carbodiimide hydrochloride (EDCI), dicyclohexylcarbodiimide (DCC), carbonyl diimidazole (CDI), 1-hydroxybenzotriazole (HOBt), 1-hydroxy-7-azabenzotriazole (HOAt), and o-(7-azabenzotriazol-1-yl)-N,N,N',N'-tetramethyluronium hexafluorophosphate (HATU). A person of ordinary skill in the art will recognize that compounds 44 and 40 can be enantiopure, as either the R or S enantiomer, or a mixture of R and S enantiomers.

Scheme 10

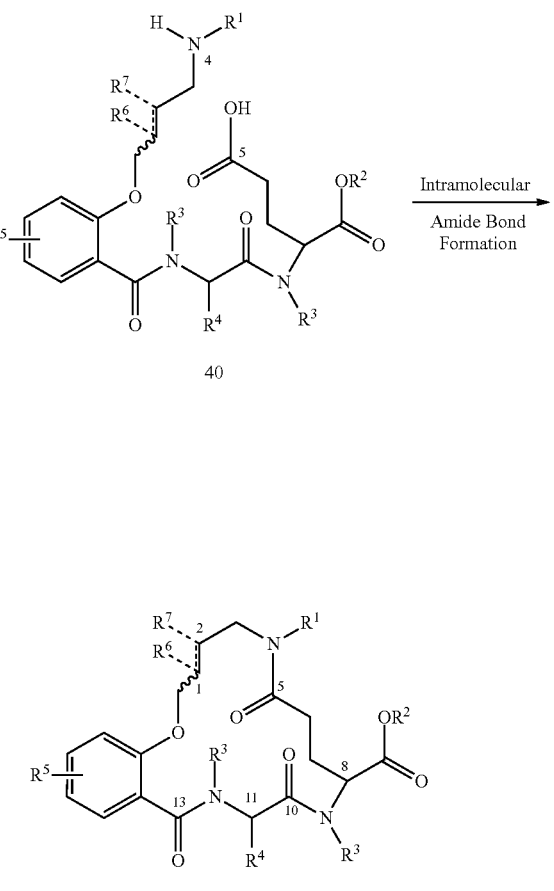

Macrocycle 1 can be produced from acyclic precursor 40 via an intramolecular amide bond formation reaction, illustrated in Scheme 10. This reaction forms a bond between the free amine of 40 and the carboxylic acid moiety at carbon 5 to provide the macrocycle. This reaction can be carried out with any activating group capable of activating the carboxylic acid moiety present at position 5 in acyclic precursor 40, including, but not limited to, N-ethyl-N'-(3-dimethylaminopropyl) carbodiimide (EDC), 1-ethyl-3-(3-dimethylaminopropyl) carbodiimide hydrochloride (EDCI), dicyclohexylcarbodiimide (DCC), carbonyl diimidazole (CDI), 1-hydroxybenzotriazole (HOBt), 1-hydroxy-7-azabenzotriazole (HOAt), and o-(7-azabenzotriazol-1-yl)-N,N,N',N'-tetramethyluronium hexafluorophosphate (HATU). A person of ordinary skill in the art will recognize that the amine 40 can be enantiopure, as either the R or S enantiomer, or a mixture of R and S enantiomers.

Scheme 11

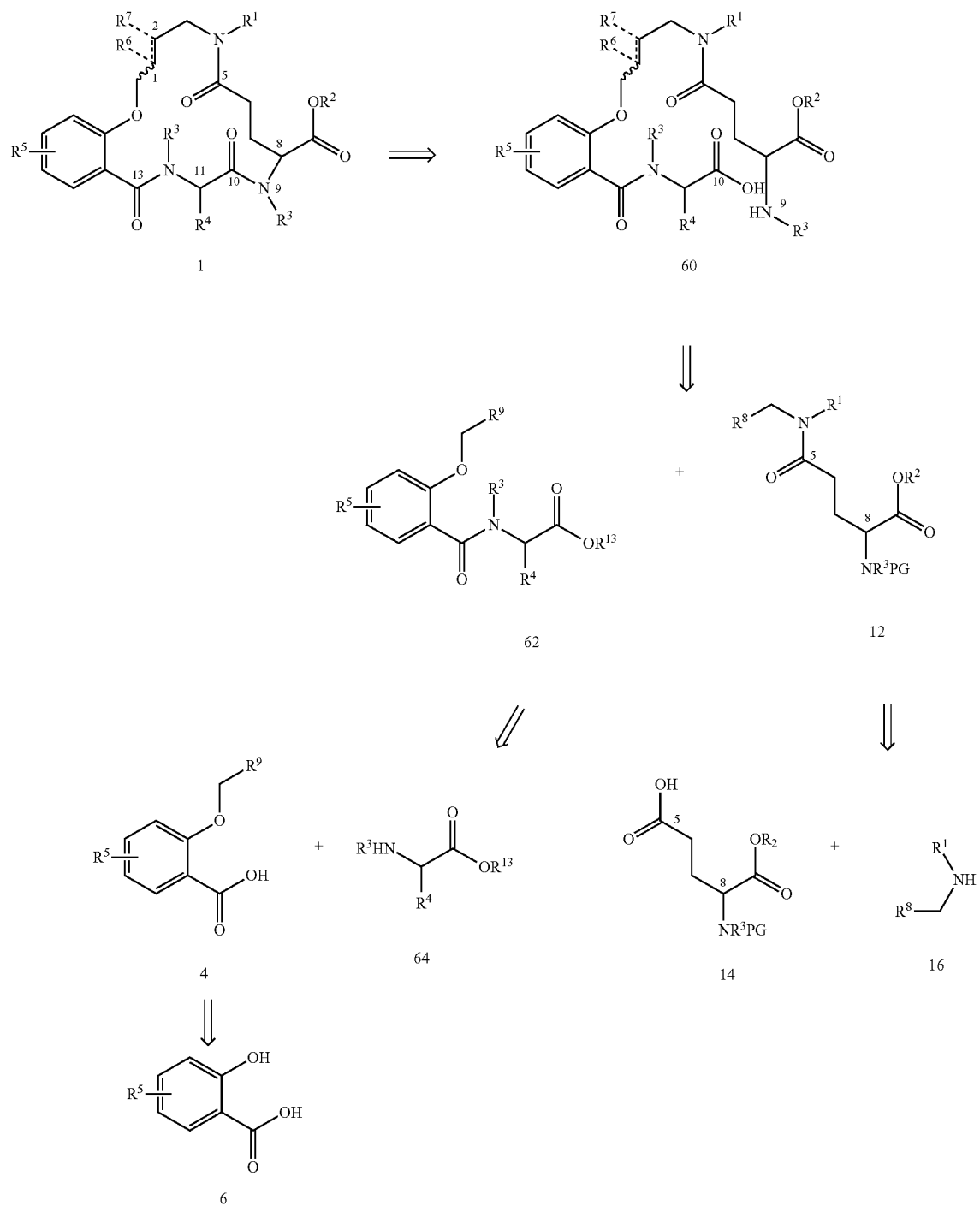

Another retrosynthetic approach to macrocycle 1 is illustrated in Scheme 11. This approach utilizes an intramolecular peptide bond formation between the amine terminus of acyclic precursor 60 and the carboxylic acid terminus. Acyclic precursor 60 can be obtained by performing a cross metathesis reaction between glutamic acid derivative 12 and salicylic acid derivative 62. Acyclic precursor 60 can be obtained by other reactions, such as an olefination reaction between the two substrates, 12 and 62. Glutamic acid derivative 12 may be obtained via amide bond formation between di-substituted amine 16 and protected glutamic acid 14. The salicylic acid derivative 62 can be obtained via amide bond formation between amino acid 10 and substituted salicylic acid 4. As previously disclosed, the substituted salicylic acid 4 may be obtained via substitution of salicylic acid 6.

Scheme 12

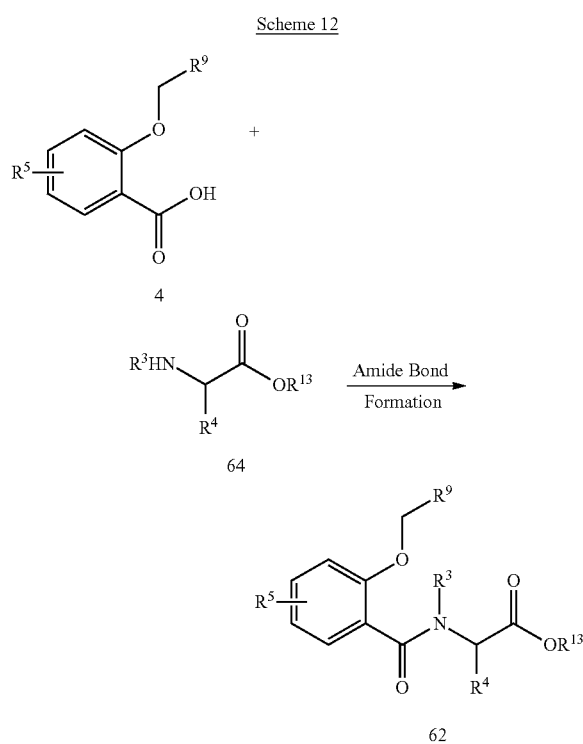

Scheme 12 illustrates the formation of peptide-coupled salicylic acid derivative 62. This conversion utilizes an amide bond formation between salicylic acid derivative 4 and amino acid 64. This reaction can be carried out with any activating group capable of activating the carboxylic acid moiety of salicylic acid derivative 4, as would be understood by a person of ordinary skill in the art as exemplified by those previously disclosed. A person of ordinary skill in the art will recognize that the peptide-coupled salicylic acid derivative 62 can be enantiopure, as either the R or S enantiomer, or a mixture of R and S enantiomers.

Scheme 13

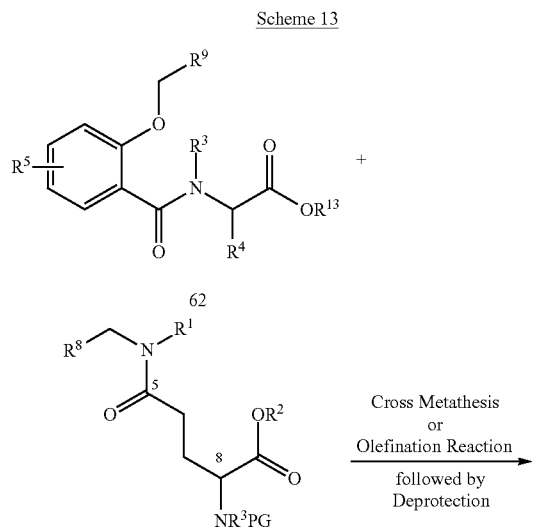

Scheme 13 illustrates the conversion of peptide-coupled salicylic acid derivative 62 and glutamic acid derivative 12 to the acyclic precursor 60. This conversion can occur using a cross metathesis reaction with reagents as understood by a person of ordinary skill in the art is exemplified by reagents that have been previously disclosed herein. Previous embodiments disclose the use of alternative methods that can be used to couple glutamic acid derivative 12 and peptide-coupled salicylic acid derivative 62. Any of these previously disclosed conditions can be used in this transformation. A person of ordinary skill the art will recognize that the olefin geometry resulting from the ring closing metathesis reaction can be either Z or E. The resulting protected acid can be converted to acyclic precursor 60 in order to make the substrate amenable to amide bond formation in subsequent steps.

Scheme 14

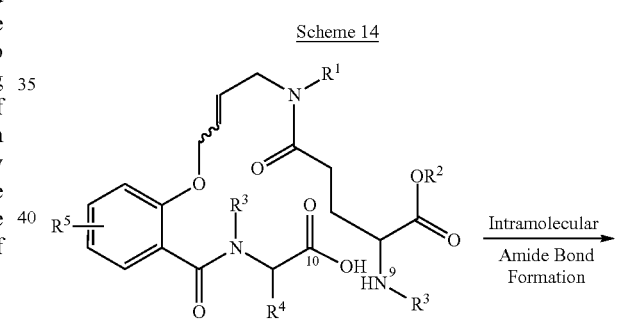

Macrocycle 1 can be produced from acyclic precursor 60 via an intramolecular amide bond formation reaction. This reaction, illustrated in Scheme 14, can close the macrocycle by forming a bond between the free amine terminus and the carboxylic acid terminus at position 10. This reaction can be carried out with any previously disclosed activating group capable of activating the carboxylic acid terminus present at position 10 in acyclic precursor 60.

Scheme 15

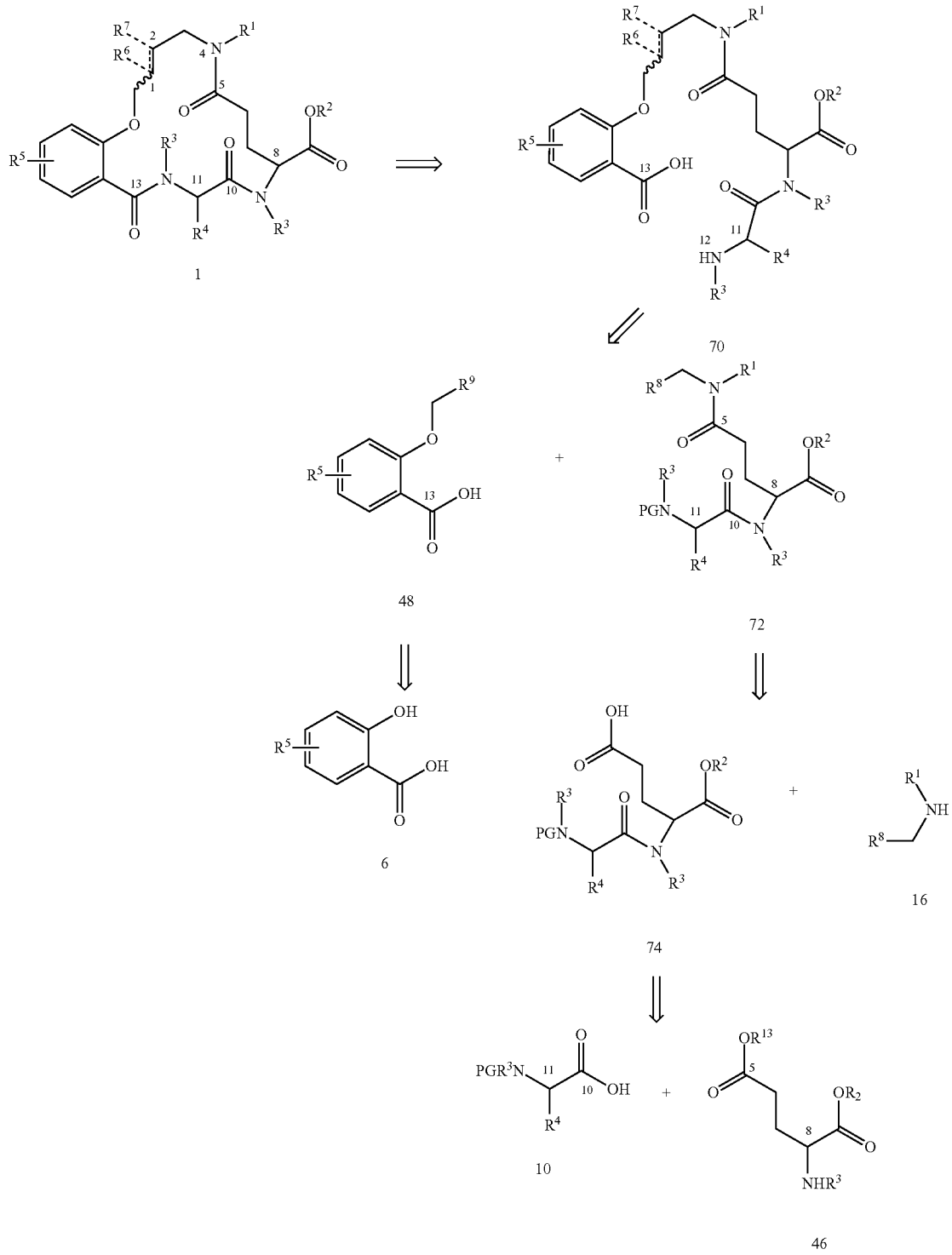

Still another retrosynthetic approach to macrocycle 1 is illustrated in Scheme 15. This approach utilizes an intramolecular amide bond formation reaction of acyclic precursor 70. This acyclic precursor is synthesized using a cross metathesis reaction between protected amine 72 and salicylic acid derivative 48, or other techniques, such as olefination reactions. Protected amine 72 can be obtained by amide bond formation between di-substituted amine 16 and carboxylic acid 74. Carboxylic acid 74 may be synthesized via peptide bond formation between glutamic acid derivative 46 and amino acid 10. The salicylic acid 48 is obtained as previously disclosed.

Scheme 16

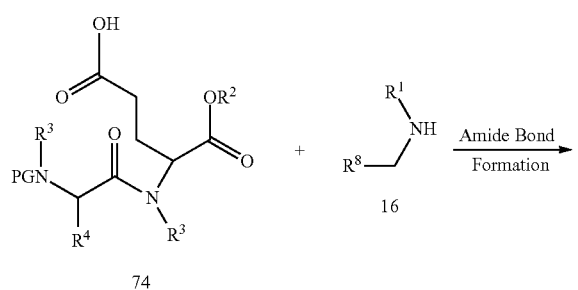

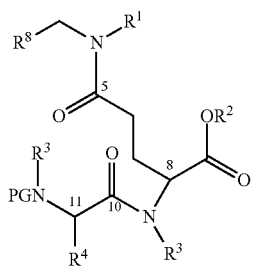

Scheme 16 illustrates the formation of dipeptide 72. Carboxylic acid intermediate 74 can undergo an amide bond formation reaction with di-substituted amine 16. This reaction can be carried out with any reagents known to a person of ordinary skill in the art for amide bond formation and exemplified by those that have been previously disclosed herein. A person of ordinary skill in the art will recognize that the dipeptide 72 can be enantiopure, as either the R or S enantiomer, or a mixture of R and S enantiomers.

Scheme 17

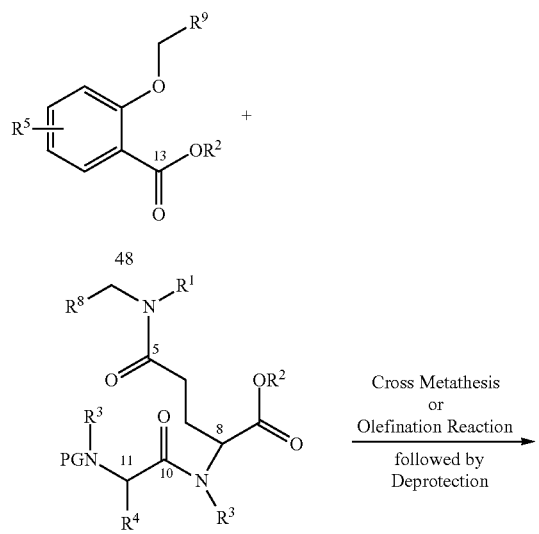

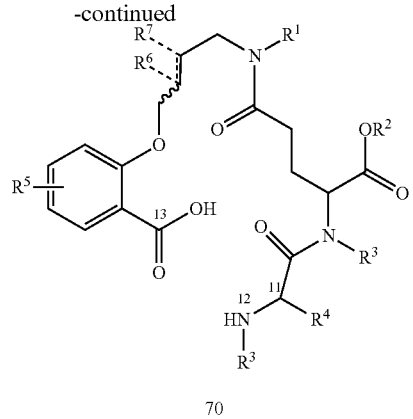

Scheme 17 illustrates the formation of acyclic precursor 70. Salicylic acid derivative 48 can be coupled with dipeptide 72 via the cross metathesis and/or olefination reactions known to a person of ordinary skill in the art to be exemplified by those previously disclosed herein. This transformation may be followed by a deprotection step to provide acyclic ring precursor 70. A person of ordinary skill in the art will recognize that acyclic precursor 70 can be enantiopure, as either the R or S enantiomer, or a mixture of R and S enantiomers.

Scheme 18

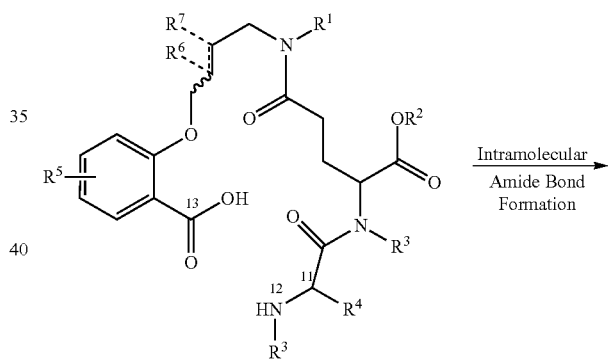

Scheme 18 illustrates another variation of intramolecular amide bond formation to form macrocycle 1. This reaction can convert acyclic precursor 70 to macrocycle 1 using similar conditions know to a person of ordinary skill in the art as exemplified by those previously described herein. A person of ordinary skill in the art will recognize that macrocycle 1 can be enantiopure, as either the R or S enantiomer, or a mixture of R and S enantiomers.

IV. Chemically Modifying Macrocycles

Once the macrocycle is formed, a person of ordinary skill in the art will appreciate that the macrocycle, particularly functional groups thereof, can undergo additional modifications to make additional analogs of the initially formed macrocycle. The present invention is directed to all such modifications.

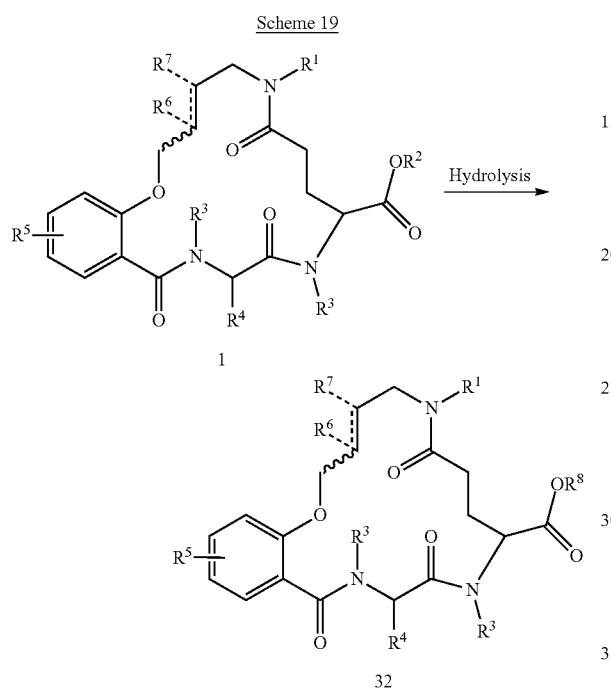

Scheme 19 illustrates a first embodiment in which the macrocycle can undergo further chemical manipulation. The ester moiety of macrocycle 1, wherein $R^2$ is selected from aliphatic, typically alkyl, more typically lower alkyl, such as methyl, ethyl, propyl, and butyl, can undergo (1) hydrolysis to form the corresponding carboxylic acid 32, where $R^8$ is hydrogen, or (2) transesterification where $R^8$ is a different aliphatic group than $R^2$. Macrocycle 32 can contain an olefin at the indicated position, wherein the olefin geometry can be either Z or E. $R^6$ and $R^7$ can be aliphatic or hydrogen. The macrocycle can be saturated, wherein $R^6$ and $R^7$ is selected from aliphatic, hydrogen, hydroxyl, or be bonded together to form an epoxide. $R^1$ is selected from hydrogen, aliphatic, substituted aliphatic, aromatic, substituted aromatic, arylalkyl, such as benzyl, homologated benzyl, substituted arylalkyl, such as substituted benzyl, substituted homologated benzyl, benzoyl, ester, ketone, tert-butoxycarbonyl, 9H-fluoren-9-ylmethoxycarbonyl, allyloxycarbonyl, benzyloxy carbonyl, trichloroethoxycarbonyl, triphenylmethyl, and sulfonyl; $R^3$ is selected from hydrogen, aliphatic, alkyl, more typically lower alkyl, such as methyl, ethyl, propyl, and butyl, substituted aliphatic, aromatic, substituted aromatic, arylalkyl, such as benzyl, homologated benzyl, substituted arylalkyl, such as substituted benzyl, substituted homologated benzyl, benzoyl, ester, ketone, tert-butoxycarbonyl, 9H-fluoren-9-ylmethoxycarbonyl, allyloxycarbonyl, benzyloxy carbonyl, trichloroethoxycarbonyl, triphenylmethyl, and sulfonyl; $R^4$ is selected from hydrogen, methyl, $CH(CH_3)$ $CH_2CH_3$, $CH_2CH(CH_3)_2$, $(CH_2)_2SCH_3$, benzyl, substituted benzyl, 3-indole, $CH(CH_3)_2$, $CH_2OH$, $CH(OH)(CH_3)$, $CH_2C(O)NH_2$, $(CH_2)_2C(O)NH_2$, $CH_2SH$, $CH_2SeH$, $(CH_2)_3NHC(NH_2^+)NH_2$, $CH_2$(imidazole), $(CH_2)_4NH_2$, $CH_2C(O)OH$, $(CH_2)_2C(O)OH$, and any non-natural amino acid side chain; $R^5$ is selected from aliphatic, substituted aliphatic, alkoxy, particularly lower alkoxy, such as methoxy, substituted alkoxy, amine, substituted amine, amide, substituted amide, aryl, substituted aryl, arylalkyl, substituted arylalkyl, cyclic, substituted cyclic, ester, ether, formyl, halogen, heterocyclic, substituted heterocyclic, heteroaryl, substituted heteroaryl, hydrogen, hydroxyl, ketone, substituted ketone, nitro, nitroso, protecting groups, silyl, silyl ether, silyl ester, thiol, thioether, and thioester.

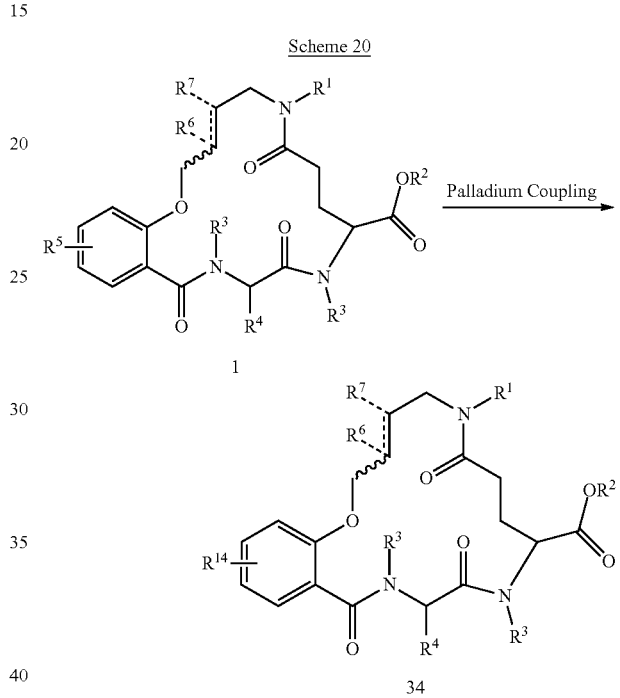

Scheme 20 illustrates a further embodiment in which the macrocycle can undergo a metal-catalyzed coupling reaction, such as a palladium-catalyzed coupling reaction. In this embodiment, $R^5$ is selected from I, Br, Cl, F, and OTf, more typically Br and Cl. For example, $R^5$ can undergo palladium-catalyzed coupling to give rise to $R^{14}$-substituted macrocycle 34. Palladium-catalyzed coupling reactions that can be employed for this transformation include, but are not limited to, Suzuki couplings, Negishi couplings, Hiyama couplings, and Stille reactions. Catalysts for this transformation include any palladium catalyst capable of oxidatively adding to the aryl-halide bond, including, but not limited to $Pd(OAc)_2$, $PdCl_2(dppf)_2$, $Pd(PPh_3)_4$, $Pd_2(dba)_3$. With reference to Scheme 20, $R^{14}$ can include, but is not limited to, aliphatic, substituted aliphatic, aryl, substituted aryl, heteroaryl, and substituted heteroaryl.

With reference to Scheme 20, the macrocycle 34 can contain an olefin at the indicated position, wherein the olefin geometry can be either Z or E, and $R^6$ and $R^7$ can be hydrogen, or the macrocycle can be saturated, wherein $R^6$ and $R^7$ can be selected from hydrogen, hydroxyl, or be bonded together to form an epoxide. $R^1$ can be selected from hydrogen, aliphatic, substituted aliphatic alkyl, alkenyl, alkynyl, aromatic, substituted aromatic, arylalkyl, such as benzyl, homologated benzyl, substituted arylalkyl, such as substituted benzyl, substituted homologated benzyl, benzoyl, ester, ketone, tert-butoxycarbonyl, 9H-fluoren-9-ylmethoxycarbonyl, allyloxycarbonyl, benzyloxy carbonyl, trichloroethoxycarbonyl, triphenylmethyl, and sulfonyl; $R^2$ can be selected from hydrogen, aliphatic, alkyl, more typically lower alkyl, such as methyl, ethyl, propyl, and butyl; $R^3$ can be selected from hydrogen, aliphatic, substituted aliphatic, alkyl, more typically lower alkyl, such as methyl, ethyl, propyl, and butyl, alkenyl, alkynyl, aromatic, substituted aromatic, arylalkyl, such as benzyl, homologated benzyl, substituted arylalkyl, such as substituted benzyl, benzoyl, ester, ketone, tert-butoxycarbonyl, 9H-fluoren-9-ylmethoxycarbonyl, allyloxycarbonyl, benzyloxy carbonyl, trichloroethoxycarbonyl, triphenylmethyl, and sulfonyl; $R^4$ can be selected from hydrogen, methyl, $CH(CH_3)CH_2CH_3$, $CH_2CH(CH_3)_2$, $(CH_2)_2SCH_3$, benzyl, substituted benzyl, 3-indole, $CH(CH_3)_2$, $CH_2OH$, $CH(OH)(CH_3)$, $CH_2C(O)NH_2$, $(CH_2)_2C(O)NH_2$, $CH_2SH$, $CH_2SeH$, $(CH_2)_3NHC(NH_2^+)NH_2$, $CH_2$(imidazole), $(CH_2)_4NH_2$, $CH_2C(O)OH$, $(CH_2)_2C(O)OH$, and any non-natural amino acid side chain.

Scheme 21

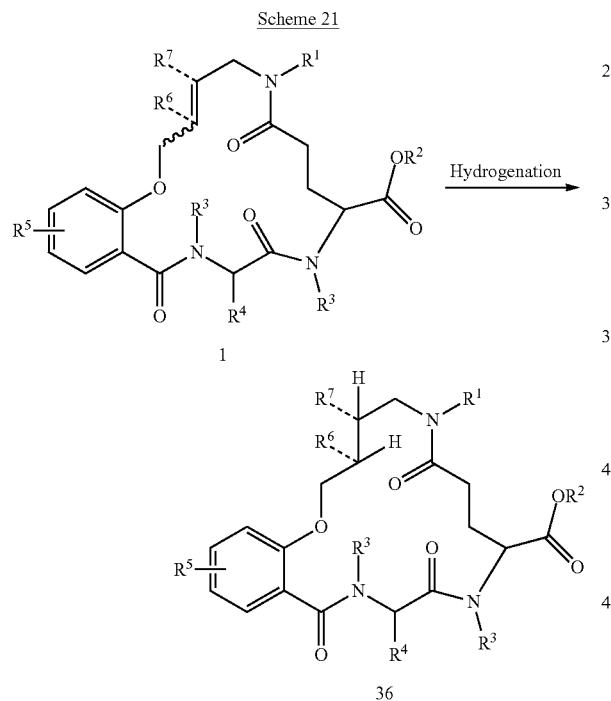

36

Scheme 21 illustrates another embodiment in which an olefin-containing macrocycle 1 can be converted to saturated macrocycle 36. This reaction involves hydrogenation of the olefin using conditions suitable for converting unsaturated bonds to the corresponding saturated bonds. Examples of reagents used for this process include Pd/C under an atmosphere of $H_2$, diimide, and Lindlar's catalyst.

With reference to Scheme 21, the macrocycle 36 can contain an olefin at the indicated position, wherein the olefin geometry can be either Z or E, and $R^6$ and $R^7$ can be hydrogen, or the macrocycle can be saturated, wherein $R^6$ and $R^7$ can be selected from hydrogen, hydroxyl, or be bonded together to form an epoxide. $R^1$ can be selected from hydrogen, aliphatic, substituted aliphatic alkyl, alkenyl, alkynyl, aromatic, substituted aromatic, arylalkyl, such as benzyl, homologated benzyl, substituted arylalkyl, such as substituted benzyl, substituted homologated benzyl, benzoyl, ester, ketone, tert-butoxycarbonyl, 9H-fluoren-9-ylmethoxycarbonyl, allyloxycarbonyl, benzyloxy carbonyl, trichloroethoxycarbonyl, triphenylmethyl, and sulfonyl; $R^2$ can be selected from hydrogen, aliphatic, alkyl, more typically lower alkyl, such as methyl, ethyl, propyl, and butyl; $R^3$ can be selected from hydrogen, aliphatic, substituted aliphatic, alkyl, more typically lower alkyl, such as methyl, ethyl, propyl, and butyl, alkenyl, alkynyl, aromatic, substituted aromatic, arylalkyl, such as benzyl, homologated benzyl, substituted arylalkyl, such as substituted benzyl, substituted homologated benzyl, benzoyl, ester, ketone, tert-butoxycarbonyl, 9H-fluoren-9-ylmethoxycarbonyl, allyloxycarbonyl, benzyloxy carbonyl, trichloroethoxycarbonyl, triphenylmethyl, and sulfonyl; $R^4$ can be selected from hydrogen, methyl, $CH(CH_3)CH_2CH_3$, $CH_2CH(CH_3)_2$, $(CH_2)_2SCH_3$, benzyl, substituted benzyl, 3-indole, $CH(CH_3)_2$, $CH_2OH$, $CH(OH)(CH_3)$, $CH_2C(O)NH_2$, $(CH_2)_2C(O)NH_2$, $CH_2SH$, $CH_2SeH$, $(CH_2)_3NHC(NH_2^+)NH_2$, $CH_2$(imidazole), $(CH_2)_4NH_2$, $CH_2C(O)OH$, $(CH_2)_2C(O)OH$, and any non-natural amino acid side chain; $R^5$ can be selected from aliphatic, substituted aliphatic, alkoxy, particularly lower alkoxy, such as methoxy, substituted alkoxy, amine, substituted amine, amide, substituted amide, aryl, substituted aryl, aryl alkyl, substituted aryl alkyl, cyclic, substituted cyclic, ester, ether, formyl, halogen, heterocyclic, substituted heterocyclic, heteroaryl, substituted heteroaryl, hydrogen, hydroxyl, ketone, substituted ketone, nitro, nitroso, protecting groups, silyl, silyl ether, silyl ester, thiol, thioether, thioester.

Scheme 22

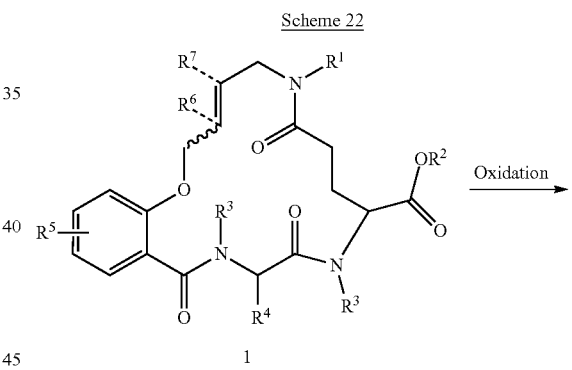

38

Scheme 22 illustrates another embodiment, wherein the olefin of macrocycle 1 is oxidized to a diol or an epoxide, wherein $R^6$ and $R^{10}$ are either both —OH, or together form an epoxide. The oxidation can be carried out with any reagents capable of oxidizing olefins, including, but not limited to, KMnO$_4$, OsO$_4$, Sharpless asymmetric dihydroxylation conditions, Sharpless asymmetric epoxidation conditions, Jacobsen's catalyst, Shi epoxidation conditions, dimethyldioxirane (DMDO), and meta-chloroperbenzoic acid (mCPBA).

With reference to Scheme 22, the macrocycle 38 can contain an olefin at the indicated position, wherein the olefin geometry can be either Z or E, and R$^6$ and R$^7$ can be hydrogen, or the macrocycle can be saturated, wherein R$^6$ and R$^7$ can be selected from hydrogen, hydroxyl, or be bonded together to form an epoxide. R$^1$ can be selected from hydrogen, aliphatic, substituted aliphatic alkyl, alkenyl, alkynyl, aromatic, substituted aromatic, arylalkyl, such as benzyl, homologated benzyl, substituted arylalkyl, such as substituted benzyl, substituted homologated benzyl, benzoyl, ester, ketone, tert-butoxycarbonyl, 9H-fluoren-9-ylmethoxycarbonyl, allyloxycarbonyl, benzyloxy carbonyl, trichloroethoxycarbonyl, triphenylmethyl, and sulfonyl; R$^2$ can be selected from hydrogen, aliphatic, alkyl, more typically lower alkyl, such as methyl, ethyl, propyl, and butyl; R$^3$ can be selected from hydrogen, aliphatic, substituted aliphatic, alkyl, more typically lower alkyl, such as methyl, ethyl, propyl, and butyl, alkenyl, alkynyl, aromatic, substituted aromatic, arylalkyl, such as benzyl, homologated benzyl, substituted arylalkyl, such as substituted benzyl, substituted homologated benzyl, benzoyl, ester, ketone, tert-butoxycarbonyl, 9H-fluoren-9-ylmethoxycarbonyl, allyloxycarbonyl, benzyloxy carbonyl, trichloroethoxycarbonyl, triphenylmethyl, and sulfonyl; R$^4$ can be selected from hydrogen, methyl, CH(CH$_3$)CH$_2$CH$_3$, CH$_2$CH(CH$_3$)$_2$, (CH$_2$)$_2$SCH$_3$, benzyl, substituted benzyl, 3-indole, CH(CH$_3$)$_2$, CH$_2$OH, CH(OH)(CH$_3$), CH$_2$C(O)NH$_2$, (CH$_2$)$_2$C(O)NH$_2$, CH$_2$SH, CH$_2$SeH, (CH$_2$)$_3$NHC(NH$_2$$^+$)NH$_2$, CH$_2$(imidazole), (CH$_2$)$_4$NH$_2$, CH$_2$C(O)OH, (CH$_2$)$_2$C(O)OH, and any non-natural amino acid side chain; and R$^5$ can be selected from aliphatic, substituted aliphatic, alkoxy, particularly lower alkoxy, such as methoxy, substituted alkoxy, amine, substituted amine, amide, substituted amide, aryl, substituted aryl, aryl alkyl, substituted aryl alkyl, cyclic, substituted cyclic, ester, ether, formyl, halogen, heterocyclic, substituted heterocyclic, heteroaryl, substituted heteroaryl, hydrogen, hydroxyl, ketone, substituted ketone, nitro, nitroso, protecting groups, silyl, silyl ether, silyl ester, thiol, thioether, and thioester.

V. Therapeutic Uses

Particular embodiments of the disclosed macrocyclic compounds may be useful for promoting gastrointestinal motility and for treating postoperative ileus and diabetic gastroparesis. U.S. Pat. No. 7,452,862 to Deslongchamps et al., for example, discloses macrocyclic compounds, which show agonistic and/or antagonistic activity of a mammalian motilin receptor and/or a mammalian ghrelin receptor. A representative ghrelin agonist and a representative motilin antagonist are shown below:

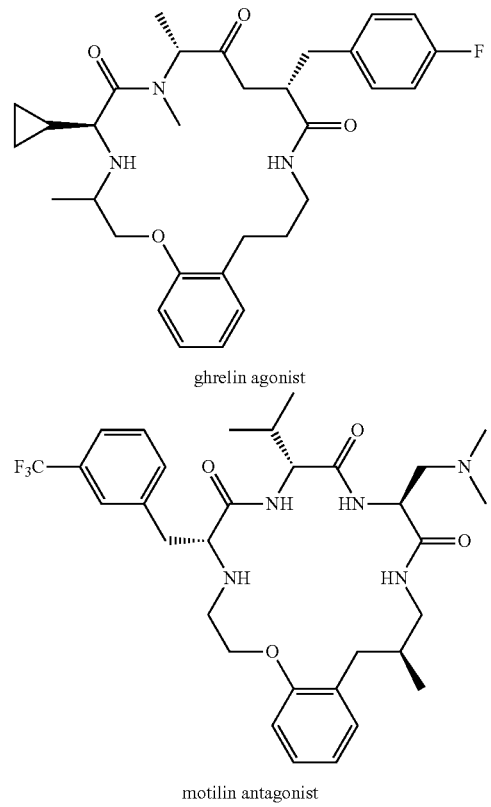

ghrelin agonist motilin antagonist

Motilin, a linear 22-amino acid peptide encoded by the MLN gene and secreted by endocrine M cells, plays a critical regulatory role in the GI physiological system by regulating fasting gastrointestinal motor activity. The peptide is periodically released from the duodenal mucosa during fasting in mammals, including humans. Motilin affects gastric motility through contraction of gastrointestinal smooth muscle to stimulate gastric emptying, decrease intestinal transit time and initiate phase III of the migrating motor complex in the small bowel. Agents that either diminish or enhance the activity at the motilin receptor, may be effective pharmaceuticals towards these indications.

Ghrelin is a 28-amino acid peptide hormone involved in a number of important physiological functions including growth hormone secretion, maintenance of energy balance, appetite and gut motility. The Ser3 residue of ghrelin is modified by n-octanoic acid. Non-modified forms of ghrelin have not been shown to be hormonally active. Ghrelin structurally resembles motilin, with about 21% amino acid homology. Their receptors also are structurally similar, with 44% amino acid homology. (Sakata et al., *International Journal of Peptides*, Article ID 945056, 7 pp., (2010).) Ghrelin is synthesized by endocrine cells (P/D1 cells) lining the stomach fundus and epsilon cells of the pancreas. Ghrelin is also produced in the hypothalamic arcuate nucleus where it stimulates growth hormone secretagogue receptors in the pituitary gland. Ghrelin also has been identified in the placenta. Although placental expression of ghrelin changes significantly throughout pregnancy, the physiological function of ghrelin in the placenta is unknown. The pituitary, heart, kidney, endocrine pancreas, gonads, lungs, and lymphocytes all express ghrelin in low amounts. (Casanueva et al., *Growth, Genetics & Hormones*, 20(1):1-8, (2004).)

Ghrelin binds to a G protein-coupled receptor (GPCR), also known as GHSR-1a, a growth hormone secretagogue (GHS) receptor. G protein-coupled receptors comprise a large protein family of transmembrane receptors that sense molecules outside a cell and activate signal transduction pathways within the cell. GPCR proteins have seven membrane-spanning domains. The ligands that bind to these receptors vary in size from small molecules to peptides to large proteins. In contrast to other types of receptors, GCPR ligands typically bind within a transmembrane domain. The human genome encodes thousands of GPCRs, about 350 of which detect hormones, growth factors, and other endogenous ligands. GPCRs are involved in a wide variety of physiological processes, including vision, smell, behavioral and mood regulation, regulation of immune system activity and inflammation, autonomic nervous system transmission, and cell density sensing. GPCRs are implicated in many diseases and are the target of nearly one-third of modern medicines. (Filmore, *Modern Drug Discovery*, 2004 (November):24-28; Overington et al., *Nat Ref Drug Discov*, 5(12):993-996 (2006).)

In an inactive state, G protein is bound to the G protein-coupled receptor. Recognition of a ligand by the GCPR causes a conformational change in the GCPR, allowing it to act as a guanine nucleotide exchange factor. The GCPR exchanges its bound GDP for GTP, thereby activating an associated G-protein comprising α, β, and γ subunits. The G-protein's α subunit, together with the bound GTP, dissociates from the β and γ subunits. The dissociated subunit can interact with intracellular signaling proteins or target functional proteins directly, depending on the α subunit type. When ghrelin binds to GHSR-1a, it activates the phospholipase C signaling route, resulting in an intracellular $Ca^{2+}$ rise. (Casanueva et al.)

Ghrelin is a potent growth hormone releaser in humans. Ghrelin administered in vivo, in what were probably pharmacological doses, induced a significant secretion of prolactin and ACTH/cortisol. Ghrelin also has been reported to activate pit-1 expression in anterior pituitary cells in infant rats. Ghrelin administration in humans induces a sensation of hunger in 75% of the subjects tested, and is the most powerful appetite stimulant of all known peptides. Ghrelin also may be involved in the neuroendocrine and behavioral response to stress. Ghrelin and its functional receptor in testicular tissue have been shown to inhibit testosterone secretion, as well as in both the rat and human ovary, suggesting that ghrelin may be partly responsible for energy homeostasis associated with reproduction control. Ghrelin mRNA and ghrelin receptor mRNAs are expressed in gastric, thyroid, breast and lung neoplasias. Recent data also suggests that ghrelin may promote sleep. Finally, ghrelin and des-acyl ghrelin (a non-octanoyl-modified form of ghrelin) have been shown to inhibit cell death in cardiomyocyte and endothelial cells, indicating that ghrelin and its deacylated analog may have protective actions on the cardiovascular system. (Casanueva et al.)

Ghrelin is the most potent endogenous peptide known to stimulate gastric motility. However, the ghrelin peptide has limited utility as a therapeutic product due to its short pharmacokinetic half-life, poor oral bioavailability, and potent growth hormone-releasing activity. Thus, synthetic compounds, such as certain embodiments of the disclosed macrocycles, that act as ghrelin agonists without these disadvantages may find utility in promoting gastrointestinal motility and for treating postoperative ileus, diabetic gastroparesis, wasting syndrome, and other GI disorders involving dysmotility. Ghrelin agonists are also of interest in treating conditions caused by growth hormone deficiency. Ghrelin antagonists have been investigated for treatment of obesity.

Particular embodiments of the disclosed compounds may possess biological activity against a broad range of other targets, including targets with therapeutic indications. A macrocycle may enhance binding affinity, target selectivity, and/or metabolic stability, compared with its open-chain analog. Macrocycles can have high affinity and selectivity for targets, while having sufficient bioavailability due to their small size to reach intracellular locations. However, macrocycles form just a small percentage of available drugs. Existing macrocyclic drugs include compounds useful against infections, cancer, and other indications. Examples include rapamycin (an immunosuppressant drug used to prevent rejection in organ transplantation), temsirolimus (a drug for the treatment of renal cell carcinoma), fidaxomicin (an antibiotic with activity against gram-positive bacteria, including intestinal *C. difficile*), and ivermectin (an antiparasitic used to treat animals). Certain compounds disclosed herein antagonize the production of pro-inflammatory cytokines. Such compounds are useful in treating a variety of inflammatory and autoimmune conditions, examples of which are discussed below. In one aspect, certain compounds inhibit IL-23 production. The pro-inflammatory effect of IL-23 has been well documented and anti-IL-23 antibody therapy currently is being used in the treatment of various inflammatory and autoimmune disorders. In certain embodiments the disclosed compounds inhibit IL-23 production in response to an inflammatory stimulus. IL-23 inhibitory compounds disclosed herein may inhibit IL-23 production with an inhibitory concentration ($IC_{50}$) value of less than about 0.01 μM, or even less than about 1 nM, to about 20 μM, such as from about 0.1 μM to about 10 μM or from about 0.05 μM to about 1 μM.

Methods disclosed herein involve administering to a subject suffering from an inflammatory or autoimmune disease or at risk of developing such disease an amount of a disclosed compound effective to treat or prevent the disease and/or one or more associated symptoms. Examples of inflammatory or autoimmune diseases that can be treated or prevented with the disclosed compounds include respiratory disorders (including asthma, COPD, chronic bronchitis and cystic fibrosis); cardiovascular related disorders (including atherosclerosis, post-angioplasty, restenosis, coronary artery diseases and angina); inflammatory diseases of the joints (including rheumatoid and osteoarthritis); skin disorders (including dermatitis, eczematous dermatitis and psoriasis); post transplantation late and chronic solid organ rejection; multiple sclerosis. Conditions that also can be treated or prevented using the disclosed compounds also include those diseases that are commonly associated with nonanaphylactic hypersensitivity reactions (Type II, Type III and/or Type IV hypersensitivity reactions) and/or those diseases that are mediated, at least in part, by activation of the FcγR signaling cascade in monocyte cells. Such autoimmune disease include, but are not limited to, those autoimmune diseases that are frequently designated as single organ or single cell-type autoimmune disorders and those autoimmune disease that are frequently designated as involving systemic autoimmune disorder. Non-limiting examples of diseases frequently designated as single organ or single cell-type autoimmune disorders include: Hashimoto's thyroiditis, autoimmune hemolytic anemia, autoimmune atrophic gastritis of pernicious anemia, autoimmune encephalomyelitis, autoimmune orchitis, Goodpasture's disease, autoimmune thrombocytopenia, sympathetic ophthalmia, myasthenia gravis, Graves' disease, primary biliary cirrhosis, chronic aggressive hepatitis, ulcerative colitis and membranous glomerulopathy. Non-limiting examples of diseases often designated as involving systemic autoimmune disorder include: systemic lupus erythematosis, rheumatoid arthritis, Sjogren's syndrome, Reiter's syndrome, polymyositis-dermatomyositis, systemic sclerosis, polyarteritis nodosa, multiple sclerosis and bullous pemphigoid.

VI. Pharmaceutical Compositions

Embodiments of the disclosed macrocycles may be used in a variety of in vitro, in vivo and ex vivo contexts to promote gastrointestinal motility and/or to treat postoperative ileus and/or diabetic gastroparesis. The macrocycles may be administered singly, as mixtures of one or more macrocycles or in mixture or combination with other agents useful for treating such conditions and/or the symptoms associated with such conditions. The macrocycles may also be administered in mixture or in combination with agents useful to treat other disorders or maladies. In some embodiments, the macrocycles are administered as pharmaceutical compositions, comprising a macrocycle.

Pharmaceutical compositions comprising embodiments of the disclosed macrocycles may be manufactured by means of conventional mixing, dissolving, granulating, dragee-making levigating, emulsifying, encapsulating, entrapping or lyophilization processes. The compositions may be formulated in conventional manner using one or more physiologically acceptable carriers, diluents, excipients or auxiliaries which facilitate processing of the macrocycles into preparations which can be used pharmaceutically.

The macrocycle may be used to form a pharmaceutical composition. The pharmaceutical composition may comprise the macrocycle itself. Alternatively, the macrocycle may be a hydrate, a solvate, a pharmaceutically acceptable salt, or combinations thereof. Typically, pharmaceutically acceptable salts more soluble in aqueous solutions than the corresponding free acids and bases from which the salts are produced; however, salts having lower solubility than the corresponding free acids and bases from which the salts are produced may also be formed. Pharmaceutically acceptable salts are typically counterbalanced with an inorganic base, organic base, or basic amino acid if the salts are positively charged; or the salt is counterbalanced with an inorganic acid, organic acid, or acidic amino acid if they are negatively charged. Pharmaceutically acceptable salts can also be zwitterionic in form. Salts can be formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide. Other elements capable of forming salts are well-known to those skilled in the art, e.g. all elements from the main groups I to V of the Periodic Table of the Elements, as well as the elements from the subgroups I to VIII. Any chemical compound recited in this specification may alternatively be administered as a pharmaceutically acceptable salt thereof. "Pharmaceutically acceptable salts" are also inclusive of the free acid, base, and. Descriptions of suitable pharmaceutically acceptable salts can be found in *Handbook of Pharmaceutical Salts, Properties, Selection and Use*, Wiley VCH (2002), which we herein incorporate by reference.

Pharmaceutical compositions of the invention may take a form suitable for virtually any mode of administration, including, for example, topical, ocular, oral, buccal, systemic, nasal, injection, transdermal, rectal, vaginal, etc., or a form suitable for administration by inhalation or insufflation.

For topical administration, the macrocycle(s) may be formulated as solutions, gels, ointments, creams, suspensions, etc. as are well-known in the art.

Systemic formulations include those designed for administration by injection, e.g., subcutaneous, intravenous, intramuscular, intrathecal or intraperitoneal injection, as well as those designed for transdermal, transmucosal oral or pulmonary administration.

Useful injectable preparations include sterile suspensions, solutions or emulsions of the macrocycle(s) in aqueous or oily vehicles. The compositions may also contain formulating agents, such as suspending, stabilizing and/or dispersing agents. The formulations for injection may be presented in unit dosage form, e.g., in ampules or in multidose containers, and may contain added preservatives.

Alternatively, the injectable formulation may be provided in powder form for reconstitution with a suitable vehicle, including but not limited to sterile pyrogen-free water, buffer, dextrose solution, etc., before use. To this end, the macrocycle(s) may be dried by any art-known technique, such as lyophilization, and reconstituted prior to use.

For transmucosal administration, penetrants appropriate to the barrier to be permeated are used in the formulation. Such penetrants are known in the art.

For oral administration, the pharmaceutical compositions may take the form of, for example, lozenges, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets may be coated by methods well known in the art with, for example, sugars, films or enteric coatings.

Liquid preparations for oral administration may take the form of, for example, elixirs, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol, Cremophore™ or fractionated vegetable oils); and preservatives (e.g., methyl or propyl-p-hydroxybenzoates or sorbic acid). The preparations may also contain buffer salts, preservatives, flavoring, coloring and sweetening agents as appropriate.

Preparations for oral administration may be suitably formulated to give controlled release of the macrocycle, as is well known.

For buccal administration, the compositions may take the form of tablets or lozenges formulated in conventional manner.

For rectal and vaginal routes of administration, the macrocycle(s) may be formulated as solutions (for retention enemas) suppositories or ointments containing conventional suppository bases such as cocoa butter or other glycerides.

For nasal administration or administration by inhalation or insufflation, the macrocycle(s) can be conveniently delivered in the form of an aerosol spray from pressurized packs or a nebulizer with the use of a suitable propellant, e.g., dichlorodifluoromethane, trichlorofluoromethane, dichlorotetrafluoroethane, fluorocarbons, carbon dioxide or other suitable gas. In the case of a pressurized aerosol, the dosage unit may be determined by providing a valve to deliver a metered amount. Capsules and cartridges for use in an inhaler or insufflator (for example capsules and cartridges comprised of gelatin) may be formulated containing a powder mix of the macrocycle and a suitable powder base such as lactose or starch.

For ocular administration, the macrocycle(s) may be formulated as a solution, emulsion, suspension, etc. suitable for administration to the eye. A variety of vehicles suitable for administering macrocycles to the eye are known in the art. Specific non-limiting examples are described in U.S. Pat. Nos. 6,261,547; 6,197,934; 6,056,950; 5,800,807; 5,776,445; 5,698,219; 5,521,222; 5,403,841; 5,077,033; 4,882,150; and 4,738,851.

For prolonged delivery, the macrocycle(s) can be formulated as a depot preparation for administration by implantation or intramuscular injection. The active ingredient may be formulated with suitable polymeric or hydrophobic materials (e.g., as an emulsion in an acceptable oil) or ion exchange resins, or as sparingly soluble derivatives, e.g., as a sparingly soluble salt. Alternatively, transdermal delivery systems manufactured as an adhesive disc or patch which slowly releases the macrocycle(s) for percutaneous absorption may be used. To this end, permeation enhancers may be used to facilitate transdermal penetration of the macrocycle(s). Suitable transdermal patches are described in, for example, U.S. Pat. Nos. 5,407,713; 5,352,456; 336,213; 5,336,168; 5,290,561; 5,254,346; 5,164,189; 5,163,899; 5,088,977; 5,087,240; 5,008,110; and 4,921,475.

Alternatively, other pharmaceutical delivery systems may be employed. Liposomes and emulsions are well-known examples of delivery vehicles that may be used to deliver macrocycle(s). Certain organic solvents such as dimethylsulfoxide (DMSO) may also be employed, although usually at the cost of greater toxicity.

The pharmaceutical compositions may, if desired, be presented in a pack or dispenser device which may contain one or more unit dosage forms containing the macrocycle(s). The pack may, for example, comprise metal or plastic foil, such as a blister pack. The pack or dispenser device may be accompanied by instructions for administration.

VII. Effective Dosages

Embodiments of the disclosed macrocycle(s), or compositions thereof, will generally be used in an amount effective to achieve the intended result, for example in an amount effective to treat or prevent the particular condition being treated. The macrocycle(s) may be administered therapeutically to achieve therapeutic benefit or prophylactically to achieve prophylactic benefit. By therapeutic benefit is meant eradication or amelioration of the underlying disorder being treated and/or eradication or amelioration of one or more of the symptoms associated with the underlying disorder such that the patient reports an improvement in feeling or condition, notwithstanding that the patient may still be afflicted with the underlying disorder. For example, administration of a macrocycle to a patient suffering from gastroparesis provides therapeutic benefit not only when the gastroparesis is ameliorated, but also when the patient reports a decrease in the severity or duration of the symptoms associated with the gastroparesis.

For prophylactic administration, the macrocycle may be administered to a patient at risk of developing gastroparesis or postoperative ileus. For example, the macrocycle may be administered prior to surgery to avoid or ameliorate a postoperative ileus. Macrocycles may also be administered prophylactically to diabetic individuals to prevent the onset of the gastroparesis.

The amount of macrocycle administered will depend upon a variety of factors, including, for example, the particular indication being treated, the mode of administration, whether the desired benefit is prophylactic or therapeutic, the severity of the indication being treated and the age and weight of the patient, the bioavailability of the particular macrocycle, etc. Determination of an effective dosage is well within the capabilities of those skilled in the art.

Effective dosages may be estimated initially from in vitro assays. For example, an initial dosage for use in animals may be formulated to achieve a circulating blood or serum concentration of macrocycle that is at or above an $IC_{50}$ of the particular macrocycle as measured in an in vitro assay. Calculating dosages to achieve such circulating blood or serum concentrations taking into account the bioavailability of the particular macrocycle is well within the capabilities of skilled artisans. For guidance, the reader is referred to Fingl & Woodbury, "General Principles," In: Goodman and Gilman's The Pharmaceutical Basis of Therapeutics, Chapter 1, latest edition, Pagamonon Press, and the references cited therein.

Initial dosages can also be estimated from in vivo data, such as animal models. Animal models useful for testing the efficacy of macrocycles to treat or prevent the various conditions described above are well-known in the art. Ordinarily skilled artisans can routinely adapt such information to determine dosages suitable for human administration.

Dosage amounts will typically be in the range of from about 0.0001 or 0.001 or 0.01 mg/kg/day to about 100 mg/kg/day, but may be higher or lower, depending upon, among other factors, the activity of the macrocycle, its bioavailability, the mode of administration and various factors discussed above. Dosage amount and interval may be adjusted individually to provide plasma levels of the macrocycle(s) which are sufficient to maintain therapeutic or prophylactic effect. For example, the macrocycles may be administered once per week, several times per week (e.g., every other day), once per day or multiple times per day, depending upon, among other things, the mode of administration, the specific indication being treated and the judgment of the prescribing physician.

Preferably, the macrocycle(s) will provide therapeutic or prophylactic benefit without causing substantial toxicity. Toxicity of the macrocycle(s) may be determined using standard pharmaceutical procedures. The dose ratio between toxic and therapeutic (or prophylactic) effect is the therapeutic index. Macrocycles(s) that exhibit high therapeutic indices are preferred.

VIII. Examples

All moisture sensitive reactions were carried out under Nitrogen. Anhydrous solvents were purchased from Aldrich. All other solvents were HPLC grade. Column chromatography was performed with EMD Merck silica gel (0.040-0.63 μm, 240-400 mesh) under low pressure of 5-10 psi. Flash chromatography was carried out on a Teledyne Isco CombiFlash Rf flash system with variable solvent gradients. TLC analysis was performed with E. Merck silica gel 60-F254 plates. NMR spectra were recorded on a Varian Mercury VX 300 MHz spectrometer. NMR spectra measured in $CDCl_3$ solutions were referenced to the residual $CHCl_3$ signal ($^1H$, δ=7.26; $^{13}C$, δ=77.0); spectra measured in DMSO-$d_6$ were referenced to the residual DMSO signal ($^1H$, δ=2.50; $^{13}C$, δ=39.50). $^1H$ and $^{13}C$ shifts are given in ppm (s=singlet, d=doublet, t=triplet, q=quadruplet, quin=quintet, m=multiplet, br s=broad signal). Coupling constants, J, are given in Hz. Mass spectra were measured on a Waters Micromass ZQ or ZMD instrument.

Example 1

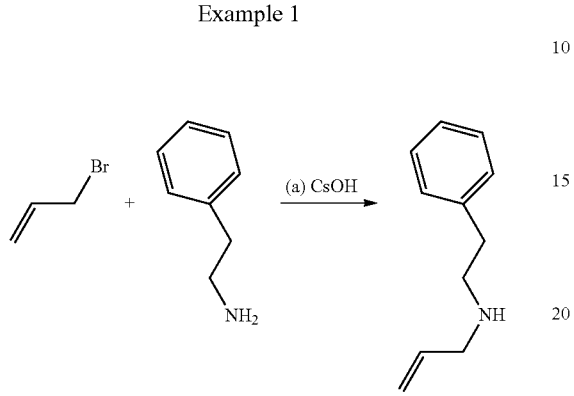

This compound was synthesized using a modified procedure described by Jung et al[3], which we herein incorporate by reference. Phenylethylamine (50.0 g, 413 mmol), CsOH.H$_2$O (6.93 g, 41.3 mmol) and activated 4 Å molecular sieves (20 g) were combined with dry DMF (300 ml) and stirred at room temperature for 30 minutes. The mixture was cooled to −20° C. using a NaCl/ice bath. Then allyl bromide (50.0 g, 423 mmol) was added very slowly dropwise. The reaction mixture was allowed to warm to room temperature over night. Most of the solvent was removed in vacuo and sat. NaHCO$_3$ (400 ml) was added to the crude product. The mixture was extracted with Et$_2$O (3×), the combined organic layers were dried over MgSO$_4$ and solvents were evaporated under reduced pressure. Analysis by TLC (3% MeOH [2M NH$_3$] in CHCl$_3$) and HPLC showed that the mono- and di-allylated products had been formed in roughly the same amounts. The desired product was isolated by flash chromatography eluting with 3% MeOH [2M NH$_3$] in CHCl$_3$. The mono-allylated compound was obtained in 52% yield (34.5 g) in form of a pale yellow oil. $^1$H NMR (300 MHz, DMSO) δ 7.28-7.10 (m, 5H), 5.96-5.65 (m, 1H), 5.11 (d, J=17.2 Hz, 1H), 5.00 (d, J=10.2 Hz, 1H), 3.15 (d, J=5.8 Hz, 2H), 2.70 (s, 4H), 1.60 (s br, 1H) ppm; MS (ESI) (m/z): 162 [M+H]$^+$, 146, 119.

Example 2

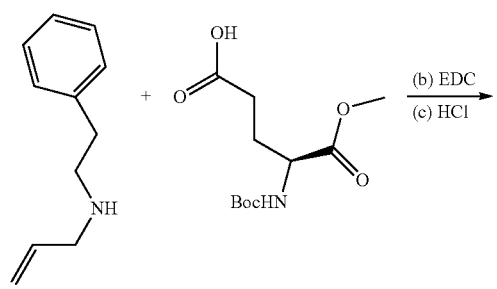

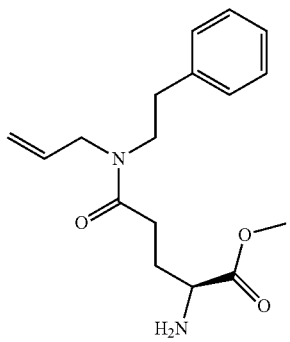

A Boc-protected glutamic methyl ester, (2.73 g, 10.4 mmol), EDC (3.00 g, 15.7 mmol), HOBt (2.11 g, 15.7 mmol) and Et$_3$N (2.9 ml, 20.8 mmol) were dissolved in dry DCM (150 ml). The mixture was stirred for 15 minutes and the allyl amine was subsequently added to the reaction mixture. Stirring was continued over night at room temperature. The reaction mixture was then concentrated in vacuo and further purified by flash chromatography eluting with chloroform/methanol (20/1). The Boc-protected amide was obtained in form of a clear yellowish oil in 94% yield (3.95 g). $^1$H NMR (300 MHz, DMSO) δ 7.35-7.12 (m, 5H), 5.87-5.59 (m, 1H), 5.11 (d, J=11.5 Hz, 1H), 5.04 (d, J=10.5 Hz, 1H), 4.06-3.91 (m, 1H), 3.85 (d, J=19.7 Hz, 2H), 3.60 (s, 3H), 3.44-3.29 (m, 2H), 2.75 (m, 2H), 2.43-2.20 (m, 2H), 1.90 (m, 1H), 1.72 (m, 1H), 1.34 (d, J=7.2 Hz, 9H) ppm; MS (ESI) (m/z): 405 [M+H]$^+$, 349, 305.

The product from the above reaction was dissolved in methanol (100 ml) and HCl (20 ml, 4M in dioxane) was added via syringe. The mixture was stirred at room temperature until analysis by TLC showed complete conversion (1 d). After neutralizing with 1M NaOH (80 ml), the mixture was extracted with Et$_2$O (2×) and EtOAc (2×). The combined organic layers were dried over Na$_2$SO$_4$ and solvents were removed under reduced pressure to give 2.91 g (98%) the deprotected amide.

Example 3

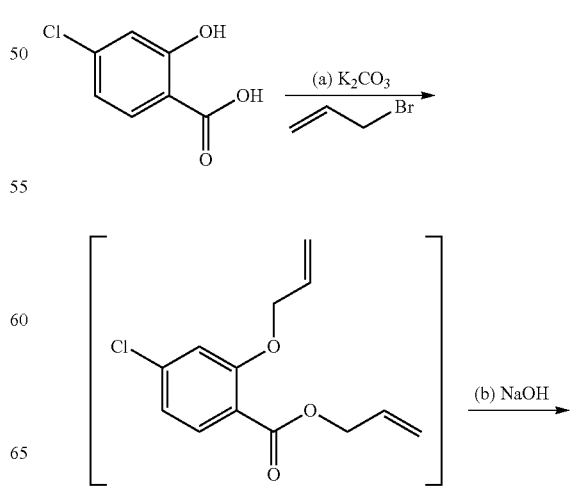

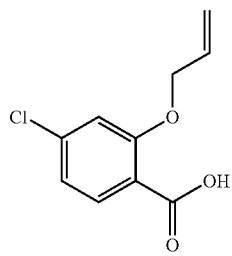

A salicylic acid derivative (30.0 g, 174 mmol) and allyl bromide (84.1 g, 696 mmol) were dissolved in acetone (500 ml). $K_2CO_3$ (72.1 g, 522 mmol) and $Cs_2CO_3$ (5.67 g, 17.4 mmol) were added and the reaction mixture was refluxed for 8 hours. Salts were filtered off and the acetone was removed under reduced pressure. Excess allyl bromide was removed by applying high vacuum to the rotary evaporator. The yellowish crude oil was dissolved in ethanol (250 ml) and 2M NaOH (104 ml, 208 mmol) was added. The mixture was stirred over night at room temperature and then acidified (ice-bath cooling) using concentrated HCl. The carboxylic acid product was precipitated by adding ice water and keeping the flask in the refrigerator for several hours. The product was obtained in form of a solid and collected by filtration (34.7 g, 94%). $^1$H NMR (300 MHz, DMSO) δ 7.65 (d, J=8.3 Hz, 1H), 7.16 (s, 1H), 7.03 (d, J=8.3 Hz, 1H), 6.12-5.88 (m, 1H), 5.46 (d, J=17.3 Hz, 1H), 5.23 (d, J=10.6 Hz, 1H), 4.64 (d, J=4.7 Hz, 2H) ppm; $^{13}$C NMR (75 MHz, DMSO) δ 167.13, 158.52, 137.90, 133.56, 132.94, 120.87, 117.81, 114.64, 69.59 ppm; MS (ESI) (m/z): 213 [M+H]$^+$, 195, 167, 157.

Example 4

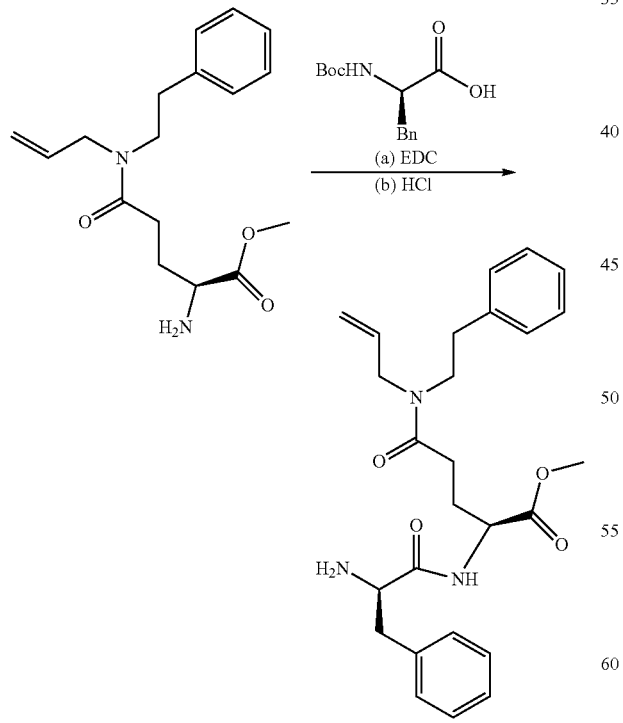

D-Phenylalanine (2.48 g, 9.35 mmol), EDC (2.69 g, 14.0 mmol), HOBt (1.89 g, 14.0 mmol) and $Et_3N$ (2.60 ml, 18.7 mmol) were dissolved in dry DCM (150 ml). The mixture was stirred for 30 minutes and the glutamic amino methyl ester, (2.84 g, 9.35 mmol) was subsequently added to the reaction mixture. Stirring was continued over night at room temperature. The reaction mixture was then concentrated in vacuo and further purified by flash chromatography eluting with chloroform/methanol (40/1). The Boc-protected amide was obtained in form of a pale yellow oil in 78% yield (4.02 g). $^1$H NMR (300 MHz, DMSO) δ 8.35 (d, J=7.6 Hz, 1H), 7.33-7.07 (m, 10H), 6.87 (d, J=8.7 Hz, 1H), 5.73 (tdt, J=15.8, 10.4, 5.3 Hz, 1H), 5.09 (m, 2H), 4.25 (m, 2H), 3.89 (d, J=5.2 Hz, 1H), 3.80 (d, J=4.0 Hz, 1H), 3.61 (s, 3H), 3.37 (d, J=6.5 Hz, 2H), 2.99-2.84 (m, 1H), 2.83-2.61 (m, 3H), 2.24 (m, 2H), 1.92 (td, J=13.8, 6.3 Hz, 1H), 1.84-1.66 (m, 1H), 1.27 (s, 9H) ppm; $^{13}$C NMR (75 MHz, DMSO) δ 172.83, 172.34, 171.53, 171.11, 139.84, 139.18, 129.82, 129.41, 129.24, 129.01, 128.57, 126.79, 117.18, 116.69, 79.89, 78.66, 56.25, 52.62, 50.65, 47.88, 38.67, 35.09, 34.31, 28.91, 27.54 ppm; MS (ESI) (m/z): 552 [M+H]$^+$, 496, 452.

The product from the above reaction was dissolved in methanol (120 ml) and HCl (20 ml, 4M in dioxane) was added via syringe. The mixture was stirred at room temperature until analysis by TLC showed complete conversion (1 d). After neutralization with 1M NaOH (80 ml) the mixture extracted with $Et_2O$ (2×) and EtOAc (2×). The combined organic layers were passed though a plug of $MgSO_4$ to remove residual water and solvents were removed under reduced pressure to furnish 2.99 g (91%) of the desired amide.

Example 5

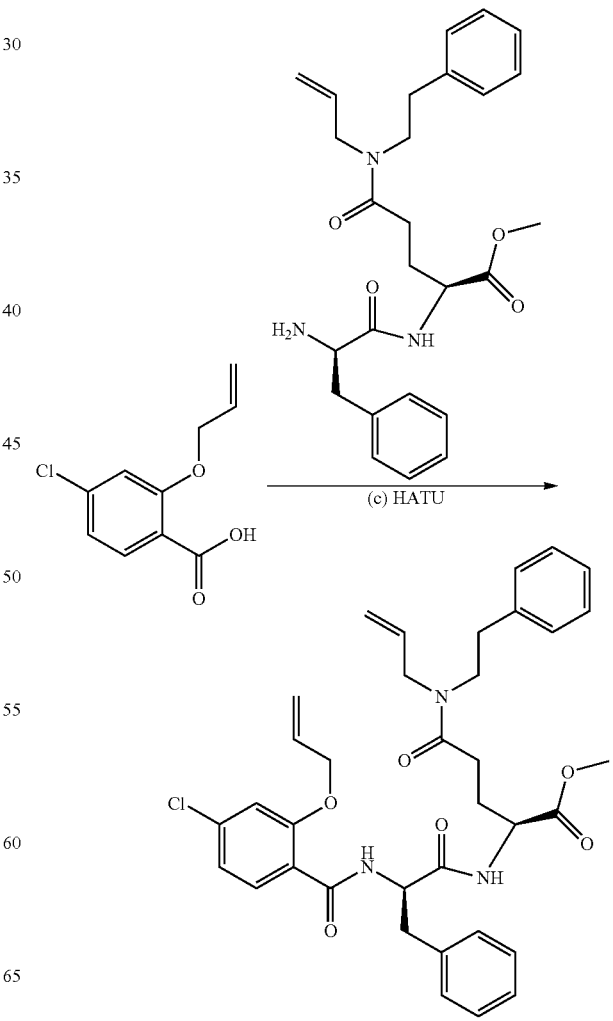

The salicylic acid derivative (0.735 g, 3.45 mmol), HATU (1.57 g, 4.14 mmol) and Et₃N (1.05 ml, 7.59 mmol) were dissolved in dry DMF (50 ml). The mixture was stirred for 30 minutes and the amide product from Example 4 (1.56 g, 3.45 mmol) was subsequently added to the reaction mixture. Stirring was continued over night at room temperature. The reaction mixture was then concentrated in vacuo and further purified by flash chromatography eluting with chloroform/methanol (30/1). The desired acyclic precursor was obtained in form of a pale yellow oil in 73% yield (1.63 g). ¹H NMR (300 MHz, CDCl₃) δ 8.25 (d, J=7.8 Hz, 1H), 8.08 (dd, J=7.8, 3.8 Hz, 1H), 7.35-7.04 (m, 11H), 6.99 (d, J=8.8 Hz, 1H), 6.87 (s, 1H), 5.92 (m, 1H), 5.62 (m, 1H), 5.33 (dd, J=17.2, 9.8 Hz, 2H), 5.12 (dd, J=18.4, 10.6 Hz, 2H), 4.95 (m, 1H), 4.55 (m, 4H), 4.32 (m, 1H), 3.67 (s, 3H), 3.51-3.33 (m, 3H), 3.21 (d, J=6.8 Hz, 2H), 2.78 (m, 3H), 2.38-2.07 (m, 1H), 2.06-1.83 (m, 1H) ppm; ¹³C NMR (75 MHz, CDCl₃) δ 172.19, 171.79, 171.05, 167.44, 164.42, 157.22, 139.24, 138.73, 138.25, 136.93, 133.54, 132.86, 131.64, 129.51, 128.95, 128.71, 127.00, 126.50, 121.83, 119.77, 116.94, 113.68, 70.65, 55.17, 52.63, 51.12, 48.69, 38.26, 35.20, 34.39, 29.30, 27.17 ppm; MS (ESI) (m/z): 646 [M+H]⁺, 305.

Example 6

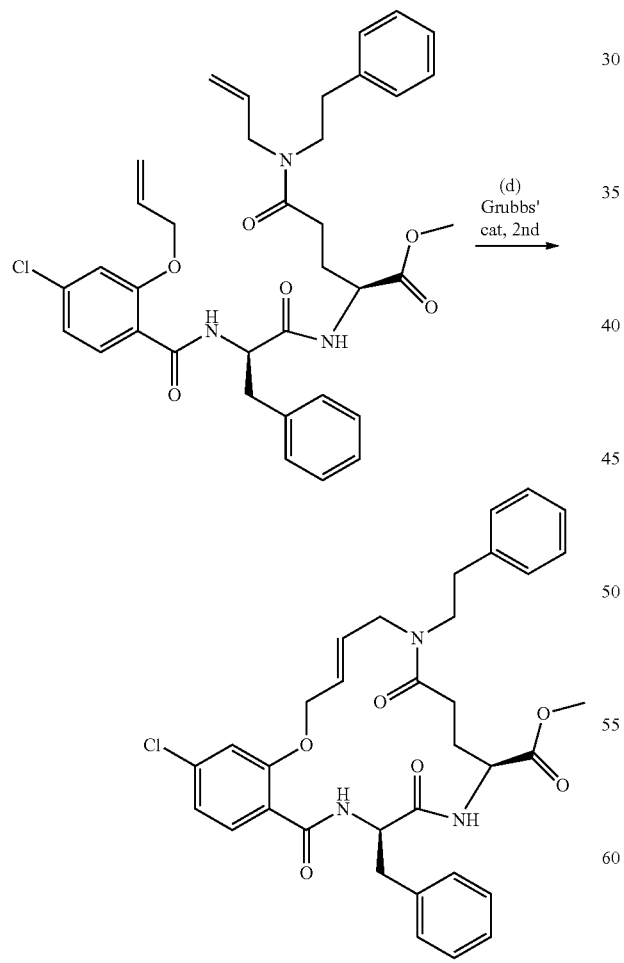

The acyclic precursor from Example 5 (758 mg, 1.17 mmol) was dissolved in dry DCM (200 ml, c≈0.006 mol/L); the solution was degassed and flushed with N₂ (3×). Grubbs' II catalyst (80.0 mg, 0.091 mmol) dissolved in dry DCM (20 ml) was added dropwise over a period of five minutes. Stirring was continued for 8 hours at room temperature. The clear, peach-colored solution turned dark-blackish within a couple of hours. Water (30 ml) was added to deactivate the catalyst; the organic layer was separated and filtered through a plug of MgSO₄. Solvents were removed under reduced pressure and the crude product was purified by column chromatography eluting with chloroform/methanol (30/1). The product (dark oil, 644 mg, 89%) was obtained as a mixture of E/Z-isomers in a ratio of 78/22 (determined by LCMS). The geometric isomers were separated by preparative HPLC to allow spectroscopic characterization. The final compounds were obtained in form of white solids.

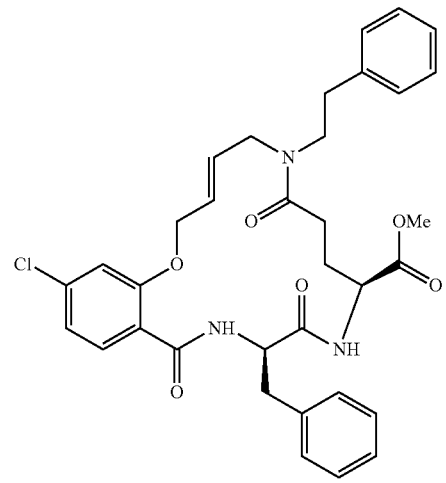 [SMILES: COC(=O)[C@@H]1CCC(=O)N(CCc2ccccc2)C/C=C/COc2cc(Cl)ccc2C(=O)N[C@H](Cc2ccccc2)C(=O)N1]

(E-Isomer) ¹H NMR (300 MHz, DMSO) δ 8.30 (d, J=8.8 Hz, 1H), 7.76 (d, J=8.4 Hz, 1H), 7.32-7.05 (m, 11H), 5.63 (d, J=15.3 Hz, 1H), 5.44 (d, J=15.3 Hz, 1H), 4.84 (d, J=3.7 Hz, 1H), 4.59 (s, 1H), 4.55-4.46 (m, 1H), 4.45-4.25 (m, 2H), 4.09-3.95 (m, 1H), 3.66 (d, J=7.3 Hz, 1H), 3.62 (s, 3H), 3.24 (dd, J=13.7, 5.3 Hz, 1H), 3.05 (dd, J=13.0, 6.6 Hz, 1H), 2.96 (dd, J=13.3, 4.5 Hz, 1H), 2.70 (s, 2H), 2.14 (d, J=13.2 Hz, 2H), 1.94-1.69 (m, 2H) ppm; ¹³C NMR (75 MHz, CDCl₃) δ 172.49, 171.59, 170.24, 164.12, 157.26, 139.24, 139.14, 136.56, 133.44, 130.51, 130.37, 128.96, 128.71, 128.60, 127.15, 126.56, 124.18, 121.93, 119.62, 112.83, 69.18, 53.92, 53.01, 52.29, 49.06, 48.66, 37.30, 34.20, 28.49, 28.07 ppm; MS (ESI) (m/z): 618 [M+H]⁺.

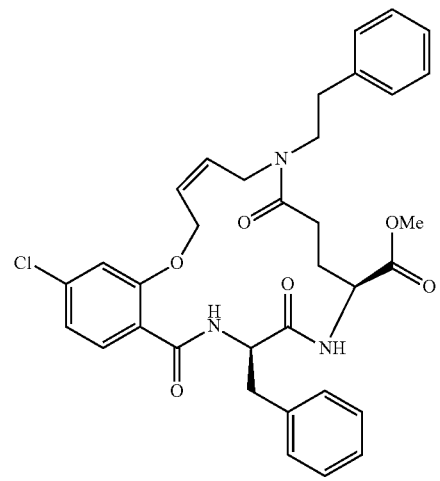 [SMILES: COC(=O)[C@@H]1CCC(=O)N(CCc2ccccc2)C/C=C\COc2cc(Cl)ccc2C(=O)N[C@H](Cc2ccccc2)C(=O)N1]

(Z-Isomer) ¹H NMR (300 MHz, CDCl₃) δ 8.49 (d, J=4.0 Hz, 1H), 8.31 (d, J=8.3 Hz, 1H), 8.18 (d, J=8.5 Hz, 1H), 7.36-7.17 (m, 10H), 7.04 (d, J=8.5 Hz, 1H), 6.98 (s, 1H), 5.62-5.47 (m, 2H), 5.04 (td, J=8.3, 4.8 Hz, 1H), 4.81 (t, J=9.5 Hz, 1H), 4.56 (dd, J=14.4, 9.8 Hz, 1H), 4.49-4.41 (m, 1H), 4.32 (s, 1H), 3.77 (s, 3H), 3.52 (m, 2H), 3.20 (dd, J=14.5, 4.6 Hz, 1H), 3.07 (m, 2H), 2.85 (t, J=7.3 Hz, 2H), 2.38-2.10 (m, 2H), 2.03 (dd, J=16.1, 6.0 Hz, 1H), 1.88 (dd, J=13.5, 5.5 Hz, 1H) ppm; ¹³C NMR (75 MHz, CDCl₃) δ 172.90, 172.61, 171.99, 164.55, 158.05, 138.91, 137.79, 137.40, 134.06, 130.33, 129.65, 129.16, 128.89, 128.69, 127.29, 126.90, 124.78, 122.00, 119.26, 113.51, 64.19, 55.11, 53.12, 52.27, 51.49, 45.01, 38.55, 35.57, 28.88, 23.23 ppm; MS (ESI) (m/z): 618 [M+H]⁺.

Analysis of the product by HPLC and NMR revealed that a 78/22 mixture of E/Z isomers had been formed in the ring closing metathesis reaction.[5] The main isomer was assigned as the E-isomer based on the large coupling constant (J=15.3 Hz) indicative for a trans double bond geometry.

Other embodiments of this reaction can be carried out on different acyclic precursors. Similarly substituted RCM precursors (Table 1, entries B, C, D; prepared using the synthetic route as described above) were subjected to the same metathesis conditions and it was found that the E/Z ratio of the products was fairly independent from the substitution pattern (Table 1). In all four examples, the E/Z ratio was in the same range (E/Z≈4/1 to 3/1). In entries B, C and D of Table 1 the E-isomer was commercially available from AnalytiCon. The main isomer observed in the RCM reaction gave an exact match in retention time on HPLC [HPLC was performed on an Agilent Zorbax SB-C18 2.1×150 mm (5 μm) column] compared to the commercial E-isomer purchased from AnalytiCon (e.g. for entry B, E-isomer: $t_R$ (Rigel)=10.70 min vs. $t_R$ (AnalytiCon)=10.70 min). These findings further confirmed the assignment of the double bond geometry. Characterization data for selected macrocycles found in Table 1 are provided.

| Entry | RCM Precursor | E-Isomer | E/Z Ratio | Z-Isomer |
|---|---|---|---|---|
| A | | | 78/22 | |
| B | | | 68/32 | |
| C | | | 72/28 | |

-continued

| Entry | RCM Precursor | E-Isomer | E/Z Ratio | Z-Isomer |
|---|---|---|---|---|
| D | 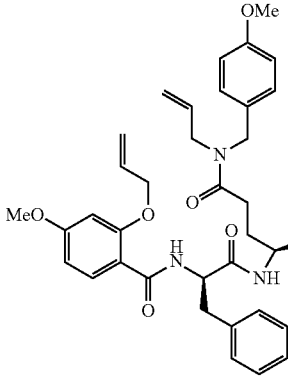 | 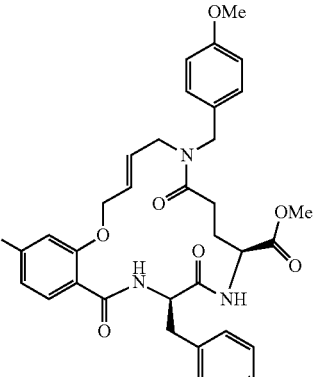 | 73/27 | 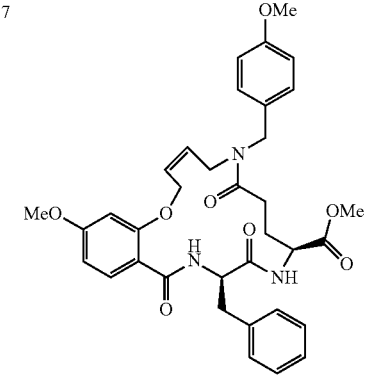 |

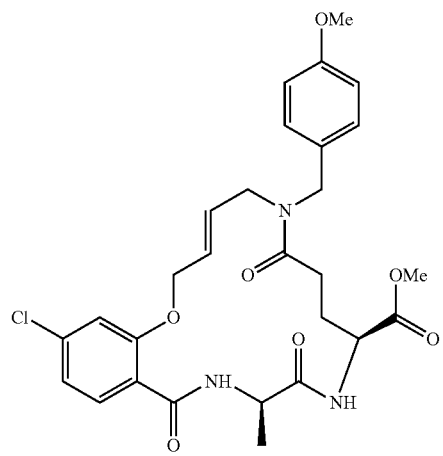 [SMILES: COC(=O)[C@@H]1CCC(=O)N(Cc2ccc(OC)cc2)C/C=C/COc2cc(Cl)ccc2C(=O)N[C@H](C)C(=O)N1]

Entry B, (E-Isomer) ¹H NMR (300 MHz, DMSO) δ 8.34 (d, J=7.7 Hz, 1H), 8.24 (d, J=7.7 Hz, 1H), 7.77 (d, J=8.3 Hz, 1H), 7.27 (s, 1H), 7.20-7.03 (m, 3H), 6.86 (d, J=8.7 Hz, 2H), 5.97-5.69 (m, 2H), 4.84-4.57 (m, 3H), 4.53 (dd, J=14.4, 7.1 Hz, 1H), 4.36 (t, J=9.3 Hz, 1H), 4.15-3.88 (m, J=37.3 Hz, 2H), 3.71 (s, 3H), 3.60 (s, 4H), 2.40-2.07 (m, 4H), 1.91-1.68 (m, 1H), 1.34 (d, J=7.0 Hz, 3H) ppm; ¹³C NMR (75 MHz, DMSO) δ 172.52, 171.78, 163.98, 159.04, 157.42, 137.42, 132.78, 130.61, 129.90, 129.78, 126.64, 122.19, 121.46, 114.44, 113.97, 100.15, 69.69, 55.69, 52.63, 51.98, 49.72, 48.11, 47.90, 28.36, 26.83, 19.15 ppm; MS (ESI) (m/z): 558 [M+H]⁺, 333.

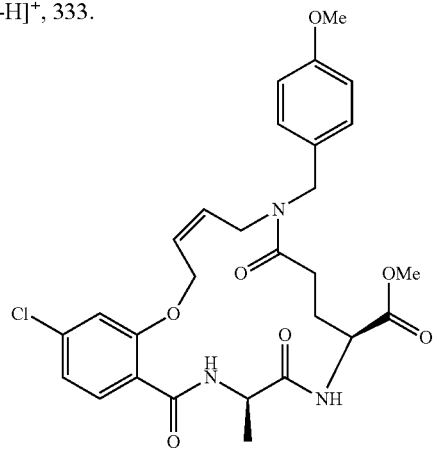

Entry B, (Z-Isomer) ¹H NMR (300 MHz, DMSO) δ 8.66-8.49 (m, 1H), 8.41 (d, J=7.9 Hz, 1H), 7.98 (t, J=8.1 Hz, 1H), 7.64 (d, J=8.3 Hz, 1H), 7.27 (s, 1H), 7.20-7.03 (m, 3H), 6.94-6.80 (m, 2H), 5.98-5.81 (m, 1H), 5.72 (dd, J=11.2, 5.9 Hz, 1H), 5.45 (dd, J=11.5, 5.8 Hz, 1H), 4.72 (s, 2H), 4.54-4.36 (m, 3H), 4.19 (dd, J=16.1, 9.1 Hz, 1H), 4.09-4.00 (m, 1H), 3.71 (s, 3H), 3.59 (s, 3H), 2.41-2.25 (m, 2H), 2.13-1.92 (m, 2H), 1.27 (d, J=7.1 Hz, 3H) ppm; ¹³C NMR (75 MHz, DMSO) δ 173.51, 172.85, 172.49, 171.97, 164.92, 159.07, 157.19, 136.88, 132.08, 130.46, 129.95, 129.09, 124.89, 123.72, 121.49, 114.50, 65.25, 55.69, 52.98, 52.57, 50.13, 48.89, 45.20, 29.31, 25.98, 18.44 ppm; MS (ESI) (m/z): 558 [M+H]⁺.

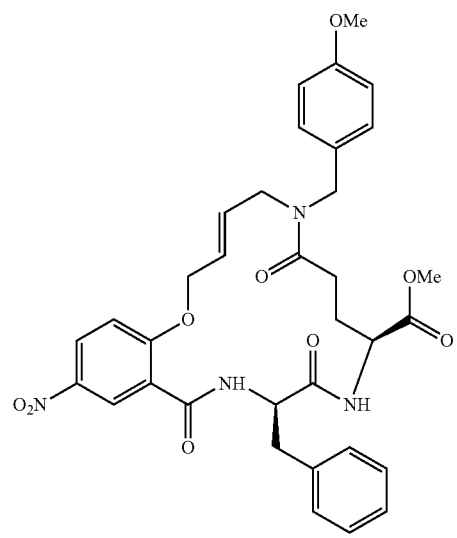 [SMILES: COC(=O)[C@@H]1CCC(=O)N(Cc2ccc(OC)cc2)C/C=C/COc2ccc([N+](=O)[O-])cc2C(=O)N[C@H](Cc2ccccc2)C(=O)N1]

Entry C, (E-Isomer) ¹H NMR (300 MHz, CDCl₃) δ 9.11 (s, 1H), 8.82 (d, J=6.9 Hz, 1H), 8.37 (d, J=9.1 Hz, 1H), 7.28-7.22 (m, J=3.1 Hz, 4H), 7.14 (d, J=8.6 Hz, 1H), 7.08 (d, J=9.2 Hz, 1H), 6.82 (d, J=8.7 Hz, 2H), 6.44 (d, J=7.2 Hz, 1H), 5.82-5.65 (m, 2H), 5.21 (d, J=14.6 Hz, 1H), 5.05 (d, J=6.3 Hz, 1H), 4.77 (t, J=12.5 Hz, 2H), 4.55 (dd, J=10.4, 5.9 Hz, 1H), 3.79 (s, 3H), 3.78 (s, 3H), 3.74-3.64 (m, 1H), 3.54-3.37 (m, 2H), 3.33-3.22 (m, 1H), 2.60-2.45 (t, J=11.7 Hz, 2H), 2.37-2.15 (m, 1H), 2.06 (d, J=17.8 Hz, 1H), 1.90-1.70 (m, 2H) ppm; MS (ESI) (m/z): 645 [M+H]⁺, 333.

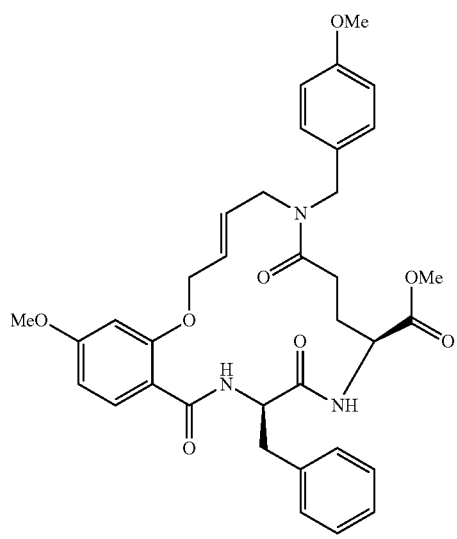 [SMILES: COC(=O)[C@@H]1CCC(=O)N(Cc2ccc(OC)cc2)C/C=C/COc2cc(OC)ccc2C(=O)N[C@H](Cc2ccccc2)C(=O)N1]
Entry D, (E-Isomer) $^1$H NMR (300 MHz, CDCl$_3$) δ 8.50 (d, J=7.8 Hz, 2H), 8.20 (d, J=8.8 Hz, 1H), 7.29-7.16 (m, 5H), 7.13 (d, J=8.5 Hz, 2H), 6.82 (d, J=8.6 Hz, 2H), 6.63 (dd, J=8.8, 2.1 Hz, 1H), 6.52 (d, J=7.1 Hz, 1H), 6.46 (s, 1H), 5.56 (d, J=14.1 Hz, 1H), 5.13 (d, J=14.6 Hz, 1H), 4.57 (dd, J=10.8, 4.4 Hz, 1H), 4.43 (dd, J=15.6, 7.6 Hz, 1H), 4.36 (dd, J=10.7, 6.2 Hz, 1H), 3.86 (s, 3H), 3.77 (s, 3H), 3.75 (s, 3H), 3.70-3.56 (m, 1H), 3.55-3.42 (m, 1H), 3.39 (dd, J=14.3, 3.6 Hz, 1H), 3.24 (d, J=5.4 Hz, 1H), 2.90 (s br, 2H), 2.62-2.38 (m, 1H), 2.17-2.01 (m, 1H), 1.97-1.68 (m, 2H) ppm; MS (ESI) (m/z): 630 [M+H]$^+$, 333.
Example 7
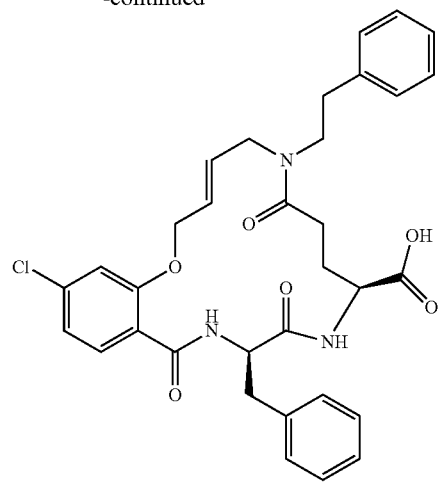
The ester moiety of the macrocycle (E-isomer) of Example 6 was hydrolyzed to the corresponding acid using NaOH in MeOH/H$_2$O (1:1) at room temperature over 12 h, in 94% yield.
Example 8
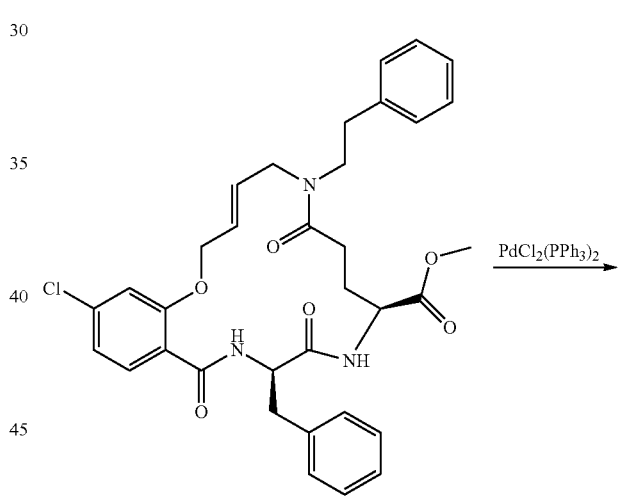
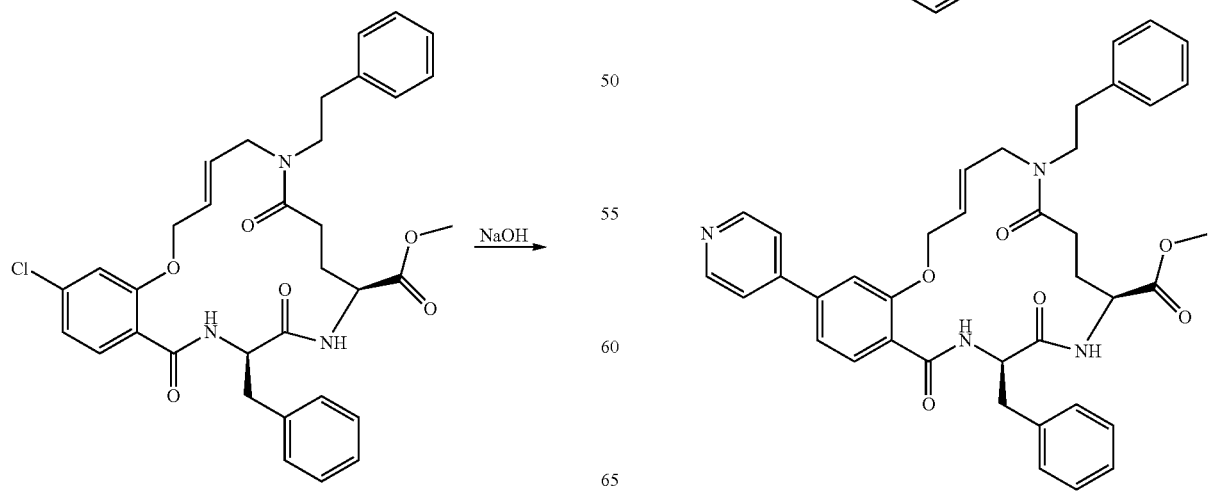

The macrocycle of Example 6 (E-isomer) was converted to a pyridine-containing biaryl derivative in 27% yield using standard Suzuki coupling conditions.

Example 9

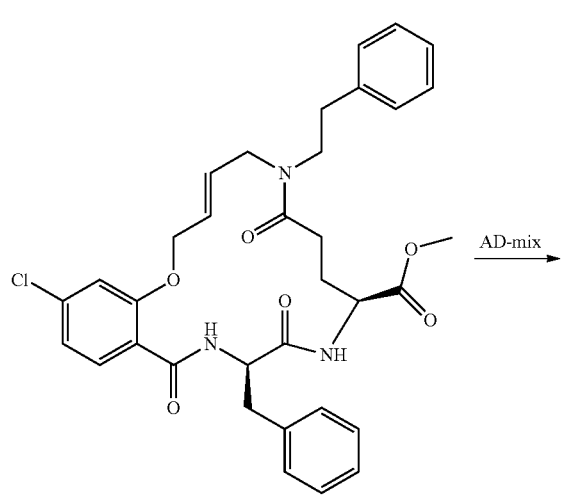

The macrocycle (E isomer) of Example 6 was dihydroxylated under Sharpless conditions to yield a diol in 58% yield.

Example 10

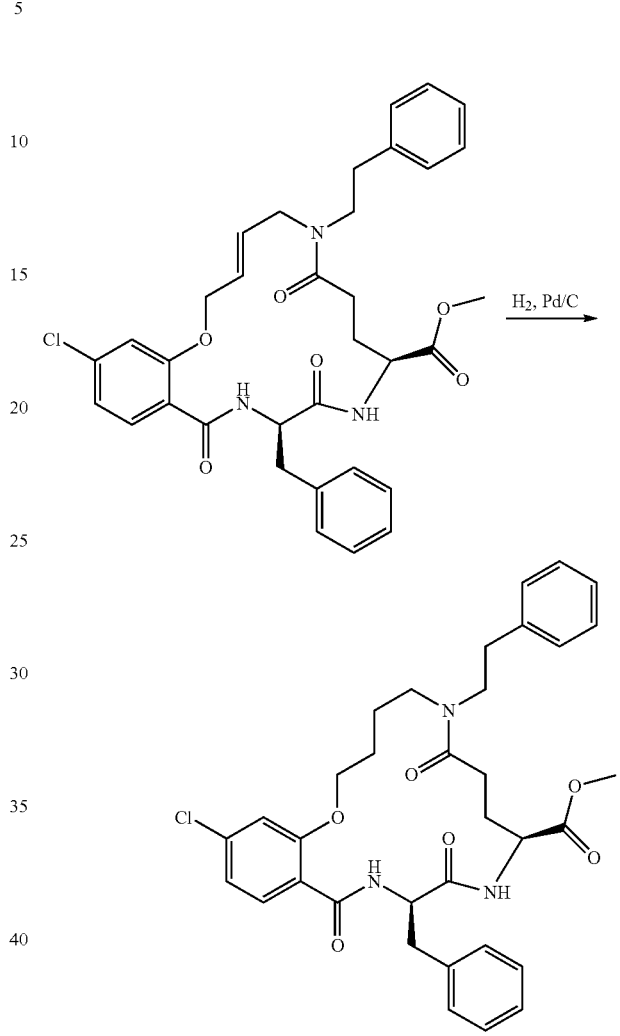

The resulting olefin from the ring closing metathesis reaction described in Example 9 can be hydrogenated using Pd/C under an atmosphere of hydrogen.

Example 11

This Example describes a protocol for assessing anti-IL23 activity in vitro.

Abbreviations

THP-1: human acute monocyte leukemia cell line

IFNγ: interferon gamma

SAC: *Staphylococcus aureus* cells, heat-killed and formalin-fixed

IKK2VI inhibitor: (5-phenyl-2-ureido)thiophene-3-carbaxamide

A. Screening Protocol

Materials

THP-1 cells and RPMI growth media containing 1% P/S and 10% FBS

IFNγ (Peprotech, Cat No. 300-02)

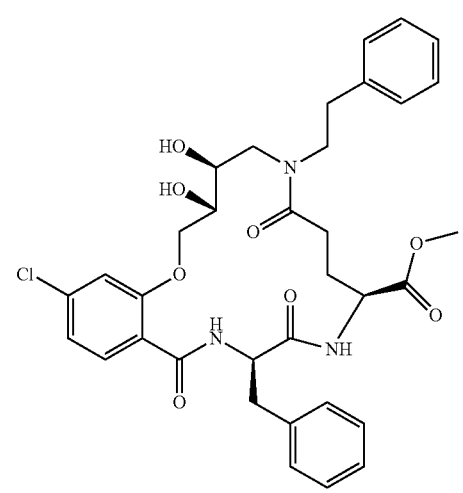

White clear bottom 96 well plates (Fisher, Cat No. 07-200-587, Corning #3903)
SAC (12% solution from Calbiochem, Cat No. 507858)
CELL TITER GLO® reagent (Promega, Cat No. G7573)
Positive controls, IKK2VI inhibitor (Calbiochem, Cat No. 401483)
Protocol:
Exponentially growing THP-1 cells (100 K/well in 100 μl) in standard RPMI media (1% P/S+10% FBS) containing 50 ng/ml IFNγ (1000 U/ml) are plated onto a white clear bottom 96 well plate and incubated at 37° C. 24 hours.
After 24 h incubation, 100 μl of RPMI media containing 2× concentrated test compound is added per well to the above cell-culture media (final concentration becomes 1×) and the plates are incubated for 1 h at 37° C. before stimulating with SAC._After the 1 h incubation with compound, 10 μl per well of 20× concentrated SAC solution in RPMI media is added to give a final concentration of 0.01%, and the plates are incubated at 37° C. for an additional 18 hours.
155 μl of the supernatant from each well is harvested and 50 μL of Cell Titer Glo reagent is added to the remaining 50 μl/well of the cell culture plate. The plate is incubated for 1-2 minutes on a shaker and then read for luminescence intensity to determine the compound cytotoxicity. The cell culture supernatant collected above to is used to carry out IL23 ELISA (65 μl-Supernatant) as described below.
Human IL-23 (p19/p40) ELISA Protocol (e-Biosciences)
Materials:
96-well high binding opaque white plates (from Pierce, Cat No. 15042)
1×PBS; 1×TBST washing buffer
Blocking Solution: 0.5% Casein in PBS (from BDH, Cat No. 440203H)
Dilution Solution: 1% BSA in PBS (10% BSA from Fisher, Cat No. 37525)
Capture antibody: Rat anti-human IL-23 (p19) (e-Biosciences, Cat. No. 14-7238-85)
Detection antibody: Primary Mouse Biotinylated anti-human IL-12 (p40/p70) (e-biosciences, Cat No. 13-7129-85); Secondary HRP-conjugated Streptavidin (R&D Systems, Cat No. DY998).
rHuman-IL-23 (e-biosciences, Cat No. 34-8239) (Suggested starting concentration=5 ng/ml in RPMI cell culture media)
Cell Culture Supernatant (65 μl from THP-1 cells primed with IFNγ (50 ng/ml-1000 U/ml) and stimulated with 0.01% SAC)
SuperSignal ELISA Pico Chemiluminescent substrate [Pierce, Cat No. 37069]
Coating Plates:
To 10.5 ml PBS are added 50 μl of anti-IL23 (p19) and capture antibody (2.5 μg/ml), after mixing, 100 μl of coating solution is added to each well of the 96 well white plates from Pierce, the plates are covered and incubated overnight at 4° C.
Blocking the Plates:
The anti-IL23 (p19)-antibody-coated plates are washed 2× using TBST and blocked using 200 μl of 0.5% Casein for 1.5-2 h at RT with shaking.
Addition of Supernatant and Detection:
The plates are washed 2× using TBST and the supernatant (65 μl/well) is transferred to the above pre-blocked/IL23 (p19)-antibody-coated 96 well plate and incubated at RT for 1.5 h with shaking.
The plate is washed 4× using TBST (plate washer) and add 100 μl/well detection antibody solution prepared from 2 μl of biotin labeled anti-IL-12 (p40/p70) antibody in 11 ml 1% BSA/PBS solution (1-5000 dilution). The plates are incubated for 1 hour with shaking at RT.

The plate is then washed 4× with TBST and 100 μL of HRP labeled Streptavidin (R&D Systems) solution (10 μl/10 ml 1% BSA solution) is added and the plate is incubated at RT for another 45 min with shaking.
After 45 min, the plate is washed with TBST 4× and 100 μL/well Super Signal ELISA Pico Chemiluminescent Substrate from Pierce (3.5 ml A+3.5 ml B+3.5 ml MQ water) is added, the plate is allowed to shake for 1-2 minutes then read on a plate reader.
In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:
1. A method for making a macrocycle, comprising:
providing an acyclic precursor; and
forming the macrocycle from the acyclic precursor, the macrocycle having a formula

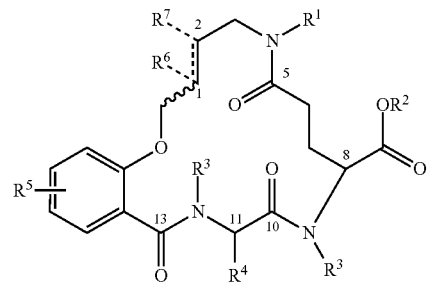

where $R^1$ is selected from hydrogen, aliphatic, substituted aliphatic, aromatic, substituted aromatic, arylalkyl, substituted arylalkyl, benzoyl, ester, ketone, tert-butoxycarbonyl, 9H-fluoren-9-ylmethoxycarbonyl, allyloxycarbonyl, benzyloxy carbonyl, trichloroethoxycarbonyl, triphenylmethyl, and sulfonyl;
$R^2$ is selected from hydrogen and aliphatic;
each $R^3$ is independently selected from hydrogen, aliphatic, substituted aliphatic, aromatic, substituted aromatic, arylalkyl, substituted arylalkyl, benzoyl, ester, ketone, tert-butoxycarbonyl, 9H-fluoren-9-ylmethoxycarbonyl, allyloxycarbonyl, benzyloxy carbonyl, trichloroethoxycarbonyl, triphenylmethyl, and sulfonyl;
$R^4$ is selected from hydrogen, methyl, —CH(CH$_3$)CH$_2$CH$_3$, —CH$_2$CH(CH$_3$)$_2$, —(CH$_2$)$_2$SCH$_3$, benzyl, substituted benzyl, 3-indole, —CH(CH$_3$)$_2$, —CH$_2$OH, —CH(OH)(CH$_3$), —CH$_2$C(O)NH$_2$, —(CH$_2$)$_2$C(O)NH$_2$, —CH$_2$SH, —CH$_2$SeH, —(CH$_2$)$_3$NHC(NH$_2$$^+$)NH$_2$, —CH$_2$(imidazole), —(CH$_2$)$_4$NH$_2$, —CH$_2$C(O)OH, —(CH$_2$)$_2$C(O)OH, and any natural or non-natural amino acid side chain;
or $R^3$ and $R^4$ individually are, or together form, a 5-membered ring;
$R^5$ is selected from aliphatic, substituted aliphatic, alkoxy, substituted alkoxy, amine, substituted amine, amide, substituted amide, aryl, substituted aryl, arylalkyl, substituted arylalkyl, cyclic, substituted cyclic, ester, ether, formyl, halogen, heterocyclic, substituted heterocyclic, heteroaryl, substituted heteroaryl, hydrogen, hydroxyl, ketone, substituted ketone, nitro, nitroso, protecting groups, silyl, silyl ether, silyl ester, thiol, thioether, and thioester;

"----" indicates an optional double bond, having either Z or E geometry; and each of $R^6$ and $R^7$ can be hydrogen when the optional double bond is present, or when the optional double bond is not present, each of $R^6$ and $R^7$ independently is selected from aliphatic, amino, halogen, hydrogen, and hydroxyl;

or $R^6$ and $R^7$ together form an epoxide or aziridine.

2. The method according to claim 1 where the acyclic precursor has a formula selected from

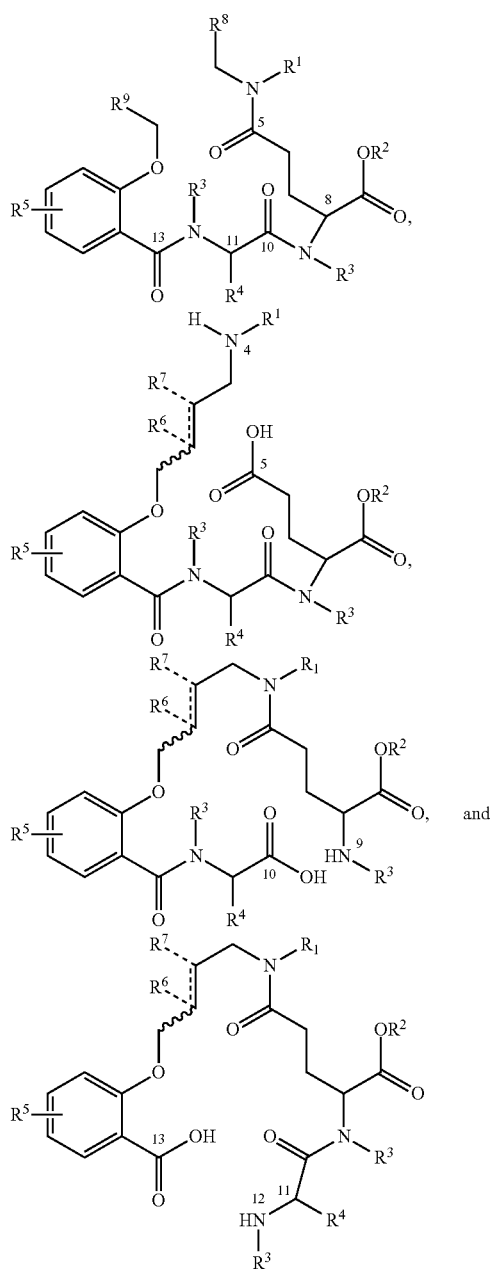

where $R^1$ is selected from hydrogen, aliphatic, substituted aliphatic, aromatic, substituted aromatic, arylalkyl, substituted arylalkyl, benzoyl, ester, ketone, substituted ketone, triphenylmethyl, and sulfonyl;

$R^2$ is selected from hydrogen and aliphatic;

each $R^3$ is independently selected from hydrogen, aliphatic, substituted aliphatic, aromatic, substituted aromatic, arylalkyl, substituted arylalkyl, benzoyl, ester, ketone, tert-butoxycarbonyl, 9H-fluoren-9-ylmethoxycarbonyl, allyloxycarbonyl, benzyloxy carbonyl, trichloroethoxycarbonyl, triphenylmethyl, and sulfonyl;

$R^4$ is selected from hydrogen, methyl, —CH($CH_3$)$CH_2CH_3$, —$CH_2CH(CH_3)_2$, —$(CH_2)_2SCH_3$, benzyl, substituted benzyl, 3-indole, —CH($CH_3$)$_2$, —$_{CH_2}$OH, —CH(OH)($CH_3$), —$CH_2C(O)NH_2$, —$(CH_2)_2C(O)NH_2$, —$CH_2SH$, —$CH_2SeH$, —$(CH_2)_3NHC(NH_2{}^+)NH_2$, —$CH_2$(imidazole), —$(CH_2)_4NH_2$, —$CH_2C(O)OH$, —$(CH_2)_2C(O)OH$, and any natural or non-natural amino acid side chain;

or $R^3$ and $R^4$ individually are, or together form, a 5-membered ring;

$R^5$ is selected from aliphatic, substituted aliphatic, alkoxy, particularly lower alkoxy, substituted alkoxy, amine, substituted amine, amide, substituted amide, aryl, substituted aryl, arylalkyl, substituted arylalkyl, cyclic, substituted cyclic, ester, ether, formyl, halogen, heterocyclic, substituted heterocyclic, heteroaryl, substituted heteroaryl, hydrogen, hydroxyl, ketone, substituted ketone, nitro, nitroso, protecting groups, silyl, silyl ether, silyl ester, thiol, thioether, and thioester;

$R^8$ and $R^9$ independently are selected from —C(O)H, —$CH_2SO_2Ph$, —$CH_2PPh_3$, —$CH_2P(O)(OCH_2CF_3)_2$, —$CH_2P(O)(OEt)_2$, —$CH_2SO_2$-tetrazole, and —$CR^{10}$=$CR^{11}R^{12}$, where $R^{10}$, $R^{11}$, and $R^{12}$ independently are selected from hydrogen, aliphatic, substituted aliphatic, aromatic, substituted aromatic, arylalkyl, and substituted arylalkyl;

"----" indicates an optional double bond, having either Z or E geometry; and each of $R^6$ and $R^7$ can be hydrogen when the optional double bond is present, or when the optional double bond is not present, each of $R^6$ and $R^7$ independently is selected from aliphatic, amino, halogen, hydrogen, and hydroxyl;

or $R^6$ and $R^7$ together form an epoxide or aziridine.

3. The method according to claim 1 wherein forming the macrocycle comprises exposing the acyclic precursor to ring closing metathesis reagents selected from

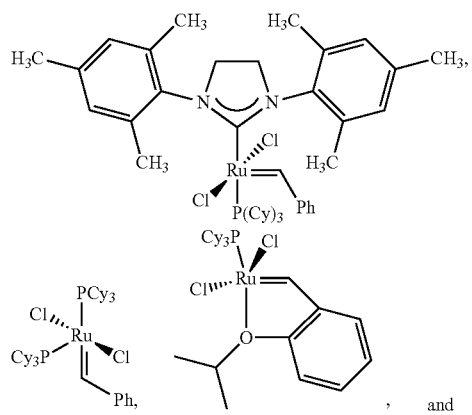

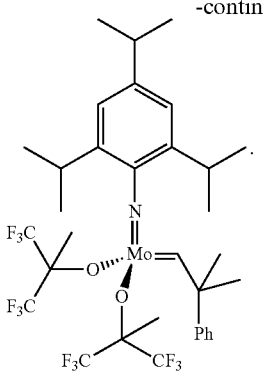
4. The method according to claim 1 where the acyclic precursor has a formula
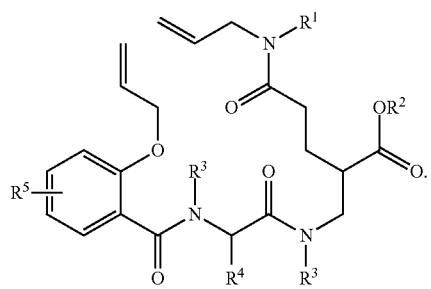
5. The method according to claim 1 where the acyclic precursor is selected from
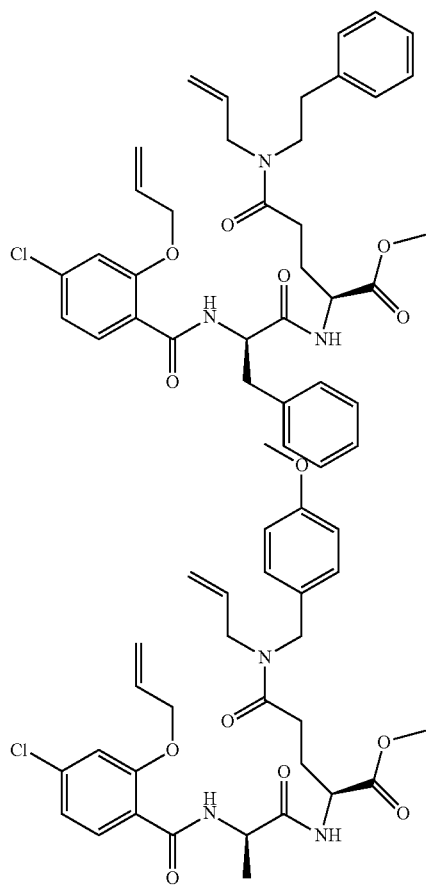
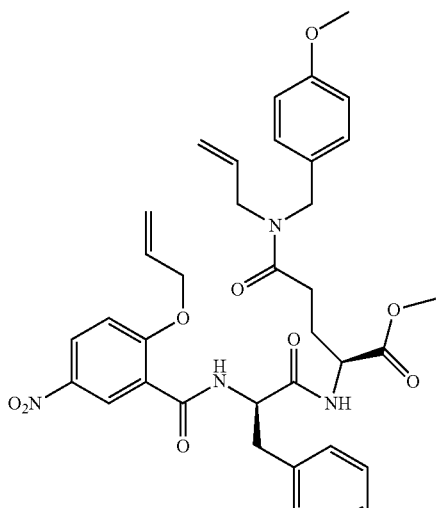
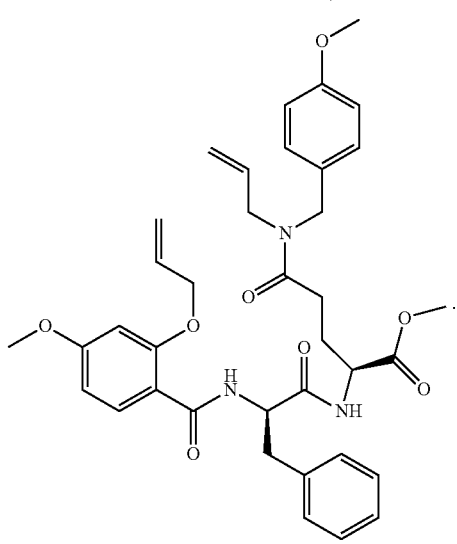
6. The method according to claim 1 where the macrocycle is selected from
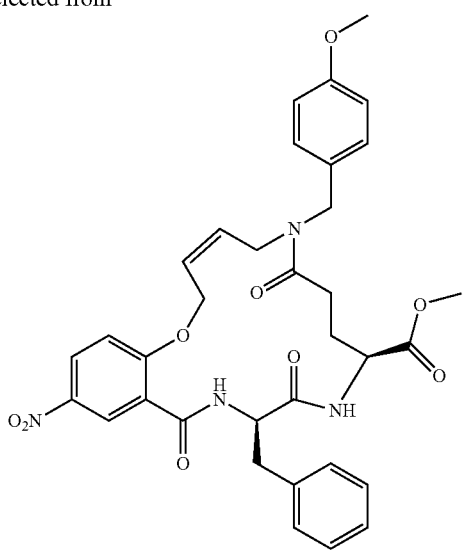

105
-continued
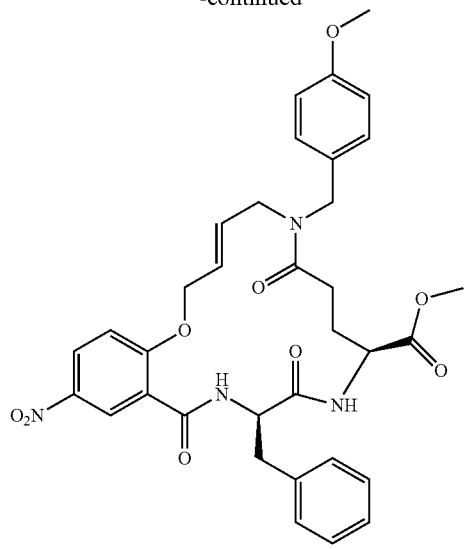
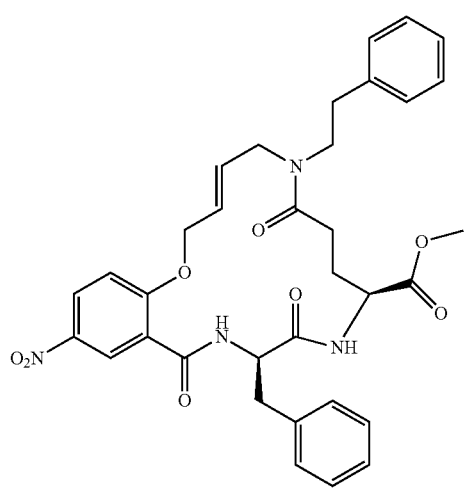
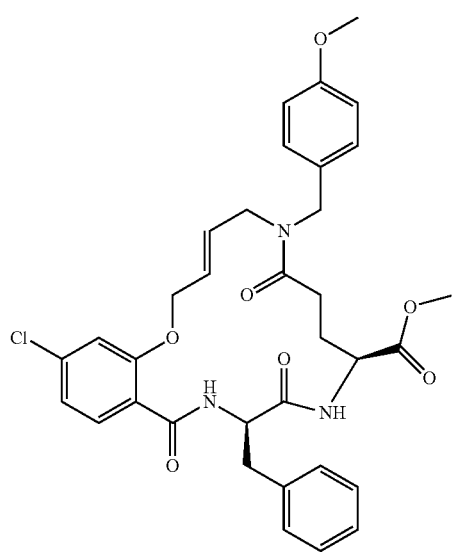
106
-continued
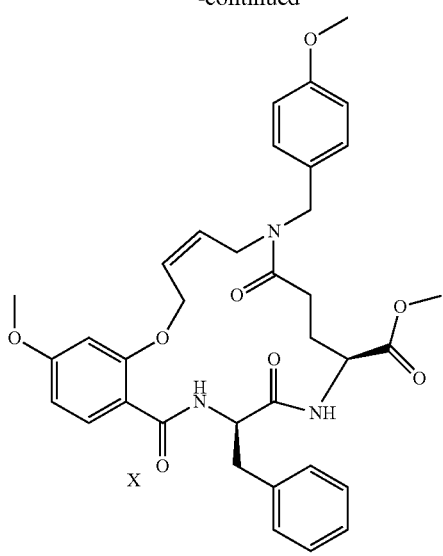
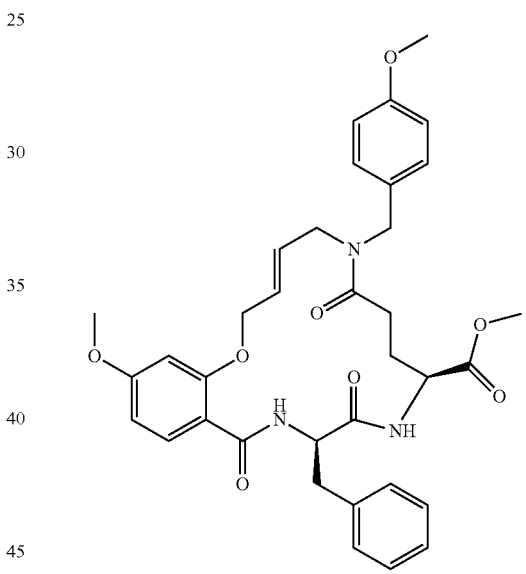
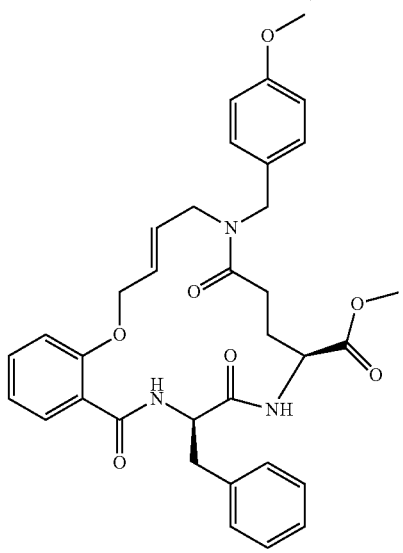

107
-continued
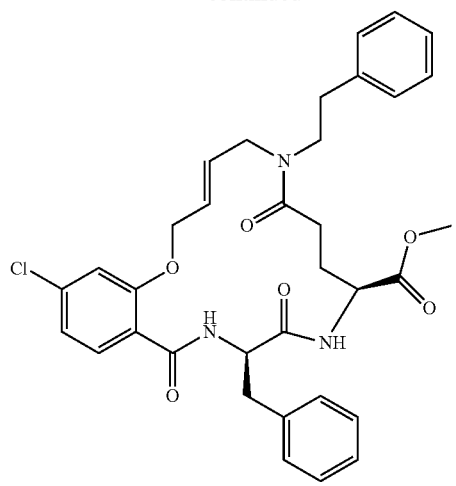
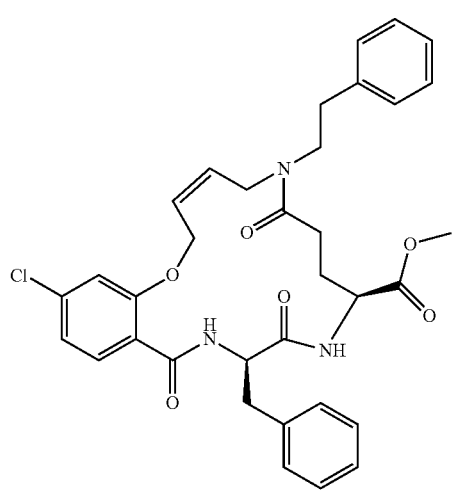
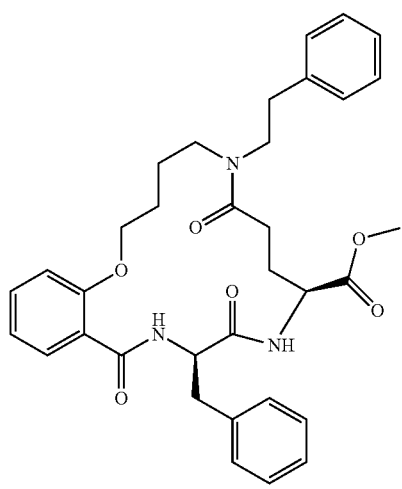
108
-continued
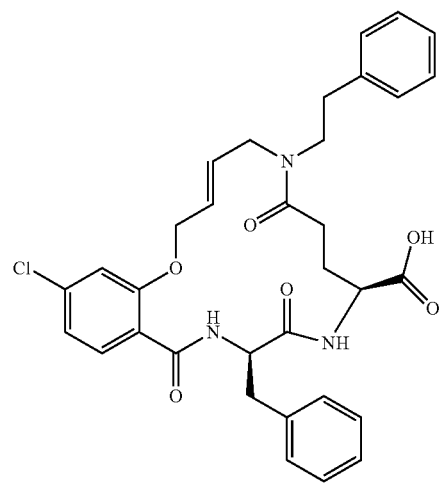
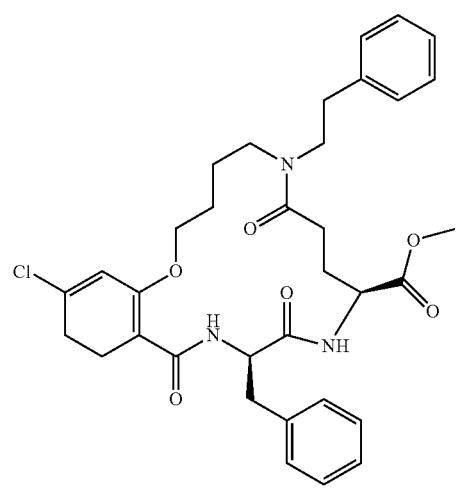
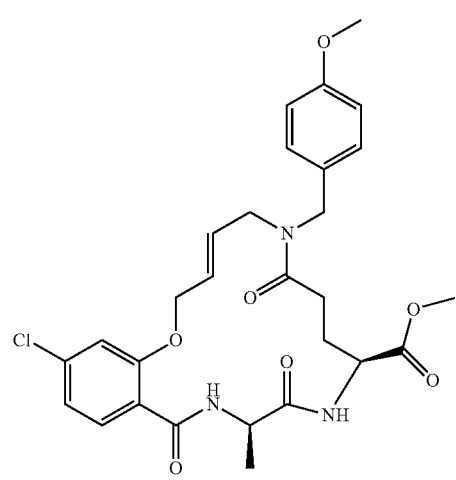

-continued

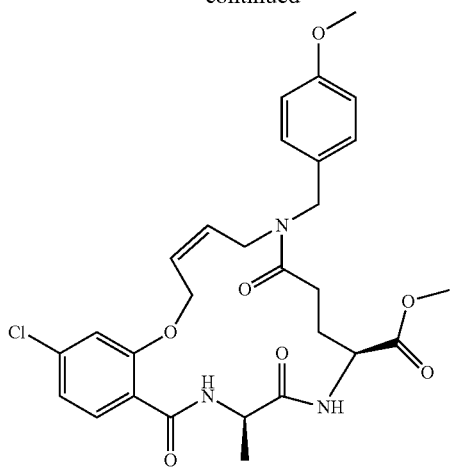

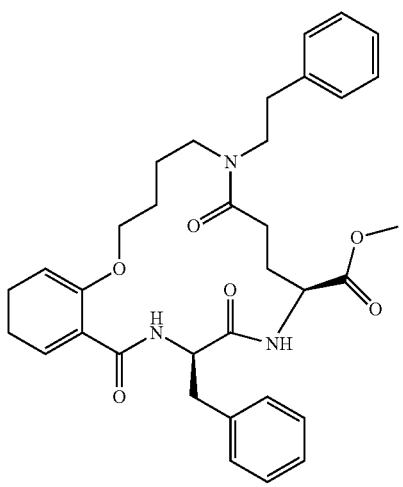

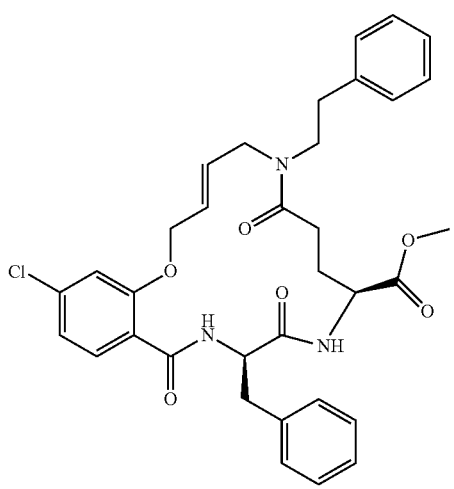

-continued

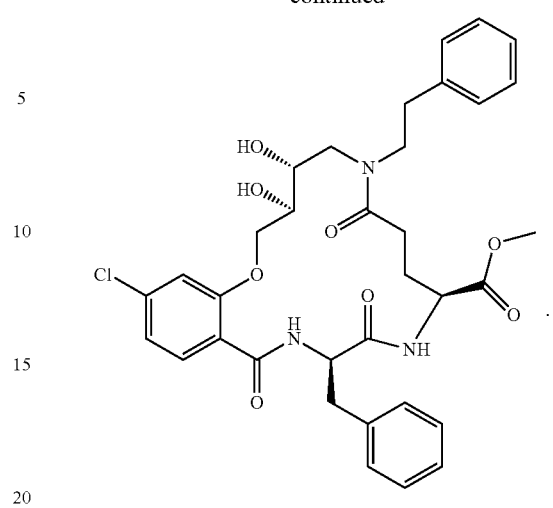

7. The method according to claim 1, wherein providing the acyclic precursor comprises coupling a salicylic acid derivative with a dipeptide using peptide coupling conditions.

8. The method according to claim 7 where the dipeptide comprises naturally occurring amino acids, non-naturally occurring amino acids, and combinations thereof.

9. The method according to claim 7 where the dipeptide includes a glutamic acid derivative.

10. The method according to claim 7 where the dipeptide is formed by:
reacting a halogenated compound with a first amine compound to form a second amine compound, the halogenated compound having a formula

where $R^8$ is selected from —C(O)H, —CH$_2$SO$_2$Ph, —CH$_2$PPh$_3$, —CH$_2$P(O)(OCH$_2$CF$_3$)$_2$, —CH$_2$P(O)(OEt)$_2$, —CH$_2$SO$_2$-tetrazole, and —CR$^{10}$=CR$^{11}$R$^{12}$, with R$^{10}$, R$^{11}$, and R$^{12}$ independently being selected from hydrogen, aliphatic, substituted aliphatic, aromatic, substituted aromatic, arylalkyl, and substituted arylalkyl; and X is selected from I, Br, Cl, F;
the first amine compound having a formula

where $R^1$ is selected from hydrogen, aliphatic, substituted aliphatic, aromatic, substituted aromatic, arylalkyl, substituted arylalkyl, ester, ketone, substituted ketone, benzoyl, triphenylmethyl, and sulfonyl; and
subjecting the second amine compound to an amide bond formation reaction with a protected glutamic acid compound having a formula

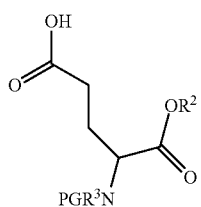

wherein $R^2$ is selected from hydrogen or aliphatic, and PG is selected from arylalkyl, substituted arylalkyl, benzoyl, ester, ketone, substituted ketone, triphenylmethyl, and sulfonyl.

11. The method according to claim 10 wherein the amide bond formation reaction comprises using an activating group selected from N-ethyl-N'-(3-dimethylaminopropyl)carbodiimide (EDC), 1-ethyl-3-(3-dimethylaminopropyl)carbodiimide hydrochloride (EDCI), dicyclohexylcarbodiimide (DCC), carbonyl diimidazole (CDI), 1-hydroxybenzotriazole (HOBt), 1-hydroxy-7-aza-benzotriazole (HOAt), and o-(7-azabenzotriazol-1-yl)-N,N,N',N'-tetramethyluronium hexafluorophosphate (HATU).

12. The method according to claim 7 where the salicylic acid derivative has a formula

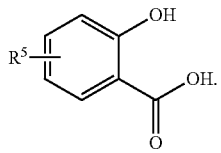

13. The method according to claim 7 where the salicylic acid derivative is selected from

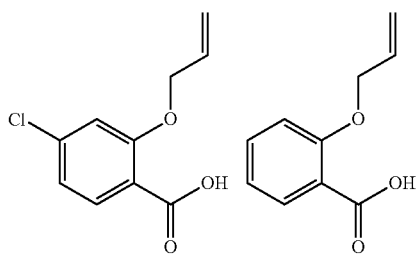

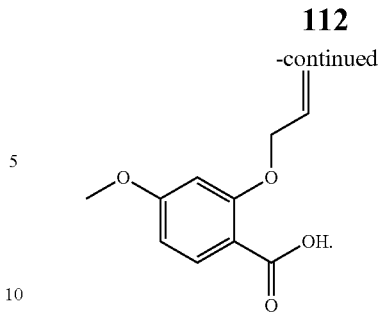

14. The method according to claim 10 wherein the dipeptide has a formula

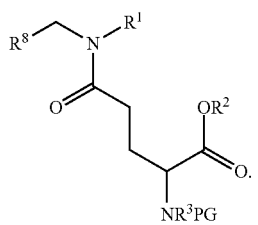

15. The method according to claim 14 where the dipeptide is selected from

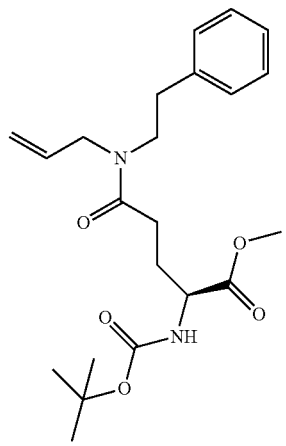

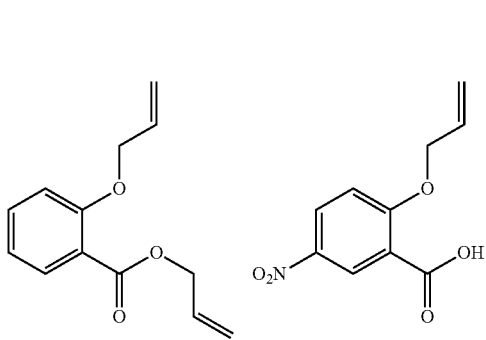

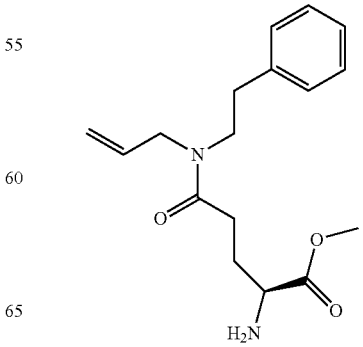

-continued

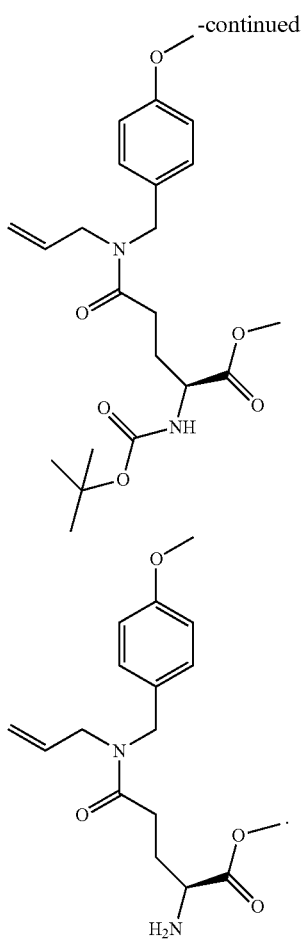

16. The method according to claim 7 further comprising forming an intermediate by performing a peptide coupling between the dipeptide and a protected amino acid derivative, wherein the intermediate has a formula

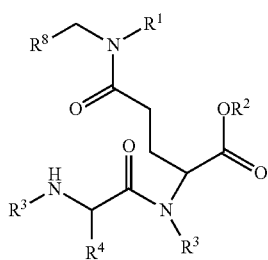

where $R^1$ is selected from hydrogen, aliphatic, substituted aliphatic, aromatic, substituted aromatic, arylalkyl, substituted arylalkyl, benzoyl, ester, ketone, substituted ketone, triphenylmethyl, and sulfonyl;

$R^2$ is selected from hydrogen and aliphatic;

each $R^3$ is independently selected from hydrogen, aliphatic, substituted aliphatic, alkyl, aromatic, substituted aromatic, arylalkyl, substituted arylalkyl, benzoyl, ester, and ketone;

$R^4$ is selected from hydrogen, methyl, —CH($CH_3$) $CH_2CH_3$, —$CH_2CH(CH_3)_2$, —$(CH_2)_2SCH_3$, benzyl, substituted benzyl, 3-indole, —CH($CH_3)_2$, —$CH_2OH$, —CH(OH)($CH_3$), —$CH_2C(O)NH_2$, —$(CH_2)_2C(O)$ $NH_2$, —$CH_2SH$, —$CH_2SeH$, —$(CH_2)_3NHC(NH_2^+)$ $NH_2$, —$CH_2$(imidazole), —$(CH_2)_4NH_2$, —$CH_2C(O)$ OH, —$(CH_2)_2C(O)OH$, and any natural or non-natural amino acid side chain;

or $R^3$ and $R^4$ individually are, or together form, a 5-membered ring;

$R^8$ is selected from —C(O)H, —$CH_2SO_2Ph$, —$CH_2PPh_3$, —$CH_2P(O)(OCH_2CF_3)_2$, —$CH_2P(O)(OEt)_2$, —$CH_2SO_2$-tetrazole, and —$CR^{10}$+$CR^{11}R^{12}$, with $R^{10}$, $R^{11}$, and $R^{12}$ independently being selected from hydrogen, aliphatic, aromatic, substituted aromatic, arylalkyl, substituted arylalkyl;

the dipeptide has a formula

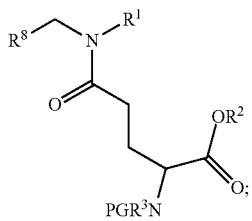

and the protected amino acid derivative has a formula

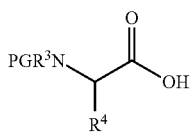

wherein PG is selected from arylalkyl, substituted arylalkyl, benzoyl, ester, ketone, substituted ketone, triphenylmethyl, and sulfonyl.

17. The method according to claim 16 where the intermediate is selected from

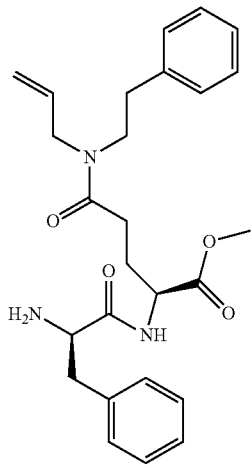

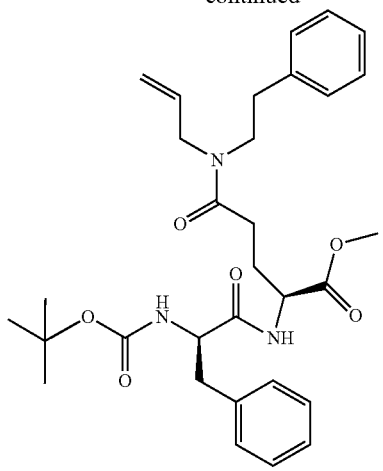

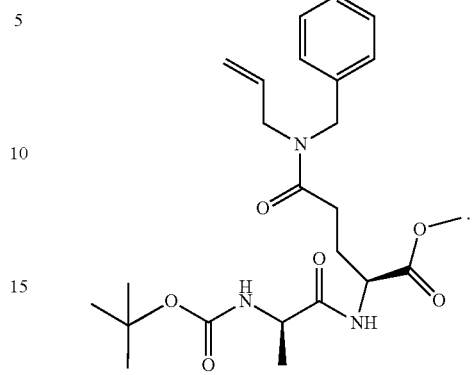

18. The method according to claim 7, further comprising: reacting, under basic conditions, a salicylic acid with a halogenated compound to form a bis-substituted compound, the salicylic acid derivative having a formula

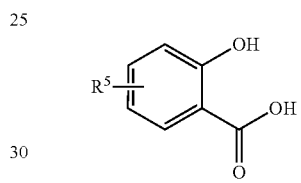

wherein $R^5$ is selected from aliphatic, substituted aliphatic, alkoxy, particularly lower alkoxy, substituted alkoxy, amine, substituted amine, amide, substituted amide, aryl, substituted aryl, arylalkyl, substituted arylalkyl, cyclic, substituted cyclic, ester, ether, formyl, halogen, heterocyclic, substituted heterocyclic, heteroaryl, substituted heteroaryl, hydrogen, hydroxyl, ketone, substituted ketone, nitro, nitroso, protecting groups, silyl, silyl ether, silyl ester, thiol, thioether, and thioester;

the halogenated compound having a formula

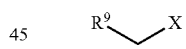

wherein $R^9$ is selected from —C(O)H, —CH$_2$SO$_2$Ph, —CH$_2$PPh$_3$, —CH$_2$P(O)(OCH$_2$CF$_3$)$_2$, —CH$_2$P(O)(OEt)$_2$, —CH$_2$SO$_2$-tetrazole, and —CR$^{10}$=CR$^{11}$R$^{12}$, with $R^{10}$, $R^{11}$, and $R^{12}$ independently being selected from hydrogen, aliphatic, substituted aliphatic, aromatic, substituted aromatic, arylalkyl, and substituted arylalkyl; and X is selected from I, Br, Cl, and F, thereby forming the bis-substituted compound; and hydrolyzing the bis-substituted compound to form a salicylic acid derivative having a formula

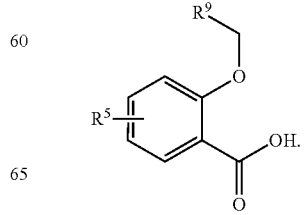

19. The method according to claim 16 where the protected amino acid derivative is selected from

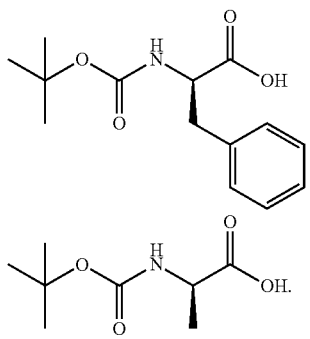

20. The method according to claim 16 further comprising reacting the intermediate with the hydrolyzed salicylic acid derivative of claim 18 to provide an acyclic precursor having a formula

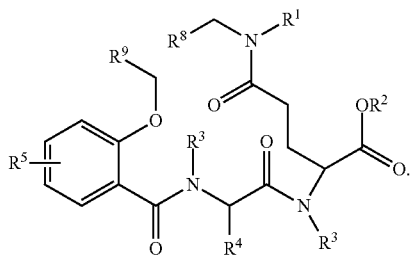

21. The method according to claim 1 wherein:
the acyclic precursor has a formula

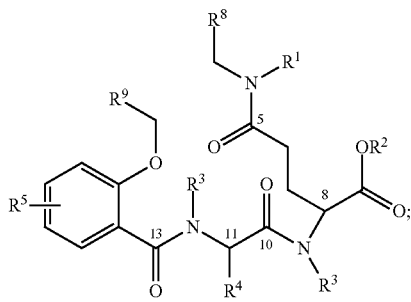

and
forming the macrocycle comprises performing a ring closing reaction to close the acyclic precursor.

22. The method according to claim 21 where:
$R^8$ is —C(O)H; $R^9$ is selected from —CH$_2$SO$_2$Ph, —CH$_2$PPh$_3$, —CH$_2$P(O)(OCH$_2$CF$_3$)$_2$, —CH$_2$P(O)(OEt)$_2$, and —CH$_2$SO$_2$-tetrazole; or where $R^9$ is —C(O)H, and $R_8$ is selected from —CH$_2$SO$_2$Ph, —CH$_2$PPh$_3$, —CH$_2$P(O)(OCH$_2$CF$_3$)$_2$, —CH$_2$P(O)(OEt)$_2$, and —CH$_2$SO$_2$-tetrazole; and where the ring closing reaction is a ring closing olefination reaction selected from Wittig olefination, Horner-Wadsworth-Emmons olefination, Gennari-Still olefination, Julia-Lythgoe and Julia-Kocienski olefinations.

23. A compound having a formula

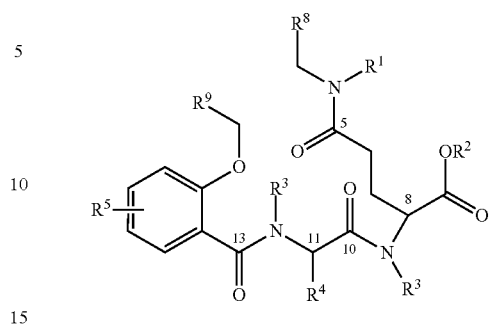

where:

$R^1$ is selected from hydrogen, aliphatic, substituted aliphatic, aromatic, substituted aromatic, arylalkyl, substituted arylalkyl, benzoyl, ester, ketone, substituted ketone triphenylmethyl, and sulfonyl;

$R^2$ is selected from hydrogen and aliphatic;

each $R^3$ is independently selected from hydrogen, aliphatic, substituted aliphatic, aromatic, substituted aromatic, arylalkyl, substituted arylalkyl, benzoyl, ester, ketone, substituted ketone;

$R^4$ is selected from hydrogen, methyl, —CH(CH$_3$)CH$_2$CH$_3$, —CH$_2$CH(CH$_3$)$_2$, —(CH$_2$)$_2$SCH$_3$, benzyl, substituted benzyl, 3-indole, —CH(CH$_3$)$_2$,—CH$_2$OH, —CH(OH)(CH$_3$), —CH$_2$C(O)NH$_2$, —(CH$_2$)$_2$C(O)NH$_2$, —CH$_2$SH, —CH$_2$SeH, —(CH$_2$)$_3$NHC(NH$_2$$^+$)NH$_2$, —CH$_2$(imidazole), —(CH$_2$)$_4$NH$_2$, —CH$_2$C(O)OH, —(CH$_2$)$_2$C(O)OH, and any natural or non-natural amino acid side chain;

or $R^3$ and $R^4$ individually are, or together form, a 5-membered ring;

$R^5$ is selected from aliphatic, substituted aliphatic, alkoxy, substituted alkoxy, amine, substituted amine, amide, substituted amide, aryl, substituted aryl, arylalkyl, substituted arylalkyl, cyclic, substituted cyclic, ester, ether, formyl, halogen, heterocyclic, substituted heterocyclic, heteroaryl, substituted heteroaryl, hydrogen, hydroxyl, ketone, substituted ketone, nitro, nitroso, protecting groups, silyl, silyl ether, silyl ester, thiol, thioether, and thioester; and $R^8$ is selected from —C(O)H, —CH$_2$SO$_2$Ph, —CH$_2$PPh$_3$, —CH$_2$P(O)(OCH$_2$CF$_3$)$_2$, —CH$_2$P(O)(OEt)$_2$, —CH$_2$SO$_2$-tetrazole, and —CR$^{=CR^{11}}$R$^{12}$, where $R^{10}$, $R^{11}$, and $R^{12}$ independently are selected from hydrogen, aliphatic, aromatic, substituted aromatic, arylalkyl, substituted arylalkyl; and if $R^8$ is —CR$^{10}$=CR$^{11}$R$^{12}$, then $R^9$ is —CR$^{10}$=CR$^{11}$R$^{12}$; or if $R^8$ is —C(O)H, then $R^9$ is selected from —CH$_2$SO$_2$Ph, —CH$_2$PPh$_3$, —CH$_2$P(O)(OCH$_2$CF$_3$)$_2$, —CH$_2$P(O)(OEt)$_2$, and —CH$_2$SO$_2$-tetrazole; or if $R^9$ is —C(O)H, then $R^8$ is selected from —CH$_2$SO$_2$Ph, —CH$_2$PPh$_3$, —CH$_2$P(O)(OCH$_2$CF$_3$)$_2$, —CH$_2$P(O)(OEt)$_2$, and —CH$_2$SO$_2$-tetrazole.

24. The compound according to claim 23 wherein the compound is selected from

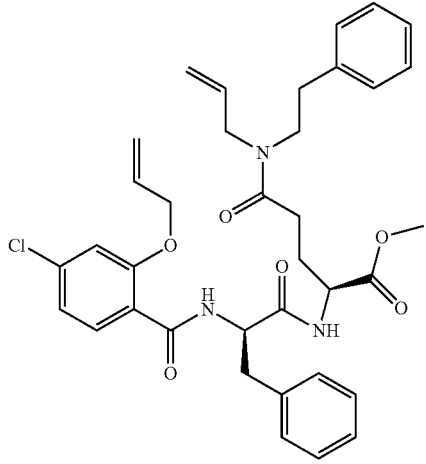

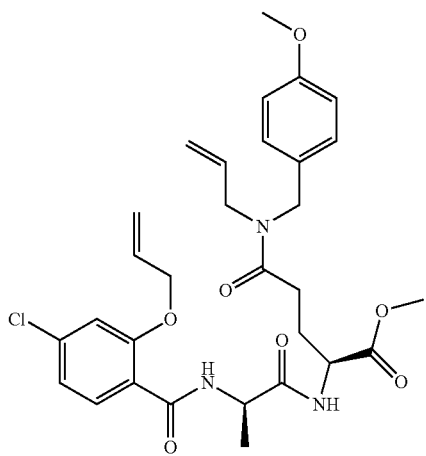

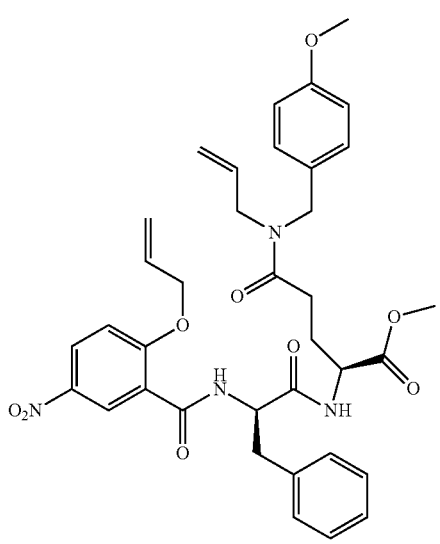

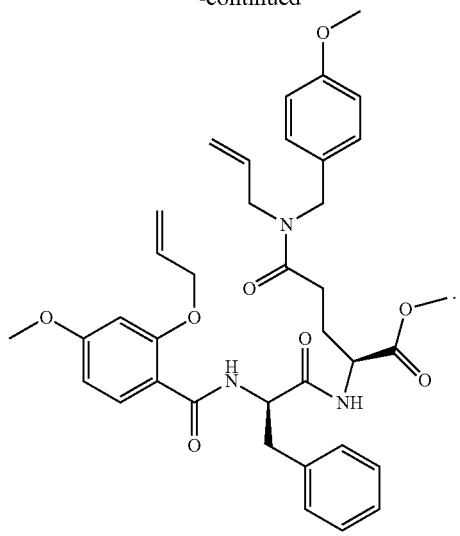

25. The method according to claim 1 further comprising chemically modifying the macrocycle via a palladium coupling reaction, a hydrogenation reaction, or an oxidation reaction.

26. The method according to claim 1 where forming the macrocycle comprises forming the macrocycle by ring closing amide bond formation, by ring closing metathesis, or by ring closing olefination.

27. A compound having a formula

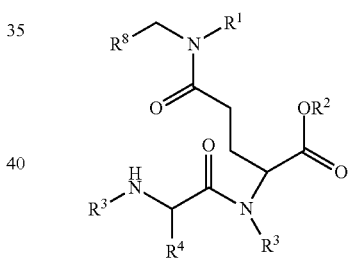

where:
$R^1$ is selected from hydrogen, aliphatic, substituted aliphatic, aromatic, substituted aromatic, arylalkyl, substituted arylalkyl, benzoyl, ester, ketone, substituted ketone, triphenylmethyl, and sulfonyl;
$R^2$ is selected from hydrogen and aliphatic;
each $R^3$ is independently selected from hydrogen, aliphatic, substituted aliphatic, alkyl, aromatic, substituted aromatic, arylalkyl, substituted arylalkyl, benzoyl, ester, and ketone;
$R^4$ is selected from hydrogen, methyl, —CH($CH_3$) $CH_2CH_3$, —$CH_2CH(CH_3)_2$, —$(CH_2)_2SCH_3$, benzyl, substituted benzyl, 3-indole, —CH($CH_3)_2$, —$CH_2OH$, —CH(OH)($CH_3$), —$CH_2C(_O)NH_2$, —$(CH_2)_2C(O)$ $NH_2$, —$CH_2SH$, —$CH_2SeH$, —$(CH_2)_3NHC(NH_{2+})$ $NH_2$, —$CH_2$(imidazole), —$(CH_2)_4NH_2$, —$CH_2C(O)$ OH, —$(CH_2)_2C(O)OH$, and any natural or non-natural amino acid side chain;
or $R^3$ and $R^4$ individually are, or together form, a 5-membered ring; and
$R^8$ is selected from —C(O)H, —$CH_2SO_2Ph$, —$CH_2PPh_3$, —$CH_2P(O)(OCH_2CF_3)_2$, —$CH_2P(O)(OEt)_2$, —CH$_2$SO$_2$-tetrazole, and —CR$^{10}$=CR$^{11}$R$^{12}$, where R$^{10}$,R$^{11}$, and R$^{12}$ independently are selected from hydrogen, aliphatic, aromatic, substituted aromatic, arylalkyl, and substituted arylalkyl.

28. A compound selected from

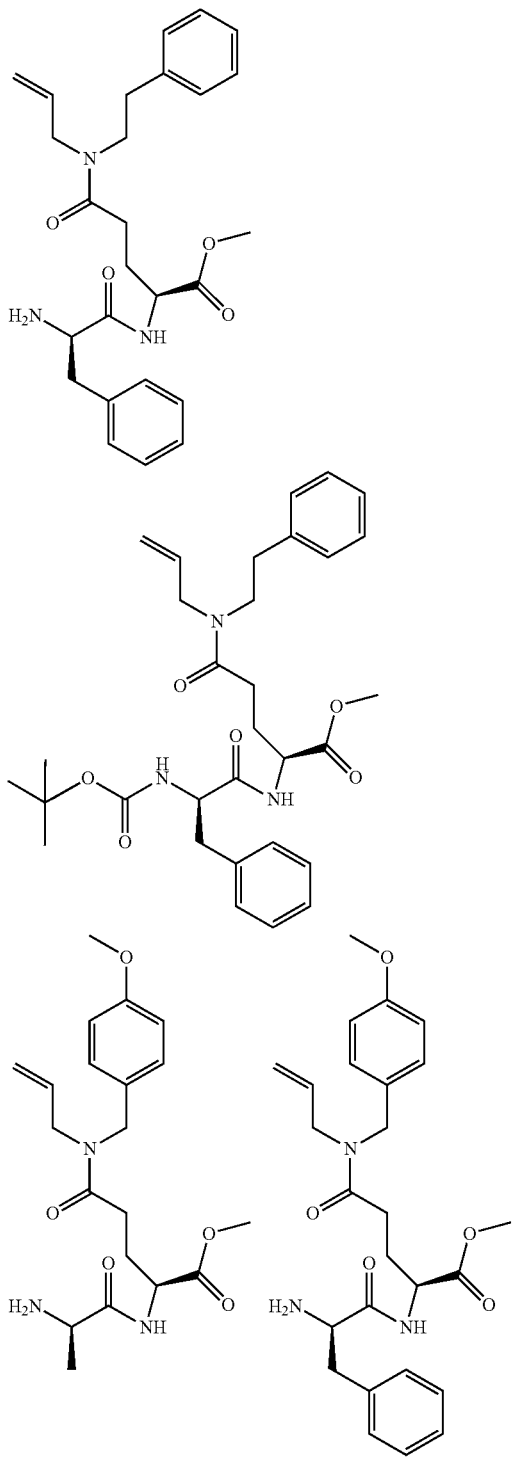

-continued

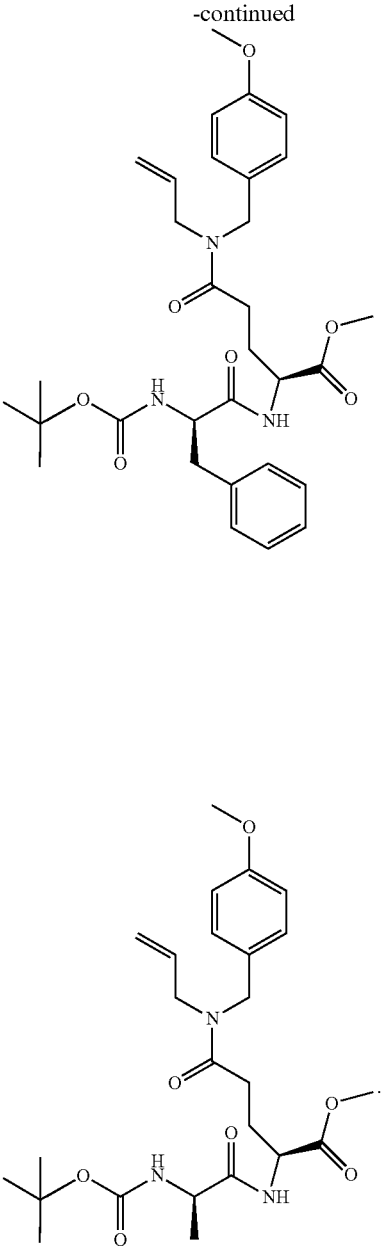

29. The compound according to claim 27 where R$^1$ is selected from aliphatic, substituted aliphatic, aromatic, substituted aromatic, arylalkyl, substituted arylalkyl, benzoyl, ester, ketone, substituted ketone, triphenylmethyl, and sulfonyl.

30. The compound according to claim 27 where R$^2$ is aliphatic.

* * * * *